United States Patent
Tampella et al.

(10) Patent No.: US 12,152,079 B2
(45) Date of Patent: Nov. 26, 2024

(54) NUCLEIC ACIDS ENCODING IL-13 RECEPTOR ALPHA 2 (IL13Ra2) CHIMERIC ANTIGEN RECEPTOR FOR TUMOR SPECIFIC T CELL IMMUNOTHERAPY

(71) Applicant: Seattle Children's Hospital, Seattle, WA (US)

(72) Inventors: Giacomo Tampella, Seattle, WA (US); Michael C. Jensen, Seattle, WA (US)

(73) Assignee: Seattle Children's Research Institute, Seattle, WA (US)

(*) Notice: Subject to any disclaimer, the term of this patent is extended or adjusted under 35 U.S.C. 154(b) by 1076 days.

(21) Appl. No.: 16/979,471

(22) PCT Filed: Mar. 12, 2019

(86) PCT No.: PCT/US2019/021823
§ 371 (c)(1),
(2) Date: Sep. 9, 2020

(87) PCT Pub. No.: WO2019/178078
PCT Pub. Date: Sep. 19, 2019

(65) Prior Publication Data
US 2021/0000875 A1    Jan. 7, 2021

Related U.S. Application Data

(60) Provisional application No. 62/643,055, filed on Mar. 14, 2018.

(51) Int. Cl.
| | | |
|---|---|---|
| C07K 16/28 | (2006.01) | |
| A61K 35/17 | (2015.01) | |
| A61K 39/39 | (2006.01) | |
| A61K 39/395 | (2006.01) | |
| A61P 35/00 | (2006.01) | |
| C07K 14/705 | (2006.01) | |
| C07K 14/725 | (2006.01) | |

(52) U.S. Cl.
CPC .......... *C07K 16/2866* (2013.01); *A61K 35/17* (2013.01); *A61K 39/3955* (2013.01); *A61P 35/00* (2018.01); *C07K 14/7051* (2013.01); *C07K 14/70521* (2013.01); *C07K 14/70578* (2013.01); *C07K 2319/03* (2013.01)

(58) Field of Classification Search
CPC ............ C07K 16/2866; C07K 2319/03; C07K 14/7051; C07K 14/70521; C07K 14/70578; A61K 39/3955
See application file for complete search history.

(56) References Cited

U.S. PATENT DOCUMENTS

| | | |
|---|---|---|
| 8,822,647 B2 | 9/2014 | Jensen |
| 2009/0098142 A1 | 4/2009 | Kasaian et al. |
| 2012/0148552 A1 | 6/2012 | Jensen |
| 2014/0271635 A1 | 9/2014 | Brogdon et al. |
| 2015/0266962 A1 | 9/2015 | Ma et al. |
| 2015/0299756 A1 | 10/2015 | Hishiya et al. |
| 2015/0306141 A1 | 10/2015 | Jensen |
| 2016/0152723 A1* | 6/2016 | Chen ................. C07K 14/70521 435/254.2 |
| 2016/0340649 A1 | 11/2016 | Brown et al. |
| 2017/0209543 A9 | 7/2017 | Jensen |
| 2017/0224733 A1 | 8/2017 | Badie et al. |
| 2020/0061114 A1* | 2/2020 | Abate-Daga ....... C07K 14/7051 |
| 2021/0017246 A1 | 1/2021 | Tampella et al. |

FOREIGN PATENT DOCUMENTS

| | | |
|---|---|---|
| JP | 2016503295 A | 2/2016 |
| JP | 2016525881 A | 9/2016 |
| JP | 2016195601 A | 11/2016 |
| JP | 2017529081 A | 10/2017 |
| JP | 2017534262 A | 11/2017 |
| WO | WO2014031687 A1 | 2/2014 |
| WO | WO2014072888 A1 | 5/2014 |
| WO | WO2016044811 A1 | 3/2016 |
| WO | WO2016123142 A1 | 8/2016 |
| WO | WO2017015490 A1 | 1/2017 |
| WO | WO2017040930 A2 | 3/2017 |
| WO | WO2017172981 A2 | 10/2017 |
| WO | WO2017214092 A1 | 12/2017 |
| WO | WO2018023093 A1 | 2/2018 |
| WO | WO2019178085 A1 | 9/2019 |

OTHER PUBLICATIONS

Knudson et al (2022. Frontiers in Immunology. 13: 1-10).*
Office Action Dated Apr. 19, 2023 for Eurasian patent application No. 202091982, a foreign counterpart of U.S. Appl. No. 16/979,471, 3 pages.
Office Action Dated Apr. 27, 2023 for Eurasian Patent Application No. 202091984, a foreign counterpart to U.S. Appl. No. 16/979,475, 3 pages.
Office Action Dated Mar. 9, 2023, for European patent application No. 19767433.6, a foreign counterpart of U.S. Appl. No. 16/979,475, 5 pages.
Liu, et al., "Systematic comparison of 2A peptides for cloning multi-genes in a polycistronic vector", Scientific Reports, 7:2193, May 19, 2017, 9 pages.
Brown, et al., "Bioactivity and Safety of IL13RALPHA2-Redirected Chimeric Antigen Receptor CD8+ T Cells in Patients with Recurrent Glioblastoma," Clinical Cancer Research, vol. 21, No. 18, 2015, pp. 4062-4072.

(Continued)

*Primary Examiner* — Zachary C Howard

(74) *Attorney, Agent, or Firm* — Lee & Hayes, P.C.

(57) ABSTRACT

Some embodiments of the methods and compositions provided herein relate to chimeric antigen receptors (CARs) that specifically bind to human extracellular domains of the IL-13 alpha 2 (IL13Ra2) receptor, cells containing such CARs, and methods of cell-based immunotherapy targeting cancer cells, such as cells of solid tumors.

16 Claims, 11 Drawing Sheets

Specification includes a Sequence Listing.

(56) References Cited

OTHER PUBLICATIONS

Brown, et al., "Optimization of IL13RALPHA2-Targeted Chimeric Antigen Receptor T Cells for Improved Anti-tumor Efficacy against Glioblastoma," Molecular Therapy, vol. 26, No. 1, 2018, pp. 31-44.
Brown, et al., "Regression of Glioblastoma after Chimeric Antigen Receptor T-Cell Therapy," The New England Journal of Medicine, vol. 375, No. 26, 2016, pp. 2561-2569.
Debinski, et al., "New Agents for Targeting of IL-13RA2 Expressed in Primary Human and Canine Brain Tumors," PLoS One, vol. 8, No. 10, 15 pages.
Hudecek, et al., "Receptor affinity and extracellular domain modifications affect tumor recognition by ROR1-specific chimeric antigen receptor T cells," Clinical Cancer Research, vol. 19, No. 12, 2013, pp. 3153-3164.
Kahlon, et al., "Specific Recognition and Killing of Glioblastoma Multiforme by Interleukin 13-Zetakine Redirected Cytolytic T Cells," Cancer Research, vol. 64, No. 24, 2004, pp. 9160-9166.
Office Action Dated Jan. 18, 2021 for Mexican Application No. MX/a/2020/009463, 3 pages.
Papageorgis, et al., "Targeting IL13Ralpha2 activates STAT6-TP63 pathway to suppress breast cancer lung metastasis," Breast Cancer Research, vol. 17, No. 98, 2015, 15 pages.
PCT Search Report & Written Opinion for Application No. PCT/US2019/021823, mailed May 17, 2019, 9 pages.
PCT Search Report & Written Opinion for Application No. PCT/US2019/021833, mailed Jun. 10, 2019, 9 pages.
Sengupta, et al., "Interleukin-13 Receptor Alpha 2-Targeted Glioblastoma Immunotherapy," BioMed Research International, vol. 2014, No. 952128, 2014, 8 pages.
Tu, et al., "IL-13 receptor ALPHA2 stimulates human glioma cell growth and metastasis through the Src/PI3K/Akt/mTOR signaling pathway," Tumor Biology, vol. 37, 2016, pp. 14701-14709.
Brown, et al, "Regression of Glioblastoma after Chimeric Antigen Receptor T-Cell Therapy", New England Journal of Medicine, vol. 375, No. 26, Dec. 29, 2016, pp. 2561-2569.
Extended European Search Report Dated Nov. 24, 2021 for European Application No. 19768040.8, 11 pages.
Extended European Search Report Dated Dec. 7, 2021 for European Patent Application No. 19767433.6, 9 pages.
Hedge, et al., "Tandem CAR T cells targeting HER2 and IL13Ra2 mitigate tumor antigen escape," The Journal of Clinical Investigation, vol. 126, No. 8, 2016, pp. 3036-3052.
Kacherovsky, et al., "Multiplexed Gene Transfer to a Human T-Cell Line by Combining Sleeping Beauty Transposon System with Methotrexate Selection", Biotechnology and Bioengineering, vol. 112, No. 7, 2015, pp. 1429-1436.
Krenciute, et al., "Characterization and Functional Analysis of scFv-based Chimeric Antigen Receptors to Redirect T Cells to IL 13Ra2-positive Glioma," Molecular Therapy, vol. 24, No. 2, 2016, pp. 354-363.
Migliorini, et al., "CAR T-Cell Therapies in Glioblastoma: A First Look," Clinical Cancer Research, vol. 24, No. 3, 2017, 7 pages.
Pituch, et al., "Neural stem cells secreting bispecific T cell engager to induce selective antiglioma activity," PNAS, vol. 118, No. 9, 2021, 11 pages.
Eurasian Office Action mailed Nov. 14, 2022 for Eurasian Patent Application No. 202091984, a foreign counterpart to U.S. Appl. No. 16/979,475, 5 pages.
Paszkiewicz, "Development of a truncated EGFR marker as a safeguard for adoptive T cell therapy", Jun. 16, 2014, 192 pages.
Wang, et al, "Engineered IL13 variants direct specificity of IL13Ra2-targeted CAR T cell therapy", Jun. 15, 2016, 12 pages.
International Search Report for PCT/US2019/021823 dated May 17, 2019.
Australian Office Action mailed Aug. 24, 2023 for Australian Patent Application No. 2019234580, a foreign counterpart to U.S. Appl. No. 16/979,475, 3 pages.
Japanese Office Action mailed Jul. 25, 2023 for Japanese Patent Application No. 2020-548920, a foreign counterpart to U.S. Appl. No. 16/979,471, 7 pages.
Hashimoto, "Immunotherapy for Central Nervous System Tumors," J. Kyoto Pref. Univ. Med., 2017, vol. 126, pp. 405-415.
Jonnalagadda, et al., "Efficient selection of genetically modified human T cells using methotrexate-resistant human dihydrofolate reductase," Gene Ther., vol. 20, No. 8, 2013, pp. 853-860.
Office Action Dated Jan. 17, 2023 for Japanese Patent Application No. 2020-548920, 11 pages.
Office Action Dated Jan. 31, 2023 for Japanese Patent Application No. 2020-549002, 5 pages.
Office Action for European Application No. 19767433.6, Dated May 23, 2024, 5 pages.
Office Action for U.S. Appl. No. 16/979,475, Dated Jun. 21, 2024, 8 Pages.
Office Action for Israeli Application No. 277268, Dated Apr. 2, 2024, 10 pages.
Office Action for Korean Application No. 10-2020-7028966, Dated May 7, 2024, 9 pages.
Office Action for U.S. Appl. No. 16/979,475, Dated Feb. 29, 2024, 7 pages.

\* cited by examiner

NUCLEIC ACIDS ENCODING IL-13 RECEPTOR ALPHA 2 (IL13Ra2) CHIMERIC ANTIGEN RECEPTOR FOR TUMOR SPECIFIC T CELL IMMUNOTHERAPY

CROSS-REFERENCE TO RELATED APPLICATIONS

This application is a U.S. National Phase Application of PCT International Application Number PCT/US2019/021823, filed on Mar. 12, 2019, designating the United States of America and published in the English language, which is an International Application of and claims the benefit of priority to U.S. Provisional Application No. 62/643,055, filed on Mar. 14, 2018. The disclosures of the above-referenced applications are hereby expressly incorporated by reference in their entireties.

REFERENCE TO SEQUENCE LISTING

The present application is being filed along with a Sequence Listing in electronic format. The Sequence Listing is provided as a file entitled SeqList-SCRI-169NP.txt, created Sep. 9, 2020, which is approximately 63 Kb in size. The information in the electronic format of the Sequence Listing is hereby expressly incorporated by reference in its entirety.

FIELD OF THE INVENTION

Some embodiments of the methods and compositions provided herein relate to chimeric antigen receptors (CARs) that specifically bind to human extracellular domains of an IL-13 alpha 2 (IL13Ra2) receptor, to cells containing such CARs, and to methods of cell-based immunotherapy targeting cancer cells, such as cells of solid tumors.

BACKGROUND OF THE INVENTION

Despite significant advances in the understanding of brain cancer, during the last decade, the mortality rate has remained consistent and new innovative therapies are urgently needed. To date, T cell immunotherapy has emerged as a promising cancer therapy supported by remarkable clinical data reporting complete remission in patients with B cell malignancies after administration of T cell CARs targeting CD19. However, there remains a need for further and improved T cell immunotherapies.

SUMMARY OF THE INVENTION

Some embodiments of the methods and compositions provided herein include a nucleic acid encoding a chimeric antigen receptor, the chimeric antigen receptor comprising: a ligand binding domain that binds to and/or interacts with an IL-13 alpha 2 (IL13Rα2) receptor; a polypeptide spacer between the ligand binding domain and a transmembrane domain; the transmembrane domain; and intracellular signaling region.

In some embodiments, the ligand binding domain comprises: a heavy chain complementarity determining region 1 (CDR1) having the amino acid sequence of SEQ ID NO:20, or conservative variations thereof; a heavy chain complementarity determining region 2 (CDR2) having the amino acid sequence of SEQ ID NO:21, or conservative variations thereof; and/or a heavy chain complementarity determining region 3 (CDR3) having the amino acid sequence of SEQ ID NO:22, or conservative variations thereof.

In some embodiments, the ligand binding domain comprises: a light chain complementarity determining region 1 (CDR1) having the amino acid sequence of SEQ ID NO:23, or conservative variations thereof; a light chain complementarity determining region 2 (CDR2) having the amino acid sequence of SEQ ID NO:24, or conservative variations thereof; and/or a light chain complementarity determining region 3 (CDR3) having the amino acid sequence of SEQ ID NO:25, or conservative variations thereof.

In some embodiments, the ligand binding domain comprises a heavy chain variable (VH) domain comprising a polypeptide having at least 90% identity with the amino acid sequence of SEQ ID NO:18.

In some embodiments, the ligand binding domain comprises a light chain variable (VL) domain comprising a polypeptide having at least 90% identity with the amino acid sequence of SEQ ID NO:19.

In some embodiments, wherein the ligand binding domain comprises: a heavy chain CDR1 having the amino acid sequence of SEQ ID NO:20; a heavy chain CDR2 having the amino acid sequence of SEQ ID NO:21; and/or a heavy chain CDR3 having the amino acid sequence of SEQ ID NO:22.

In some embodiments, the ligand binding domain comprises: a light chain CDR1 having the amino acid sequence of SEQ ID NO:23; a light chain CDR2 having the amino acid sequence of SEQ ID NO:24; and/or a light chain CDR3 having the amino acid sequence of SEQ ID NO:25.

In some embodiments, the ligand binding domain comprises a VH domain comprising a polypeptide having the amino acid sequence of SEQ ID NO:18.

In some embodiments, the ligand binding domain comprises a VL domain having the amino acid sequence of SEQ ID NO:19.

In some embodiments, the ligand binding domain is an antibody fragment, such as an antigen-binding fragment.

In some embodiments, the ligand binding domain is a single chain variable fragment (scFv). In some embodiments, the scFv comprises a VL-VH orientation. In some embodiments, the single chain variable fragment (scFv) comprises a sequence having at least 95% identity with the nucleotide sequence of SEQ ID NO:61. In some embodiments, the single chain variable fragment (scFv) comprises the nucleotide sequence of SEQ ID NO:61.

In some embodiments, the spacer comprises an amino acid sequence of $X_1PPX_2P$.

In some embodiments, the spacer region comprises a portion of a hinge region of a human antibody or modified variant thereof.

In some embodiments, the spacer is 15 amino acids or less but not less than 1 or 2 amino acids.

In some embodiments, the spacer comprises, consists, or consists essentially of a sequence having at least 95% identity with the amino acid sequence of SEQ ID NO:09. In some embodiments, the spacer comprises, consists, or consists essentially of an amino acid sequence of SEQ ID NO:09, or conservative substitutions thereof.

In some embodiments, the spacer comprises, consists of, or consists essentially of, an IgG4 hinge spacer (S).

In some embodiments, the spacer comprises, consists of, or consists essentially of, an IgG4 hinge-CH3 spacer (M).

In some embodiments, the spacer comprises, consists of, or consists essentially of, an IgG4 hinge-CH2 (L234D, N297A)-CHE spacer (L).

In some embodiments, the intracellular signaling region comprises primary and a costimulatory signaling domains, optionally comprising all or a portion of a CD3 zeta in combination with a co-stimulatory domain selected from the group consisting of signaling domains of CD27, CD28, 4-1BB, OX-40, CD30, CD40, PD-1, ICOS, LFA-1, CD2, CD7, NKG2C, and B7-H3 and combinations thereof.

In some embodiments, the intracellular signaling region comprises a signaling portion of a CD3 zeta and a signaling portion of a 4-1BB.

In some embodiments, the transmembrane domain comprises a CD28 transmembrane domain (CD28tm).

Some embodiments also include a nucleic acid that encodes a marker sequence. In some embodiments, the marker sequence is a truncated receptor and optionally is an EGFRt, a HER2t, or a CD19t.

Some embodiments also include a dihydrofolate reductase transgene configured for methotrexate selection. In some embodiments, the dihydrofolate reductase transgene is a dihydrofolate reductase double mutant (DHFRdm). In some embodiments, the dihydrofolate reductase double mutant comprises amino acid mutations of L22F and F31S.

Some embodiments of the methods and compositions provided herein include an expression vector comprising the nucleic acid of any one of the embodiments provided herein. In some embodiments, the vector is a viral vector. In some embodiments, the vector is a lentiviral or adenoviral vector.

Some embodiments of the methods and compositions provided herein include a chimeric antigen receptor (CAR) polypeptide encoded by the nucleic acid of any one of the embodiments provided herein.

Some embodiments of the methods and compositions provided herein include a host cell comprising the nucleic acid of any one of the embodiments provided herein.

In some embodiments, the host cell is a CD8+ T cytotoxic lymphocyte cell selected from the group consisting of naïve CD8+ T cells, central memory CD8+ T cells, effector memory CD8+ T cells and bulk CD8+ T cells. In some embodiments, the CD8+ cytotoxic T lymphocyte cell is a central memory T cell and, wherein the central memory T cell is positive for CD45RO+, CD62L+, and CD8+.

In some embodiments, the host cell is a CD4+T helper lymphocyte cell selected from the group consisting of naïve CD4+ T cells, central memory CD4+ T cells, effector memory CD4+ T cells, and bulk CD4+ T cells. In some embodiments, the CD4+ helper lymphocyte cell is a naïve CD4+ T cell and, wherein the naïve CD4+ T cell is positive for CD45RA+, CD62L+ and CD4+ and negative for CD45RO.

In some embodiments, the host cell is a precursor T cell.

In some embodiments, the host cell is a hematopoietic stem cell.

Some embodiments of the methods and compositions provided herein include a pharmaceutical composition comprising the host cell of any one of the embodiments provided herein, and a pharmaceutically acceptable excipient.

Some embodiments of the methods and compositions provided herein include a method for preparing the host cell of any one of the embodiments provided herein, comprising: introducing the nucleic acid of any one of the embodiments provided herein into a cell; culturing the cell in the presence of anti-CD3 antibody and/or anti CD28 antibody, and at least one homeostatic cytokine in conditions sufficient for the cells to expand; and selecting the cell with a selection reagent; wherein the selection reagent is configured to selectively enrich cells transduced with the nucleic acid or vector.

In some embodiments, the cell is a lymphocyte. In some embodiments, the lymphocyte has a CD45RA−, CD45RO+, and CD62L+ phenotype. In some embodiments, the lymphocyte is CD8+ or CD4+.

In some embodiments, the selection reagent is methotrexate.

In some embodiments, the cytokine is IL-15, IL-7 and/or IL-21.

Some embodiments also include introducing a second nucleic acid into the host cell, wherein the second nucleic acid encodes a marker protein. In some embodiments, the marker protein is EGFRt.

Some embodiments of the methods and compositions provided herein include a host cell of any one of the embodiments provided herein for use in a medicament or for use in the treatment or inhibition of a cancer or a solid tumor expressing an IL-13α2 receptor. In some embodiments, the cancer comprises a brain cancer. In some embodiments, the cancer is a glioma or glioblastoma tumor. In some embodiments, the cancer is glioblastoma multiforme (GBM). In some embodiments, the cancer is a glioma.

Some embodiments of the methods and compositions provided herein include a method of treating, inhibiting, or ameliorating a cancer in a subject, comprising: administering the host cell of any one of the embodiments provided herein to the subject in need thereof. In some embodiments, the cancer is a IL13Rα-positive malignancy. In some embodiments, the cancer is brain cancer. In some embodiments, the cancer is a glioma or glioblastoma tumor. In some embodiments, the cancer is a glioma. In some embodiments, the cancer is glioblastoma multiforme (GBM). In some embodiments, the subject is mammalian. In some embodiments, the subject is human.

Some embodiments also include administering an additional therapy selected from chemotherapy and radiation therapy. In some embodiments, the chemotherapeutic drug comprises electochemotherapy, alkylating agent, antimetabolite (for example, 5-fluorouracil (5-FU), 6-mercaptopurine (6-MP), Capecitabine (Xeloda®), Cladribine, Clofarabine, Cytarabine (Ara-C®), Floxuridine, Fludarabine, Gemcitabine (Gemzar®), Hydroxyurea, Methotrexate, Pemetrexed (Alimta®), Pentostatin, and Thioguanine), anti-tumor antibiotic, topoisomerase inhibitor, mitotic inhibitor, corticosteroid, DNA intercalating agent, or checkpoint inhibitor (checkpoint kinase CHK1, CHK2).

DETAILED DESCRIPTION

Figure 1:
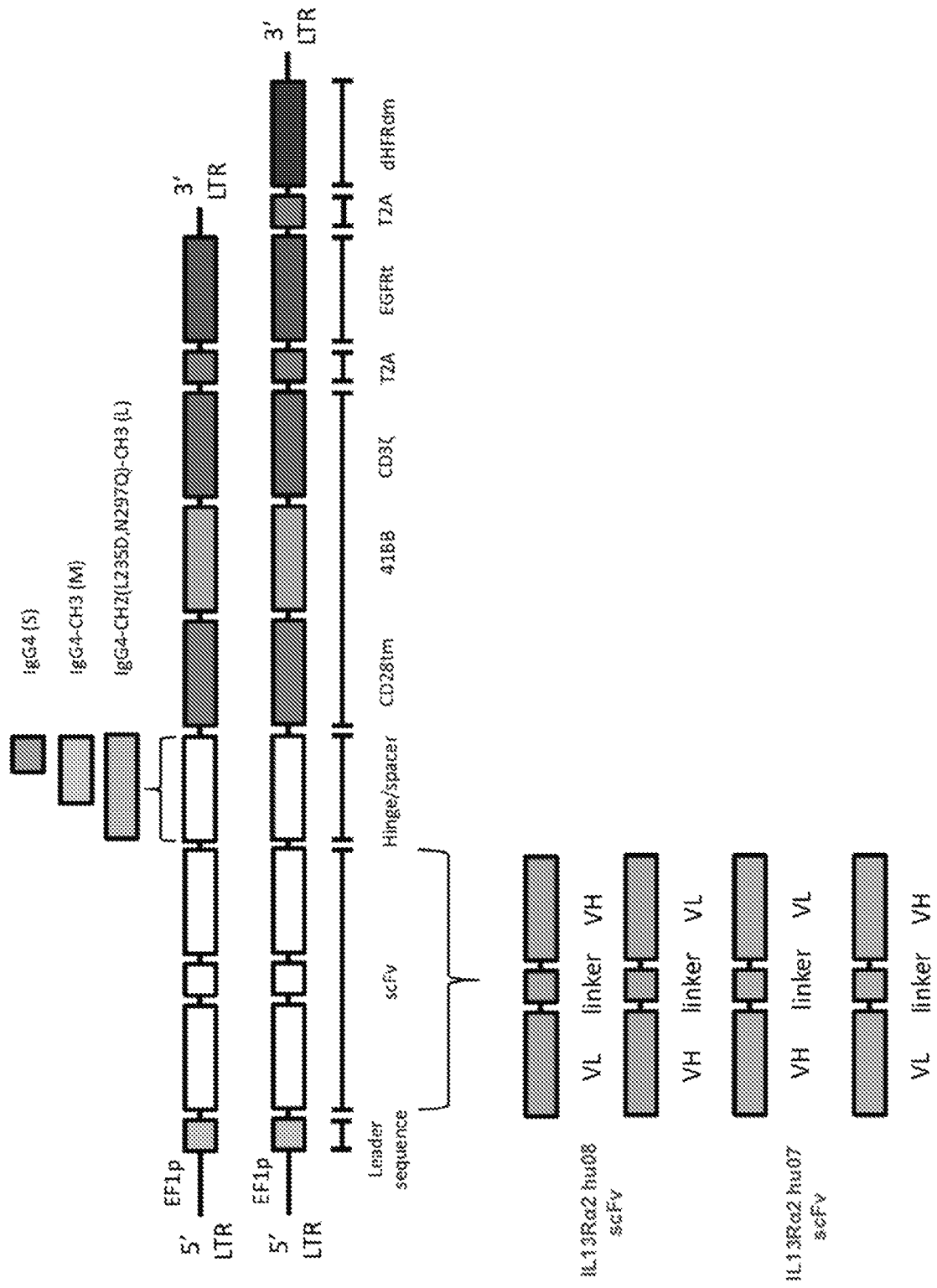
FIG. 1 depicts a schematic of certain embodiments of IL-13Rα2-targeting CARs, and components used for the construction of embodiments the IL-13Rα2-targeting CARs. IL-13Rα2 specific CARs included: one of a number of single-chain variable fragments (scFv) that specifically recognize an extracellular epitope of IL-13 alpha 2 receptor (IL-13Rα2) derived from one of two antibodies 'hu08' (Ab01) or 'hu07' (Ab02) and included a VH and VL domains with a linker therebetween; one of various spacer domains (marked "S", "M" and "L"); a transmembrane domain derived from a human CD28 (CD28tm); a costimulatory domain derived from human 4-1BB; a CD3ζ-derived signaling domain; a T2A ribosomal skip sequence; and a truncated EGFR (EGFRt) transduction marker; and optionally a further T2A ribosomal skip sequence and a dihydrofolate reductase double mutant (DHFRdm) transgene configured for methotrexate selection.

Some embodiments of the methods and compositions provided herein include IL13Ra2-targeted chimeric antigen receptors (CARs), such as second-generation IL-13Rα2-specific CARs, cells containing such CARs, nucleic acids encoding such CARs, and related therapeutic methods and uses thereof. Among the provided CARs are those having particular combinations of components or domains, such as those resulting from optimization of CAR function. In some aspects, the IL13Ra2 CAR-targeted T cell therapeutics can also act as an alternative or supplement to current IL-13Rα2-specific and unspecific cancer treatments, such as combination therapies.

IL-13Rα2 was previously found to be abundant in metastatic or late-stage BLBC (Papageorgis et al. Breast Cancer Research, 2015; 17 (1); herein expressly incorporated by reference in its entirety). Based on publicly available data, correlations were made between, likelihood of progression-free survival based and high levels of IL-13Rα2. A subtype of BLBC that tended to spread to the lungs quickly was observed to have high IL-13Rα2 levels. IL-13Rα2 was also found to stimulate human glioma cell growth and metastasis through the Src/PI3K/Akt/mTOR signaling pathway. (Tu et al. Tumour Biol. 2016 November; 37(11):14701-14709; herein expressly incorporated by reference in its entirety). IL13Ra2 targeted therapies, such as chimeric receptor-based therapies, have been described (see, e.g., Brown et al Clin Cancer Res 2015; Brown et al N Engl J Med 2016; Brown et al Mol Ther 2017; WO 2014072888-A1, describing anti-IL-13 receptor alpha 2 (IL-13-Ra2) antibodies and antibody-drug conjugates for the treatment of cancer, each herein expressly incorporated by reference in their entirety). Among such therapies are those based on or including mutant IL13 (e.g., E13Y)-based binding or antigen recognition domains, such as zetakines.

In some embodiments, the provided CARs and associated methods and uses are based in part on observations described herein showing particularly advantageous activity and/or in vivo anti-cancer effects in the context of glioblastoma or model thereof, of CARs containing specific binding domains in combination with specific other components such as specific spacer domains curative. In some aspects, the provided compositions, methods and uses are employed in the treatment, inhibition, or prevention of glioblastoma and/or other IL-13Rα2-positive malignancies. In some aspects, the provided CARs described herein differ from other CARs in various respects, such as in one or more characteristics of their molecular structure, such as the IL-13Rα2 epitope specifically recognized by the binding domain and targeted by CARs provided herein.

The provided embodiments are based in part on observations herein, such as those demonstrated in preclinical studies described herein, demonstrating antitumor in vitro activity of provided CAR-T cells, against glioblastoma cell lines and the ability to reduce tumor growth in xenograft models, in some respects to a greater extent as compared with different CARs having different molecular structures. In light of these findings, the commercial use of compositions comprising these CARs in immunotherapy for brain tumors and other IL-13Rα2-positive types of cancer is contemplated.

Definitions

As used herein, "nucleic acid" or "nucleic acid molecule" have their plain and ordinary meaning when read in light of the specification, and may include but is not limited to, for example, polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also includes so-called "peptide nucleic acids," which comprise naturally-occurring or modified nucleic acid bases attached to a polyamide backbone. Nucleic acids can be either single stranded or double stranded. In some alternatives, a nucleic acid sequence encoding a protein is provided. In some alternatives, the nucleic acid is RNA or DNA.

As used herein, "chimeric antigen receptor" has its plain and ordinary meaning when read in light of the specification, and may include but is not limited to, for example, a synthetically designed receptor comprising a ligand binding domain of an antibody or other protein sequence that binds to a molecule associated with the disease or disorder and is linked via a spacer domain to one or more intracellular signaling domains of a cell, such as a T cell, or other receptors, such as a costimulatory domain. Chimeric receptor can also be referred to as artificial cell receptors or T cell receptors, chimeric cell receptors or T cell receptors, chimeric immunoreceptors, and/or chimeric antigen receptors (CARs). These receptors can be used to graft the specificity of a monoclonal antibody or binding fragment thereof onto a cell, preferably a T-cell with transfer of their coding sequence facilitated by viral vectors, such as a retroviral vector or a lentiviral vector. CARs can be, in some instances, genetically engineered T cell receptors designed to redirect T cells to target cells that express specific cell-surface antigens. T cells can be removed from a subject and modified so that they can express receptors that can be specific for an antigen by a process called adoptive cell transfer. The T cells are reintroduced into the patient where they can then recognize and target an antigen. CARs are also engineered receptors that can graft an arbitrary specificity onto an immune receptor cell. The term chimeric antigen receptors or "CARs" are considered by some investigators to include the antibody or antibody fragment, preferably an antigen binding fragment of an antibody, the spacer, signaling domain, and transmembrane region. Due to the surprising effects of modifying the different components or domains of the CAR described herein, such as the epitope binding region (for example, antibody fragment, scFv, or portion thereof), spacer, transmembrane domain, and/or signaling domain), the components of the CAR are frequently distinguished throughout this disclosure in terms of independent elements. The variation of the different elements of the CAR can, for example, lead to stronger binding affinity for a specific epitope or antigen.

The CARs graft the specificity of a monoclonal antibody or binding fragment thereof or scFv onto a T cell, with the transfer of their coding sequence facilitated by vectors. In order to use CARs as a therapy for a subject in need, a technique called adoptive cell transfer is used in which T cells are removed from a subject and modified so that they can express the CARs that are specific for an antigen. The T cells, which can then recognize and target an antigen, are reintroduced into the patient.

In some embodiments, the transmembrane domain is a region of a membrane-spanning protein that is hydrophobic that can reside in the bilayer of a cell to anchor a protein that is embedded to the biological membrane. Without being limiting, the topology of the transmembrane domain can be a transmembrane alpha helix. In some alternatives of the chimeric antigen receptor, the chimeric antigen receptor comprises a sequence encoding a transmembrane domain. In some alternatives, the transmembrane domain comprises a CD28 transmembrane sequence or a fragment thereof that is a length of 10, 11, 12, 13, 14, 15, 16, 17, 18, 19, 20, 21, 22, 23, 24, 25, 26, 27, or 28 amino acids or a length within a range defined by any two of the aforementioned lengths. In some alternatives, the CD28 transmembrane sequence or fragment thereof comprise 28 amino acids in length.

In some embodiments, the signaling domains, such as primary signaling domains or costimulatory domains, include an intracellular or cytoplasmic domain of a protein or a receptor protein that interacts with components within the interior of the cells and is capable of relaying or participating in the relaying of a signal. Such interactions in some aspects can occur through the intracellular domain communicating via specific protein-protein or protein-ligand interactions with an effector molecule or an effector protein, which in turn can send the signal along a signal chain to its destination. In some embodiments, the signaling domain includes a co-stimulatory domain. In some aspects, the costimulatory domain includes a signaling moiety that provides to T-cells a signal which, in addition to the primary signal provided by for instance the CD3 zeta chain of the TCR/CD3 complex, enhances response such as a T-cell effector response, such as, for example, an immune response, activation, proliferation, differentiation, cytokine secretion, cytolytic activity, perform and/or granzyme activity and the like. In some embodiments, the intracellular signaling domain and/or the co-stimulatory domain can include all or a portion of CD27, CD28, 4-1BB, OX40, CD30, CD40, ICOS, lymphocyte function-associated antigen-1 (LFA-1), CD2, CD7, LIGHT, NKG2C, and/or B7-H3, and/or a ligand that specifically binds with CD83.

As used herein, an "antibody" has its plain and ordinary meaning when read in light of the specification, and may include but is not limited to, for example, a large Y-shape protein produced by plasma cells that is used by the immune system to identify and neutralize foreign objects such as bacteria and viruses. In some contexts, the term antibody refers to antigen binding fragments of an antibody. The antibody protein can comprise four polypeptide chains; two identical heavy chains and two identical light chains connected by disulfide bonds. Each chain is composed of structural domains called immunoglobulin domains. These domains can contain 70-110 amino acids and are classified into different categories according to their size and function. A chimeric antigen receptor can comprise a ligand binding domain, which includes an antibody fragment, preferably an antigen binding fragment. In some alternatives, a nucleic acid encoding a chimeric antigen receptor (CAR) is provided, the nucleic acid comprising: a) a first polynucleotide encoding a ligand binding domain, wherein the ligand binding domain binds to and/or interacts with an IL-13 alpha 2 (IL13Rα2) receptor, b) a second polynucleotide encoding a polypeptide spacer of a length sufficient to allow the ligand binding domain to interact with the IL-13 alpha 2 (IL13Rα2) receptor, c) a third polynucleotide encoding a transmembrane domain and d) a fourth polynucleotide encoding an intracellular signaling domain. In some alternatives, the ligand binding domain is an antibody fragment.

As used herein, a "single chain variable fragment" or scFv has its plain and ordinary meaning when read in light of the specification, and may include but is not limited to, for example, a fusion protein that comprises the variable regions of the heavy chain (VH) and the light chains (VL) of an immunoglobulin, which are connected to one another with a short linker peptide. Without being limiting, the linker can comprise glycine for flexibility and hydrophilic amino acids, for example serine or threonine for solubility. The linker can connect the N-terminus of the VH with the C-terminus of the VL or it can connect the C-terminus of the VH with the N-terminus of the VL. In some alternatives, the ligand binding domain present on a CAR is a single chain variable fragment (scFv). In some alternatives, the scFv domain present on a CAR is specific for a IL-13 alpha 2 (IL13Rα2) receptor present on a tumor cell.

In some embodiments, the compositions, cells and vectors include marker sequences or nucleic acids encoding the same, which may include, for example, a protein that serves as a label for a cell. In some alternatives of the cells described herein, the cells co-express a marker protein for a specific chimeric antigen protein that is expressed. In some alternatives of the cells provided herein, the chimeric antigen receptor is co-expressed with a specific marker protein. In some alternatives of the cells provided herein, the cells comprise a nucleic acid encoding a chimeric antigen receptor. Markers may include selectable marker sequence, such as a gene introduced into a vector or a cell that confers a trait for artificial selection. A selectable marker sequence or marker sequence can be a screenable marker to allow a researcher to distinguish between wanted and unwanted cells, or to enrich for a specific cell type. In some alternatives, a vector is provided wherein the vector encodes a chimeric antigen receptor comprising a marker sequence, wherein said marker sequence encodes a cell surface selectable marker. In the alternatives described herein, the fusion protein provided can comprise a marker sequence that can be selected in experiments, such as flow cytometry. In some alternatives, the marker is the protein Her2tG or EGFRt.

Methotrexate (MTX) may include but is not limited to, for example, an antimetabolite and antifolate drug. In some aspects, it acts by inhibiting the metabolism of folic acid. In some alternatives, a method of generating engineered multiplexed T cells for adoptive T cell immunotherapy is provided. In the broadest sense, the method can comprise providing the gene delivery polynucleotide of any of the alternatives described herein, selecting the cells comprising the gene delivery polynucleotide, wherein the selecting comprises adding a selection reagent. In some alternatives described herein, the selection reagent comprises an agent for selection. In some alternatives, the selection reagent is MTX.

As used herein, "dihydrofolate reductase", or DHFR, as described herein, has its plain and ordinary meaning when read in light of the specification, and may include but is not limited to, for example, an enzyme that reduces dihydrofolic acid to tetrahydrofolic acid, using NADPH as electron donor, which can be converted to the kinds of tetrahydrofolate cofactors used in 1-carbon transfer chemistry. In some alternatives described herein, a gene delivery polynucleotide is provided. In some alternatives, the gene delivery polynucleotide comprises at least one selectable marker cassette encoding for a double mutant of dihydrofolate reductase (DHFRdm).

In some embodiments, the constructs and sequences provided are modified or optimized, such as by codon optimization, which may include but is not limited to, for example, the design process of altering codons to codons known to increase maximum protein expression efficiency in a desired cell, preferably in a human cell. In some alternatives, codon optimization is described, wherein codon optimization can be performed by using algorithms that are known to those skilled in the art to create synthetic genetic transcripts optimized for high protein yield. Programs containing alogorithms for codon optimization are known to those skilled in the art. Programs can include, for example, OptimumGene™, GeneGPS® algorithms. Additionally, synthetic codon optimized sequences can be obtained commercially for example from Integrated DNA Technologies and other commercially available DNA sequencing services. In some alternatives, the nucleic acids are described, wherein the genes of the nucleic acid for the complete gene transcript are codon optimized for expression in humans. In some alternatives, the genes are optimized to have selected codons specifically for maximal protein expression in human cells, which can increase the concentration of proteins or CARs of a T cell.

Codon optimization can be performed to reduce the occurrence of secondary structure in a polynucleotide, as well. In some alternatives, codon optimization can also be performed to reduce the total GC/AT ratio. Strict codon optimization can also lead to unwanted secondary structure or an undesirable GC content that leads to secondary structure. As such the secondary structures affect transcriptional efficiency. Programs such as GeneOptimizer can be used after codon usage optimization, for secondary structure avoidance and GC content optimization. These additional programs can be used for further optimization and troubleshooting after an initial codon optimization to limit secondary structures that may occur after the first round of optimization. Alternative programs for optimization are known to those skilled in the art. In some alternatives, the nucleic acid comprises sequences that are codon optimized for expression in humans and/or to remove secondary structure and/or to reduce the total GC/AT ratio. In some alternatives, the sequences are optimized for secondary structure avoidance. In some alternatives, the sequences are optimized to reduce the total GC/AT ratio.

As used herein, "vector," "expression vector" or "construct" has its plain and ordinary meaning when read in light of the specification, and may include but is not limited to, for example, a nucleic acid used to introduce heterologous nucleic acids into a cell that has regulatory elements to provide expression of the heterologous nucleic acids in the cell. Vectors include but are not limited to plasmid, minicircles, yeast, and viral genomes. In some alternatives, the vectors are plasmid, minicircles, or viral genomes. In some alternatives, the vector is a viral vector. In some alternatives, the viral vector is a lentivirus. In some alternatives, the vector is a lentiviral vector. In some alternatives, the vector is a foamy viral vector, adenoviral vectors, retroviral vectors or lentiviral vectors.

T cells or T lymphocytes in some embodiments may include T cells from any mammalian, preferably primate, species, including monkeys, dogs, and humans. In some alternatives the T cells are allogeneic (from the same species but different donor) as the recipient subject who receives or is to receive the cells, such as in the form of a therapeutic composition; in some alternatives the T cells are autologous (the donor and the recipient are the same); in some alternatives the T cells arc syngeneic (the donor and the recipients are different but are identical twins).

As used herein, a "ribosome skip sequence" as described herein refers to a sequence that during translation, forces the ribosome to "skip" the ribosome skip sequence and translate the region after the ribosome skip sequence without formation of a peptide bond. Several viruses, for example, have ribosome skip sequences that allow sequential translation of several proteins on a single nucleic acid without having the proteins linked via a peptide bond. As described herein, this is the "linker" sequence. In some alternatives of the nucleic acids provided herein, the nucleic acids comprise a ribosome skip sequence between the sequence for the chimeric antigen receptor and the sequence of the marker protein, such that the proteins are co-expressed and not linked by a peptide bond. In some alternatives, the ribosome skip sequence is a P2A, T2A, E2A or F2A sequence. In some alternatives, the ribosome skip sequence is a T2A sequence.

Mature T cells express the surface protein CD4 and are referred to as CD4+ T cells. CD4+ T cells are generally treated as having a pre-defined role as helper T cells within the immune system. For example, when an antigen-presenting cell expresses an antigen on MHC class II, a CD4+ cell will aid those cells through a combination of cell to cell interactions (e.g. CD40 and CD40L) and through cytokines. Nevertheless, there are rare exceptions; for example, subgroups of regulatory T cells, natural killer cells, and cytotoxic T cells express CD4. All of the latter CD4+ expressing T cell groups are not considered T helper cells.

As used herein, "central memory" T cell (or "TcM") has its plain and ordinary meaning when read in light of the specification, and may include but is not limited to, for example, an antigen experienced CTL that expresses CD62L or CCR-7 and CD45RO on the surface thereof, and does not express or has decreased expression of CD45RA as compared to naïve cells. In some alternatives, central memory cells are positive for expression of CD62L, CCR7, CD28, CD127, CD45RO, and/or CD95, and have decreased expression of CD54RA as compared to naïve cells.

As used herein, "effector" "$T_E$" T cells has its plain and ordinary meaning when read in light of the specification, and may include but is not limited to, for example, antigen experienced cytotoxic T lymphocyte cells that do not express or have decreased expression of CD62L, CCR7, or CD28, or are positive for granzyme B and/or perforin, as compared to central memory or naïve T cells.

As used herein, "pharmaceutical excipient," or pharmaceutical vehicle has its plain and ordinary meaning when read in light of the specification, and may include but is not limited to, for example, a carrier or inert medium used as a solvent in which the medicinally active agent or T cells for treatment or therapy is formulated and or administered. Vehicles can include polymeric micelles, liposomes, lipoprotein-based carriers, nano-particle carriers, dendrimers, and/or other vehicles for T cells that are known to one skilled in the art. An ideal vehicle or excipient can be non-toxic, biocompatible, non-immunogenic, biodegradable, and can avoid recognition by the host's defense mechanisms.

As used herein, "T cell precursors" has its plain and ordinary meaning when read in light of the specification, and may include but is not limited to, for example, lymphoid precursor cells that can migrate to the thymus and become T cell precursors, which do not express a T cell receptor. All T cells originate from hematopoietic stem cells in the bone marrow. Hematopoietic progenitors (lymphoid progenitor cells) from hematopoietic stem cells populate the thymus and expand by cell division to generate a large population of immature thymocytes. The earliest thymocytes express neither CD4 nor CD8 and are therefore classed as double-negative ($CD4^-CD8^-$) cells. As they progress through their development, they become double-positive thymocytes ($CD4^+CD8^+$), and finally mature to single-positive ($CD4^+CD8^-$ or $CD4^-CD8^+$) thymocytes that are then released from the thymus to peripheral tissues.

Glioblastoma multiforme (GBM), generally is considered the most aggressive cancer that begins within the brain. Initial signs and symptoms of glioblastoma generally are non-specific. They may include headaches, personality changes, nausea, and symptoms similar to those of a stroke.

As used herein, a "leader sequence" also known as the "5' untranslated region (5' UTR), is the region of mRNA that is located upstream from the initiation codon and is important in regulating the translation of an mRNA transcript. In some alternatives of the method of making genetically modified T cells, which have a chimeric antigen receptor (CAR), the vector encoding the chimeric antigen receptor comprises a sequence encoding a leader sequence.

As described in the alternatives herein are ligands. "Ligand" has its plain and ordinary meaning when read in light of the specification, and may include but is not limited to, for example, a substance that can form a complex with a biomolecule. By way of example and not of limitation, ligands can include substrates, proteins, small molecules, inhibitors, activators, nucleic acids or neurotransmitters. Binding can occur through intermolecular forces, for example ionic bonds, hydrogen bonds, or van der walls interactions. Ligand binding to a receptor protein can alter the three-dimensional structure and determine its functional state. The strength of binding of a ligand is referred to as the binding affinity and can be determined by direct interactions and solvent effects. A ligand can be bound by a "ligand binding domain." A ligand binding domain, for example, can refer to a conserved sequence in a structure that can bind a specific ligand or a specific epitope on a protein. The ligand binding domain or ligand binding portion can comprise an antibody or binding fragment thereof or scFv, a receptor ligand or mutants thereof, peptide, and/or polypeptide affinity molecule or binding partner. Without being limiting, a ligand binding domain can be a specific protein domain or an epitope on a protein that is specific for a ligand or ligands.

As described in the alternatives herein, is the interleukin 13 receptor subunit alpha-2 (IL-13Ra2). "Interleukin-13 receptor subunit alpha-2 (IL-13Rα2)", also known as CD213A2 (cluster of differentiation 213A2), has its plain and ordinary meaning when read in light of the specification, and may include but is not limited to, for example, a membrane bound protein that in humans is encoded by the IL-13RA2 gene. IL-13Rα2 is closely related to IL-13Rα1, a subunit of the interleukin-13 receptor complex. IL-13Rα2 generally binds IL-13 with high affinity, but lacks any significant cytoplasmic domain, and does not appear to function as a signal mediator. It is, however able to regulate the effects of both IL-13 and IL-4, despite the fact it is unable to bind directly to the latter. It is also reported to play a role in the internalization of IL-13.

In some alternatives, the peptide spacer is 15 amino acids or less but not less than 1 or 2 amino acids. In some embodiments, the spacer is a polypeptide chain. In some embodiments, the spacer is a polypeptide chain. In some aspects, the polypeptide chain may range in length, such as from 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239 or 240 amino acids or a length within a range defined by any two of the aforementioned lengths. A spacer can comprise any 20 amino acids, for example, in any order to create a desirable length of polypeptide chain in a chimeric antigen receptor, which includes the amino acids arginine, histidine, lysine, aspartic acid, glutamic acid, serine, threonine, asparagine, glutamine, cysteine, glycine, proline, alanine, valine, isoleucine, methionine, phenylalanine, tyrosine and/or tryptophan. A spacer sequence can be a linker between the scFv (or ligand binding domain) and the transmembrane domain of the chimeric antigen receptor. In some alternatives of the chimeric antigen receptor, the chimeric antigen receptor further comprises a sequence encoding a spacer. In some alternatives the spacer comprises a sequence with a length of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239 or 240 amino acids or a length within a range defined by any two of the aforementioned lengths. In some alternatives, the spacer resides between the scFv and the transmembrane region of the chimeric antigen receptor. In some alternatives, the spacer resides between the ligand binding domain of the chimeric antigen receptor and the transmembrane region of the chimeric antigen receptor.

A spacer may also be customized, selected, or optimized for a desired length so as to improve binding of scFv domain to the target cell, which may increase cytotoxic efficacy. In some alternatives, the linker or spacer between the scFv domain or ligand binding domain and the transmembrane can be 25 to 55 amino acids in length (e.g., at least, equal to 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, or 55 amino acids or a length within a range defined by any two of the aforementioned lengths).

Some embodiments include polypeptide sequences or conservative variations thereof, such as conservative substitutions in a polypeptide sequence. In some embodiments, "conservative amino acid substitution" refers to amino acid substitutions that substitute functionally-equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Several families of conservative amino acid substitutions are shown in TABLE 1.

TABLE 1

| Family | Amino Acids |
| --- | --- |
| non-polar | Trp, Phe, Met, Leu, Ile, Val, Ala, Pro |
| uncharged polar | Gly, Ser, Thr, Asn, Gln, Tyr, Cys |
| acidic/negatively charged | Asp, Glu |
| basic/positively charged | Arg, Lys, His |
| Beta-branched | Thr, Val, Ile |
| residues that influence chain orientation | Gly, Pro |
| aromatic | Trp, Tyr, Phe, His |

High levels of Interleukin 13 receptor alpha 2 (IL-13RA2) are found on a number of cancer cells including pancreatic, breast, and ovarian cancers or malignant gliomas, such as glioblastoma. IL-13RA2 has also been shown to be overexpressed in a vast majority of human patients with high-grade astrocytomas (see PLoS One. 2013 Oct. 16; 8(10): e77719; herein expressly incorporated by reference in its entirety). Additionally, previous research has shown that reducing the amount of IL13RA2 expression in cancer cells significantly slowed tumor growth in models (Breast Cancer Research, 2015; 17 (1); herein expressly incorporated by reference in its entirety). It is contemplated that few types of normal tissues express IL-13-RA2 and only at low levels.

In the case of the glioblastoma multiforme (GBM), the high expression of IL13Rα2 can be a prognostic marker of tumor progression and poor patient survival. Provided are chimeric antigen receptors (CARs), and cells and therapies containing or using the same, which selectively target IL13Rα2. The provided CARs generally comprise an extracellular domain linked to a transmembrane region and an intracellular signaling region including one or more signaling domains, generally including primary and costimulatory signaling domains.

The extracellular domain includes an antigen-binding motif, which in some aspects is or includes an antigen binding antibody fragment such as an scFv. In some aspects, the binding domain, such as the scFv, is derived from a human interleukin-13Rα2-specific antibody. In some embodiments, the CAR includes a spacer region that connects the extracellular binding domain to the transmembrane domain. In some aspects, one or more properties of the spacer are designed to optimize features of the CAR such as CAR function, for example, by providing appropriate distance between contact of the epitope and binding region and the cell membrane(s), and/or by providing flexibility. In some aspects, the spacer contains fewer or no more than 20 amino acids in length, such as fewer or no more than 15 amino acids in length, fewer or no more than 14 amino acids in length, fewer or no more than 13 amino acids in length, or no more than 12 amino acids in length. In some aspects, it contains at or about 12 or 15 amino acids in length. In some aspects, the spacer comprises all or a portion of an immunoglobulin hinge region (such as a human IgG hinge region, such as a human IgG4 hinge region) or modified version thereof.

In some alternatives, the spacer comprises a hinge region of a human antibody. In some alternatives of the method, the spacer comprises an IgG4 hinge. In some alternatives, the IgG4 hinge region is a modified IgG4 hinge. A "modified IgG4 hinge" as described herein can refer to a hinge region that can have at least 90%, 91%, 92%, 93%, 94% 95%, 96%, 97%, 98%, 99%, or 100% sequence identity or a sequence identity within a range defined by any two of the aforementioned percentages, with a hinge region amino acid sequence as set forth in SEQ ID NO:01, SEQ ID NO:02, SEQ ID NO:03, SEQ ID NO:04, SEQ ID NO:05, SEQ ID NO:06, SEQ ID NO:07, or SEQ ID NO:08.

In some alternatives, the CAR comprises an S spacer, M spacer or an L spacer. The S spacer comprises a sequence set forth in SEQ ID NO:09. The M spacer comprises a sequence set forth in SEQ ID NO:10. The L spacer comprises a sequence set forth in SEQ ID NO:11.

In some embodiments, the transmembrane portion includes or is a CD28 transmembrane domain (CD28tm) such as a human CD28 transmembrane domain. The CD28tm is encoded by a sequence set forth in SEQ ID NO:12. The CD28tm comprises the amino acids set forth in SEQ ID NO:13. In some embodiments, the transmembrane domain is linked to an intracellular signaling region containing one or more costimulatory domains, such as a costimulatory domain derived from intracellular segment of human 4-1BB (CD137) and a signaling domain of CD3-zeta (CD3ζ) such as of human CD3ζ. In some alternatives, the CAR design is based on different combinations of two scFv molecules, which target different extracellular epitopes of the IL13Rα2, with different VH-VL orientations and three possible lengths of CAR spacer. The rest of the CAR backbone, the transmembrane and the costimulatory domains are shared between the CARs. In more alternatives, a truncated version of the epidermal growth factor receptor (EGFRt) is also included, which is co-expressed with the CARs on the T cell surface. Additional alternatives may include a dihydrofolate reductase double mutant (DHFRdm) transgene, which allows methotrexate selection of T-cell products. As described herein, both CD8 and CD4 IL13Rα2 CAR-T cells exhibit potent in vitro tumor cytotoxicity and specific efficacy in vivo against glioblastoma tumor models.

Some alternatives include a CAR containing an scFv including VL and VH domains of an antibody referred to as IL13Ra2 Ab01, in the VL-linker-VH orientation. In some aspects, such CARs further include particular combination(s) of spacer, transmembrane and/or signaling domains. For example, in some aspects, such CARs include a spacer consisting or consisting essentially of no more than 15 or no more than 12 amino acids and/or containing or consisting or consisting essentially of an immunoglobulin hinge region or modified variant thereof, such as a hinge region of an IgG4 or modified variant thereof. In some aspects, the CAR domains further include a costimulatory and a primary signaling domain, such as 4-1BB and CD3zeta signaling domains. In some aspects, preferred alternatives may be advantageous in their ability to augment T cell effector functions, such as by leading to increased cytotoxicity and cytokine secretion in vitro and/or improving function in vivo, such as in the context of human glioblastoma, as compared to alternative CARs, such as those containing different binding domains (e.g., with different VH and/or VL regions and/or in which the VH and VL regions are present in a different orientation) and/or those containing the same binding domain but with one or more differences in other region(s) of the CAR, such as with an alternative spacer, such as a spacer with an increased length. Embodiments provided herein, in some aspects, are based on observations herein demonstrating ability to control tumor growth and/or increase median survival of subjects bearing IL-13Ra2-expressing tumors, such as in a mouse model involving mice bearing intracranially-engrafted human GBM, treated with a single injection of the IL13Ra2 targeted CART-cells.

Certain Nucleic Acids

Some embodiments of the methods and compositions provided herein include nucleic acids encoding a chimeric antigen receptor, the chimeric antigen receptor comprising: a) a ligand binding domain that binds to and/or interacts with an IL-13 alpha 2 (IL13Rα2) receptor and/or that comprises a CDR3, and optionally a CDR1 and a CDR2, of a VH region of SEQ ID NO:18 and a CDR3, and optionally a CDR1 and a CDR2, of a VL region of SEQ ID NO:19, b) a polypeptide spacer between the ligand binding domain and a transmembrane domain; c) the transmembrane domain; and d) intracellular signaling region. In some alternatives, the ligand binding domain is an antibody fragment, such as an antigen-binding fragment. In some alternatives, the ligand binding domain is single chain variable fragment (scFv). In some alternatives, the spacer is 15 amino acids or less but not less than 1 or 2 amino acids. In some alternatives, the spacer comprises an amino acid sequence of $X_1PPX_2P$. In some alternatives, the spacer region comprises a portion of a hinge region of a human antibody or modified variant thereof. In some alternatives, the intracellular signaling region comprises primary and a costimulatory signaling domains, optionally comprising all or a portion of a CD3 zeta in combination with a co-stimulatory domain selected from the group consisting of signaling domains of CD27, CD28, 4-1BB, OX-40, CD30, CD40, PD-1, ICOS, LFA-1, CD2, CD7, NKG2C, and B7-H3 and combinations thereof. In some alternatives, the intracellular signaling region comprises a signaling portion of a CD3 zeta and a signaling portion of a 4-1BB. In some alternatives, the transmembrane domain comprises a CD28 transmembrane domain (CD28tm). In some alternatives, the spacer comprises, consists of, or consists essentially of, an IgG4 hinge spacer (S). In some alternatives, the spacer comprises, consists of, or consists essentially of, an IgG4 hinge-CH3 spacer (M). In some alternatives, the spacer comprises, consists of, or consists essentially of, an IgG4 hinge-CH2 (L234D, N297A)-CHE spacer (L). In some alternatives, the scFv comprises a VL-VH orientation and spacer S. In some alternatives, scFv comprises a VH-VL orientation and a spacer, wherein the spacer is Spacer M or Spacer L. In some alternatives, the single chain variable fragment (scFv) comprises a sequence set forth in SEQ ID NO:61 or SEQ ID NO:62. In some alternatives, the single chain variable fragment (scFv) comprises a sequence set forth in SEQ ID NO:63 or SEQ ID NO:64. In some alternatives, the nucleic acid further comprises a nucleic acid that encodes a marker sequence. In some alternatives, the marker sequence is a truncated receptor and optionally is an EGFRt, a HER2t, or a CD19t. In some alternatives, the nucleic acid further comprises a dihydrofolate reductase transgene configured for methotrexate selection. In some alternatives, the dihydrofolate reductase transgene is a dihydrofolate reductase double mutant (DHFRdm). In some alternatives, the first, second, third, and/or fourth polynucleotide is codon optimized to reduce the total GC/AT ratio of the nucleic acid. In some alternatives, the first, second, third, and/or fourth polynucleotide is codon optimized for expression in humans. In some alternatives, the dihydrofolate reductase double mutant comprises amino acid mutations of L22F and F31S.

Some embodiments of the methods and compositions provided herein include expression vectors comprising the nucleic acid of any one of the alternatives herein. In some alternatives, the vector is a viral vector. In some alternatives, the vector is a lentiviral or adenoviral vector.

Certain Chimeric Receptors

Some embodiments of the methods and compositions provided herein include chimeric receptor polypeptides, encoded by the nucleic acid of any one of the alternatives herein or by the vector of any one of the alternatives herein.

Certain Host Cells

Some embodiments of the methods and compositions provided herein include host cells comprising the nucleic acid of any one of the alternatives herein or the expression vector of any one of the alternatives herein or expresses the chimeric receptor of any one of the alternatives herein. In some embodiments, a host cell comprises a genetically modified cell. In some alternatives, the chimeric antigen receptor is encoded by the nucleic acid of any one of the alternatives herein or by the vector of any one of the alternatives herein. In some alternatives, the expression vector comprises the nucleic acid of any one of the alternatives herein is provided. In some alternatives, the host cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the CD8+ cytotoxic T lymphocyte cell is a central memory T cell and, wherein the central memory T cell is positive for CD45RO+, CD62L+, and CD8+. In some alternatives, the host cell is a CD4+T helper lymphocyte cell selected from the group consisting of naïve CD4+ T cells, central memory CD4+ T cells, effector memory CD4+ T cells, and bulk CD4+ T cells. In some alternatives, the CD4+ helper lymphocyte cell is a naïve CD4+ T cell and, wherein the naïve CD4+ T cell is positive for CD45RA+, CD62L+ and CD4+ and negative for CD45RO. In some alternatives, the host cell is a precursor T cell. In some alternatives, the host cell is a hematopoietic stem cell.

Some embodiments of the methods and compositions provided herein include a host cell of any one of the alternatives herein or the composition of any one of the alternatives herein for use in the treatment or inhibition of a cancer or a solid tumor expressing an IL-13α2 receptor is provided. The composition comprises the host cell of any one of the alternatives herein and a pharmaceutical excipient. In some alternatives, the cancer is a glioblastoma tumor. In some alternatives, the cancer is glioblastoma multiforme (GBM). In some alternatives, the cancer is an IL13Rα-positive malignancy. In some alternatives, the cancer is brain cancer or brain tumors.

Certain Compositions

Some embodiments of the methods and compositions provided herein include compositions comprising a host cell of any one of the alternatives herein, and a pharmaceutically acceptable excipient.

Certain Methods of Preparing Host Cells

Some embodiments of the methods and compositions provided herein include methods for preparing a host cell of any one of the alternatives herein is provided comprising: a) introducing a nucleic acid of any one of the alternatives herein or an expression vector of any one of the alternatives herein into lymphocytes; and b) culturing the lymphocytes in the presence of anti-CD3 and/or anti CD28 antibodies, and at least one homeostatic cytokine until the cells expand; and c) selecting the lymphocytes with a selection reagent; wherein the selection reagent is configured to selectively enrich cells transduced with the nucleic acid or vector. In some alternatives, the selection reagent is methotrexate. In some alternatives, the lymphocytes have a CD45RA−, CD45RO+, and CD62L+ phenotype. In some alternatives, the lymphocytes are CD8+ or CD4+. In some alternatives, the cytokine is IL-15, Il-7 and/or Il-21. In some alternatives, the method further comprises introducing a second nucleic acid into the host cell, the second nucleic acid encoding a marker protein. In some alternatives, the marker protein is EGFRt.

Certain Methods of Therapy

Some embodiments of the methods and compositions provided herein include methods of performing cellular immunotherapy in a subject having a cancer or a tumor comprising: administering the host cell of anyone of the alternatives herein or the composition of the alternatives herein is provided to the subject. The composition comprises a host cell of any one of the alternatives herein, and a pharmaceutically acceptable excipient is provided. In some alternatives, the cancer is glioblastoma tumor. In some alternatives, the cancer is glioblastoma multiforme (GBM). In some alternatives, the cancer is an IL13Rα-positive malignancy. In some alternatives, the cancer is brain cancer. In some alternatives, the subject is selected to receive combination therapy. In some alternatives, the combination therapy comprises administering a chemotherapeutic drug. In some alternatives, the combination therapy comprises administering radiation therapy. In some alternatives, the chemotherapeutic drug comprises electochemotherapy, alkylating agents, antimetabolites (for example, 5-fluorouracil (5-FU), 6-mercaptopurine (6-MP), Capecitabine (Xeloda®), Cladribine, Clofarabine, Cytarabine (Ara-C®), Floxuridine, Fludarabine, Gemcitabine (Gemzar®), Hydroxyurea, Methotrexate, Pemetrexed (Alimta®), Pentostatin, and Thioguanine), anti-tumor antibiotics, topoisomerase inhibitors, mitotic inhibitors, corticosteroids, DNA intercalating agents, or checkpoint inhibitors (checkpoint kinases CHK1, CHK2). In some alternatives, the cancer is a glioma.

Development of Certain IL13Ra2 CARs

Shown in FIG. 1 are schematic representations of the nucleic acids encoding the structure of several IL-13Rα2 CARs that were created, each having one of various binding domains, one of various spacer regions, together with a transmembrane domain and intracellular signaling domain(s). The nucleic acid sequence of each of these exemplary IL-R13Rα2 CARs includes a leader sequence, which may be used for example to allow translation of the mRNA transcript encoding the CAR. Each of the exemplary CARs also comprised an IL-13Rα2 scFv, specifically an anti-IL13Ra2 scFv having VH and VL domains set forth in SEQ ID NOs: 14 and 16, respectively or having VH and VL domains set forth in SEQ ID NOs: 15 and 17, respectively. Each of the CARs generated and tested were generated with four different scFv binding domains. The four binding domains included each of the anti-IL 13Ra2 VH/VL pairs, in each of the VL-VH and VH-VL orientation, individually.

The three different spacers, individually present in the exemplary CARs, are shown in FIG. 1, positioned between the scFv and the transmembrane domain. The spacers tested varied in length and were derived from immunoglobulin constant regions. The spacer with the shortest amino acid sequence length was a modified human IgG4 hinge region), a spacer with an intermediate (medium) length included the modified human hinge region and further included a CH3 domain (IgG4-CH3); the longest spacer tested included the modified IgG4 hinge region, a modified CH2 region and the CH3 region (IgG4-CH2 (L235D, N297Q)-CH3 (L)). Each of the exemplary CARs generated further included a transmembrane derived from human CD28 (CD28tm domain) and signaling domains of human 4-1BB and CD3zeta (4-1BB domain, CD3 zeta domain).

Each of the nucleic acids encoding and used to express the CARs further included a sequence encoding a T2A skip sequence and a nucleic acid encoding a truncated surrogate marker of CAR expression.

In some alternatives, the ligand binding domain of embodiments of the provided CARs comprises a heavy chain variable region that has or consists of the amino acid sequence of SEQ ID NO:18, or has or consists of a sequence having at least 90, 91, 92, 93, 94, 95, 96, 97, 98, or 99% identity to SEQ ID NO:18, or that comprises a CDR1, CDR2, and/or CDR3 of, typically at least a CDR3 of, a VH region having the sequence of SEQ ID NO:18.

In some alternatives, the ligand binding domain of embodiments of the provided CARs comprises a light chain variable region that has or consists of the amino acid sequence of SEQ ID NO:19, or has or consists of a sequence having at least 90, 91, 92, 93, 94, 95, 96, 97, 98, or 99% identity to SEQ ID NO:19, or that comprises a CDR1, CDR2, and CDR3 of a VL region having the sequence of SEQ ID NO:19. Sequences have been described in WO2014072888, included by reference in its entirety herein.

In some alternatives, the ligand binding region that specifically binds to human IL-13-Ra2 comprises: (a) a heavy chain CDR1 comprising SEQ ID NO:20; (b) a heavy chain CDR2 comprising SEQ ID NO:21; (c) a heavy chain CDR3 comprising SEQ ID NO:22; and/or comprises (d) a light chain CDR1 comprising SEQ ID NO:23; (e) a light chain CDR2 comprising SEQ ID NO:24; and/or (f) a light chain CDR3 comprising SEQ ID NO:25.

In some alternatives, the ligand binding region comprises the heavy chain variable region amino acid sequence of SEQ ID NO:18 and the light chain variable region amino acid sequence of SEQ ID NO:19.

In some alternatives, the ligand binding domain comprises a heavy chain CDR2 (CDRH2) comprising SEQ ID NO:28; (c) a heavy chain CDR3 (CDRH3) comprising SEQ ID NO:29; (d) a light chain CDR1 comprising SEQ ID NO:30; (e) a light chain CDR2 comprising SEQ ID NO:31; and/or (f) a light chain CDR3 comprising SEQ ID NO:32.

In some alternatives, the ligand binding domain comprises a heavy chain CDR1 (CDR-H1) comprising a sequence set forth in SEQ ID NO:33, SEQ ID NO:34, SEQ ID NO:35, or SEQ ID NO:36. In some alternatives CDR-H2 comprises a sequence set forth in SEQ ID NO:37, SEQ ID NO:38, SEQ ID NO:39, or SEQ ID NO:40. In some alternatives, CDRH3 comprises a sequence set forth in SEQ ID NO:41.

In some embodiments, the CAR comprises a spacer interposed between the binding domain and transmembrane domain. In some alternatives, the spacer comprises or consists of or consists essentially of at least a portion of an immunoglobulin constant region, such as all or a portion of an immunoglobulin hinge region, such as an IgG4 hinge region, or a functional variant thereof. In some embodiments, the immunoglobulin constant and/or hinge region is a region of human IgG, such as IgG4 or IgG1, or a variant thereof. The spacer can be of a length that provides for increased responsiveness of the cell following antigen binding, as compared to in the absence of the spacer. Exemplary spacers include those described in international patent application publication number WO2014031687, hereby expressly incorporated by reference in its entirety. In some examples, the spacer is or is about 12 amino acids in length or is no more than 12 amino acids in length or is or is about 15 amino acids in length or is or is about no more than 15 amino acids in length.

Example spacers include those having at least 10 to 229 amino acids, 10 to 200 amino acids, 10 to 175 amino acids, 10 to 150 amino acids, 10 to 125 amino acids, 10 to 100 amino acids, 10 to 75 amino acids, 10 to 50 amino acids, 10 to 40 amino acids, 10 to 30 amino acids, 10 to 20 amino acids, or 10 to 15 aminoacids, and including any integer between the endpoints of any of the listed ranges. In some embodiments, a spacer region has 12 amino acids or less but not zero, 119 amino acids or less but not zero, or 229 amino acids or less but not zero. In some embodiments, the spacer is less than 250 amino acids in length but not zero, less than 200 amino acids in length but not zero, less than 150 amino acids in length but not zero, less than 100 amino acids in length but not zero, less than 75 amino acids in length but not zero, less than 50 amino acids in length but not zero, less than 25 amino acids in length but not zero, less than 20 amino acids in length but not zero, less than 15 amino acids in length but not zero, less than 12 amino acids in length but not zero, or less than 10 amino acids in length but not zero. In some embodiments, the spacer is from or from 10 to 250 amino acids in length, 10 to 150 amino acids in length, 10 to 100 amino acids in length, 10 to 50 amino acids in length, 10 to 25 amino acids in length, 10 to 15 amino acids in length, 15 to 250 amino acids in length, 15 to 150 amino acids in length, 15 to 100 amino acids in length, 15 to 50 amino acids in length, 15 to 25 amino acids in length, 25 to 250 amino acids in length, 25 to 100 amino acids in length, 25 to 50 amino acids in length, 50 to 250 amino acids in length, 50 to 150 amino acids in length, 50 to 100 amino acids in length, 100 to 250 amino acids in length, 100 to 150 amino acids in length, or 150 to 250 amino acids in length. Exemplary spacers include IgG4 hinge alone, IgG4 hinge linked to CH2 and CH3 domains, or IgG4 hinge linked to the CH3 domain. Exemplary spacers include, but are not limited to, those described in Hudecek et al. *Clin. Cancer Res.,* 19:3153 (2013), international patent application publication number WO2014031687, U.S. Pat. No. 8,822,647 or published app. No. US2014/0271635 hereby expressly incorporated by reference in their entireties.

In some aspects, the spacer of the CAR consists of or comprises an IgG4 hinge, an IgG4 hinge-CH3 or an IgG4 hinge-CH2(L235D, N297Q)-CH3.

In some alternatives, the ligand binding domain comprises (a) a heavy chain variable region comprising a CDR1, a CDR2, and a CDR3 of the VH sequence of SEQ ID NO:18; and, (b) a light chain variable region comprising a CDR1, a CDR2, and a CDR3 of the VL sequence of SEQ ID NO:19. Sequences can be found in WO2014/072888, which is hereby expressly incorporated by reference in its entirety herein.

In some alternatives, the orientation of the chains is VL-linker-VH. In some aspects, the orientation is VH-linker VL.

In some alternatives, the ligand binding region comprises a heavy chain variable region comprising a CDR1, CDR2, and CDR3 of the VH sequence shown in SEQ ID NO:18; a light chain variable region comprising a CDR1, CDR2, and CDR3 of the VL sequence shown in SEQ ID NO:19. In some alternatives, a spacer is provided wherein the spacer comprises an immunoglobulin constant region, such as one including all or part of an Fc region that includes at least one pair of amino acid substitutions selected from the group consisting of the amino acid sequence of SEQ ID NO:42 and SEQ ID N0:43; or an engineered Fc region and at least one engineered light chain constant region selected from group consisting of L443C (SEQ ID NO:44), Q347C (SEQ ID NO:45), kK183C (SEQ ID NO:46), SEQ ID NO:47, L443C/kK183C (SEQ ID NO:44 and SEQ ID NO:46), Q347C/kA111 C (SEQ ID NO:45 and SEQ ID NO:47), and Q347C/kK183C (SEQ ID NO:45 and SEQ ID NO:46).

In some alternatives, the constant region or portion thereof comprises a sequence set forth in SEQ ID NO:48.

In some alternatives, Ab02-derived scFv comprises a sequence set forth in SEQ ID NO:49 (LCDR1), SEQ ID NO:50 (LCDR2) and/or SEQ ID NO:51 (LCDR3). In some alternatives, the Ab02 antibody comprises a sequence as set forth in SEQ ID NO:55 (HCDR1), SEQ ID NO:56 (HCDR2), and/or SEQ ID NO:57 (HCDR3).

In some alternatives, the Ab01 antibody comprises a sequence set forth in SEQ ID NO:52 (LCDR1), SEQ ID NO:53 (LCDR2) and/or SEQ ID NO:54 (LCDR3). In some alternatives, the Ab01 antibody comprises a sequence as set forth in SEQ ID NO:58 (HCDR1), SEQ ID NO:59 (HCDR2), and/or SEQ ID NO:60 (HCDR3).

In some embodiments, the CAR includes an antigen-binding region that is or comprises an scFv including VH and VL domains in the VL-linker-VH orientation. In some embodiments, such as in some aspects of such embodiments, the VH domain comprises an amino acid sequence of SEQ ID NO:18, a CDR3 (and, optionally, CDRs 1 and 2) of the VH sequence set forth in SEQ ID NO:18, and/or comprises or consists of an amino acid sequence having at least 90, 91, 92, 93, 94, 95, 96, 97, 98, or 99% identity to SEQ ID NO:18, or that comprises a CDR1, CDR2, and/or CDR3 of, typically at least a CDR3 of, a VH region having the sequence of SEQ ID NO:18; in some aspects, e.g., of such embodiments, the VH is a VH derived from Ab01. In some aspects of such embodiments, the VL domain comprises an amino acid sequence of SEQ ID NO:19, a CDR3 (and, optionally, CDRs 1 and 2) of the VL sequence set forth in SEQ ID NO:19, and/or comprises or consists of an amino acid sequence having at least 90, 91, 92, 93, 94, 95, 96, 97, 98, or 99% identity to SEQ ID NO:19, or that comprises a CDR1, CDR2, and/or CDR3 of, typically at least a CDR3 of, a VL region having the sequence of SEQ ID NO:19 in some aspects, e.g., of such embodiments, the VH is a VH derived from Ab01. In some aspects of any of such embodiments, such as aspects of the CARs having such binding domains, the CAR includes a spacer region between the binding domain and transmembrane domain that contains no more than at or about 50, 40, 30 or 20 amino acids in length, such as no more than at or about 15 or no more than at or about 12, amino acids, and/or contains or is or consists essentially of an immunoglobulin hinge region or variant thereof, such as an IgG4 hinge or variant thereof.

In some aspects, the CARs and/or cells expressing the same exhibit one or more increased or superior functional activity as compared to a reference CAR. In some aspects, the reference CAR is a CAR having the same binding domain (and optionally otherwise identical) but having a spacer differing in length and/or composition, such as one greater than at or about 50, 40, 30, 20, 15, or 12 amino acids in length, and/or a CAR having a binding domain with the same or similar variable regions, but in an alternative orientation. In some embodiments, the function is as observed in an in vitro assay such as a co-culture assay with cells expressing IL-13Ra2 (such as an assay measuring cytokine production or cytolytic activity) or an in vivo assay using an animal model with a tumor positive for IL-13Ra2, such as one assessing tumor burden reduction or survival following administration of cells, such as T cells, expressing the CAR.

In the alternatives herein, eight CARs having various combinations of antigen-binding domains and other domains as depicted in FIG. 1 were tested in various assays. Certain Sequences In some alternatives, the Ab01 VH comprises a sequence set forth in SEQ ID NO:14. In some alternatives, the Ab01 VL comprises a sequence set forth in SEQ ID NO:16. In some alternatives, the IL13Ra2 Ab01 VLVH scFv is encoded by a sequence set forth in SEQ ID NO:61. In some alternatives, the IL13Ra2 Ab01 VHVL scFv is encoded by a sequence set forth in SEQ ID NO:62 which includes an Ab01-VL sequence, an Ab01-VH sequence, an ATG start codon, a 5' NheI restriction site (GCTAGC), and a 3' RsrII restriction site (CGGACCG). In some alternatives, the Ab01-VH protein sequence comprises SEQ ID NO:65. In some alternatives, Ab01 HCDR1 comprise a sequence set forth in SEQ ID NO:66. In some alternatives, Ab01 HCDR2 comprise a sequence set forth in SEQ ID NO:67. In some alternatives, Ab01 HCDR3 comprise a sequence set forth in SEQ ID NO:68. In some alternatives, Ab01-VL comprise a sequence set forth in SEQ ID NO:69. In some alternatives, Ab01 LCDR1 comprise a sequence set forth in SEQ ID NO:70. In some alternatives, Ab01 LCDR2 comprise a sequence set forth in SEQ ID NO:71. In some alternatives, Ab01 LCDR3 comprise a sequence set forth in SEQ ID NO:72.

In some alternatives, the Ab02 VH comprises a sequence set forth in SEQ ID NO:15. In some alternatives, the Ab02 VL comprises a sequence set forth in SEQ ID NO:17. In some alternatives, the IL13Ra2 Ab02 VLVH scFv is encoded by a sequence set forth in SEQ ID NO:63. In some alternatives, the IL13Ra2 Ab02 VHVL scFv is encoded by a sequence set forth in SEQ ID NO:64, which includes an Ab02-VL sequence, an Ab02-VH sequence, an ATG start codon, a 5' NheI restriction site (GCTAGC), and a 3' RsrII restriction site (CGGACCG). In some alternatives, Ab02-VH protein sequence comprise a sequence set forth in SEQ ID NO:73. In some alternatives, Ab02 HCDR1 comprise a sequence set forth in SEQ ID NO:74. In some alternatives, Ab02 HCDR2 comprise a sequence set forth in SEQ ID NO:75. In some alternatives, Ab02 HCDR3 comprise a sequence set forth in SEQ ID NO:76. In some alternatives, Ab02-VL protein sequence comprise a sequence set forth in SEQ ID NO:77. In some alternatives, Ab02 LCDR1 comprise a sequence set forth in SEQ ID NO:78. In some alternatives, Ab02 LCDR2 comprise a sequence set forth in SEQ ID NO:79. In some alternatives, Ab02 LCDR3 comprise a sequence set forth in SEQ ID NO:80.

EXAMPLES

Example 1—Construction of IL-13Rα2-Targeting CARs

Various IL-13Rα2-targeting CARs were constructed. As shown in FIG. 1, IL-13Rα2 specific CARs included: one of a number of single-chain variable fragment (scFv) that specifically recognized an extracellular epitope of IL-13 alpha 2 receptor (IL-13Rα2); one of various spacer domains (marked "S", "M" and "L"); a transmembrane domain derived from a human CD28 (CD28tm); a costimulatory domain derived from human 4-1BB; a CD3ζ-derived signaling domain; a T2A ribosomal skip sequence; and a truncated EGFR (EGFRt) transduction marker; and optionally a further T2A ribosomal skip sequence and a dihydrofolate reductase double mutant (DHFRdm) transgene configured for methotrexate selection.

Examples of antibodies or epitope binding fragments from which single-chain variable fragment (scFv) can be derived include humanized anti-IL-13-Ra2 IgG1 antibody hu08 (Creative Biolabs, NY), and Anti-IL13RA2 Therapeutic Antibody (hu07 v.1) (Creative Biolabs, NY).

The spacer domain was linked in each CAR with the scFv and connected the extracellular binding element to the transmembrane domain. Each of the CARs was generated to include one of the three different spacers (S, M, or L), each with an amino acid sequence of a different length (Spacer S, SEQ ID NO:9; Spacer M, SEQ ID NO:10; or a Spacer L, SEQ ID NO:11). Different scFv configurations used individually in the various IL-13Rα2 CARs, including VH and VL domains derived from one of two different anti-IL-13Ra2-directed antibodies ('Hu08', Ab01; and 'Hu07', Ab02). The scFv portion of each CAR was comprised of a VH region having a sequence as set forth in SEQ ID NO:14 or SEQ ID NO:15 and a VL region having a sequence set forth in SEQ ID NO:16 or SEQ ID NO:17, present in a VL-VH or VH-VL orientation, connected by a flexible peptide linker.

Example 2—Functional Comparison of CARs Derived from Different Antibodies

A functional comparison of CARs including scFv binding domains derived from different antibodies in different orientations was performed. The comparison included a surface expression analysis of EGFRt, and a cytokine release assay. In this study, each of the CARs included the "S" spacer (having the amino acid sequence of SEQ ID NO:9, a modified immunoglobulin hinge region), as well as the transmembrane and costimulatory and primary signaling domains described and shown in FIG. 1, with one of the various scFvs binding regions (VH/VL domains and orientations) shown in FIG. 1. CARs included: IL-13Ra2 Ab01 VLVH Spacer S CAR; IL-13Ra2 Ab01 VHVL Spacer S CAR; IL-13Ra2 Ab02 VLVH Spacer S CAR; and IL-13Ra2 Ab02 VHVL Spacer S CAR.

Figure 2A:
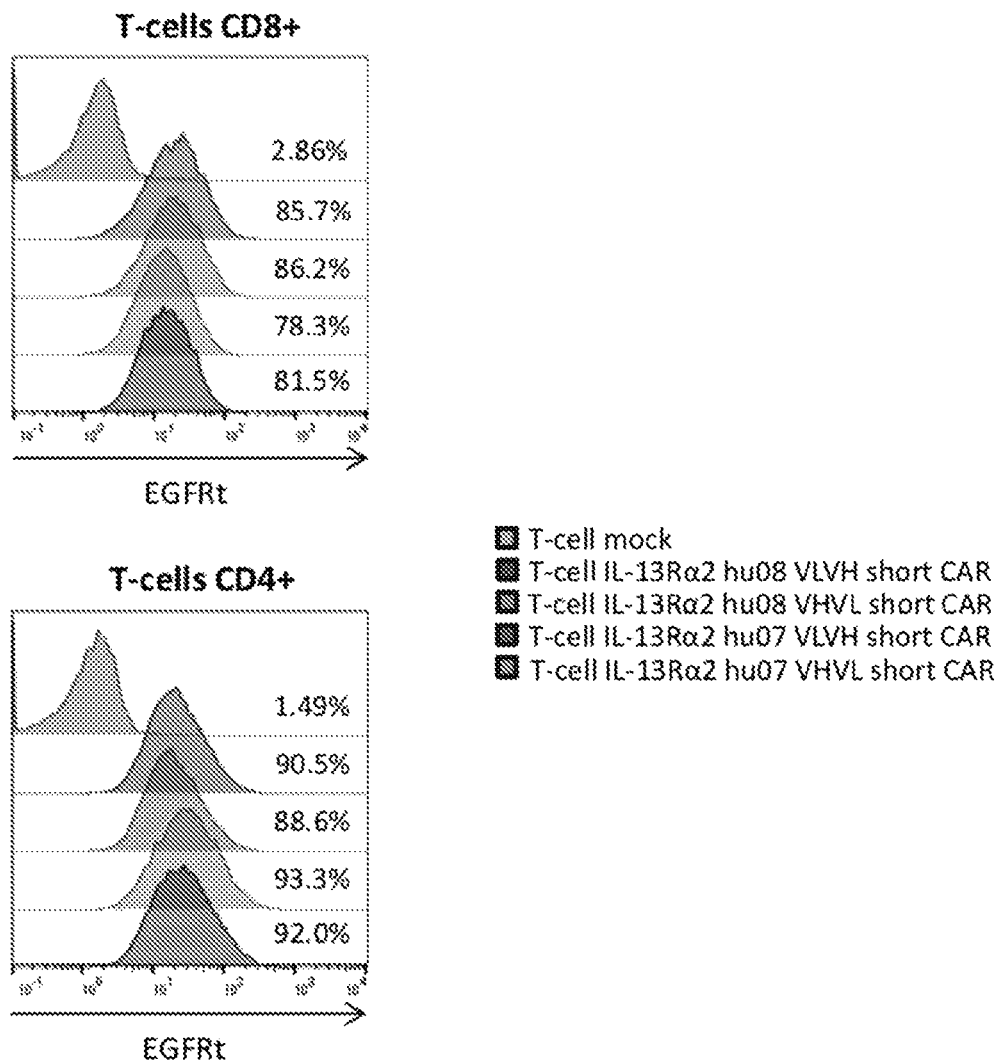
FIG. 2A depicts a flow cytometry analysis of EGFRt expression in CD8+ Tcells (upper panel) or CD4+ T cells (lower panel) transduced with various CARs depicted in FIG. 1. From the top row to the bottom row of each panel: T cell mock; T cell with IL-13Ra2 Ab01 VL-VH Spacer S CAR; T cell with IL-13Ra2 Ab01 VH-VL Spacer S CAR; T cell with IL-13Ra2 Ab02 VL-VH Spacer S CAR; and T cell with IL-13Ra2 Ab02 VH-VL Spacer S CAR.

Expression of CARs in cells was examined by determining expression of the EGFRt marker in CD8+ and CD4+ T cells using flow cytometry (FIG. 2A)

Figure 2B:
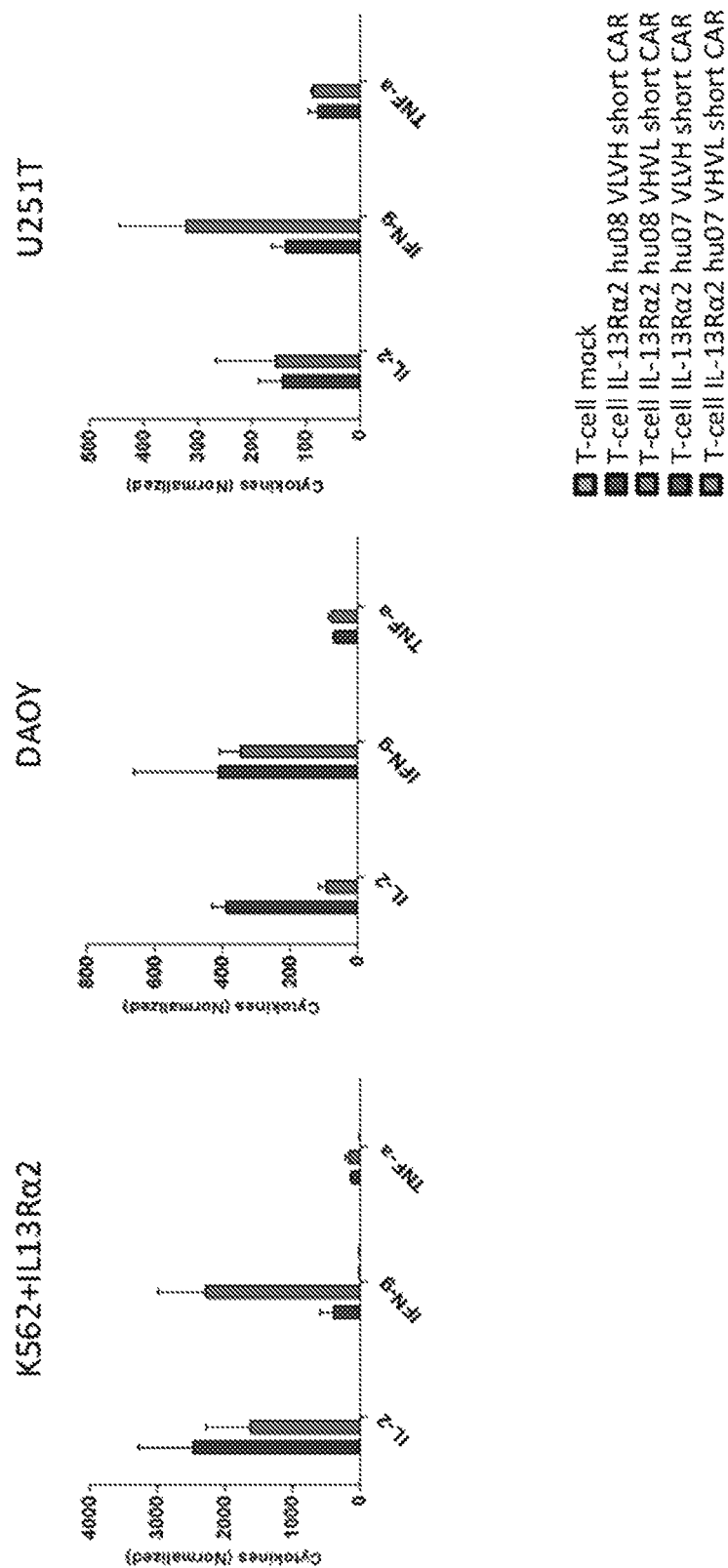
FIG. 2B depicts graphs of cytokine production (IL-2, IFN-γ, TNF-α) from CD8+ T cells transduced with various CARs and incubated with indicated target cells. The key corresponds to T cell mock; T cell with IL-13Ra2 Ab01 VL-VH Spacer S CAR; T cell with IL-13Ra2 Ab01 VH-VL Spacer S CAR; T cell with IL-13Ra2 Ab02 VL-VH Spacer S CAR; and T cell with IL-13Ra2 Ab02 VH-VL Spacer S CAR.
Figure 2C:
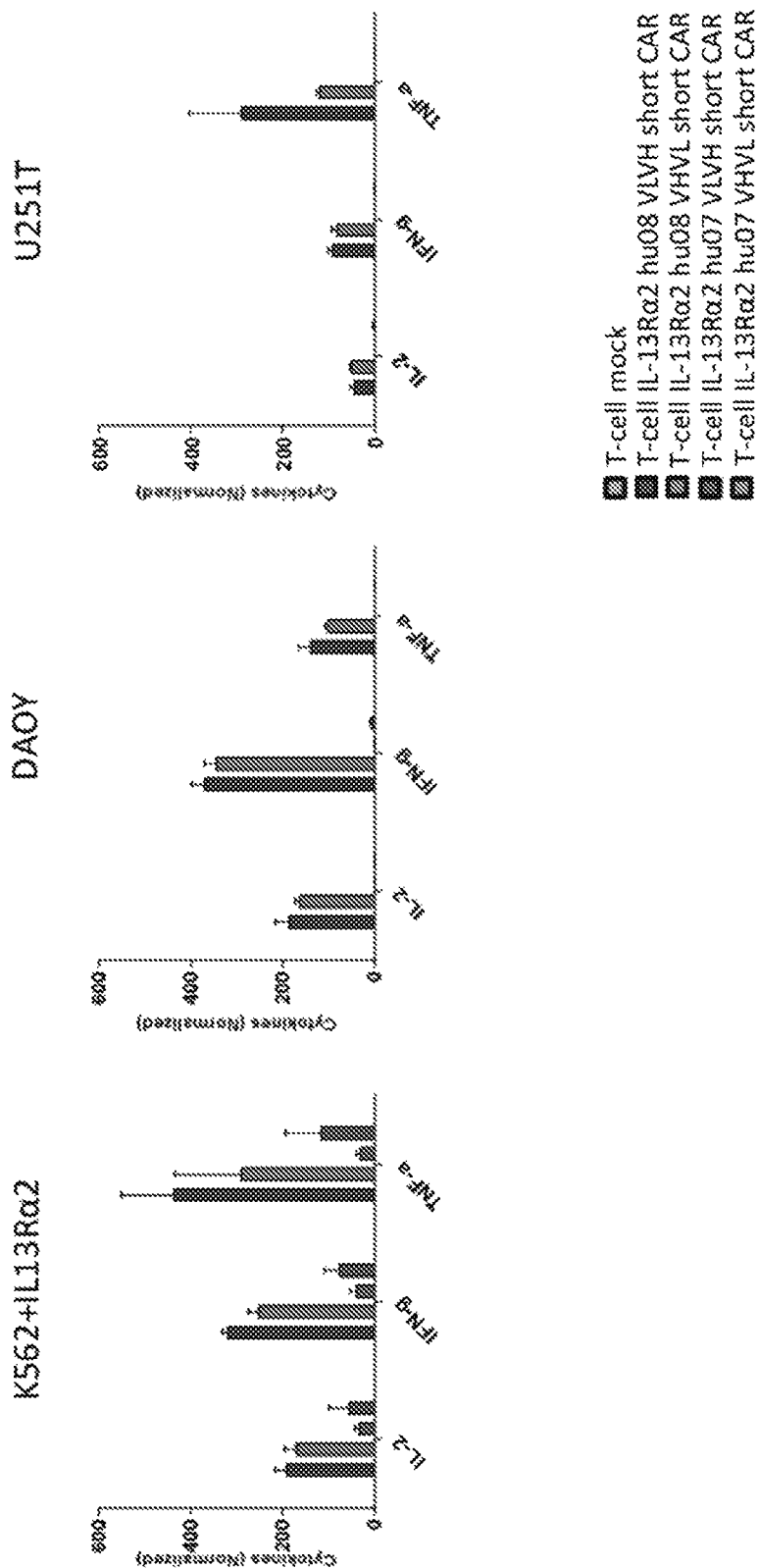
FIG. 2C depicts graphs of cytokine production (IL-2, IFN-γ, TNF-α) from CD4+ T cells transduced with various CARs and incubated with indicated target cells. The key corresponds to T cell mock; T cell with IL-13Ra2 Ab01 VL-VH Spacer S CAR; T cell with IL-13Ra2 Ab01 VH-VL Spacer S CAR; T cell with IL-13Ra2 Ab02 VL-VH Spacer S CAR; and T cell with IL-13Ra2 Ab02 VH-VL Spacer S CAR.

CAR T cells were co-cultured, individually, with DAOY cells (human brain/cerebellum cel line), U251T cells (human gioblastoma cell line) and K562 cells (human chronic myelogenous leukemia cells) engineered to express IL13Rα2. After 24 h levels of IL-2, IFN-γ and TNF-α were measured in supernatants using a cytokine assay. Increased cytokine production following incubation with target cells was observed for CD8+ and CD4+ T cells expressing CARs containing binding domains having VH and VL domains from the Ab01 antibody, in both VH/VL orientations (FIG. 2B and FIG. 2C).

Example 3—Functional Comparison of CARs Including Different Spacers

Figure 3A:
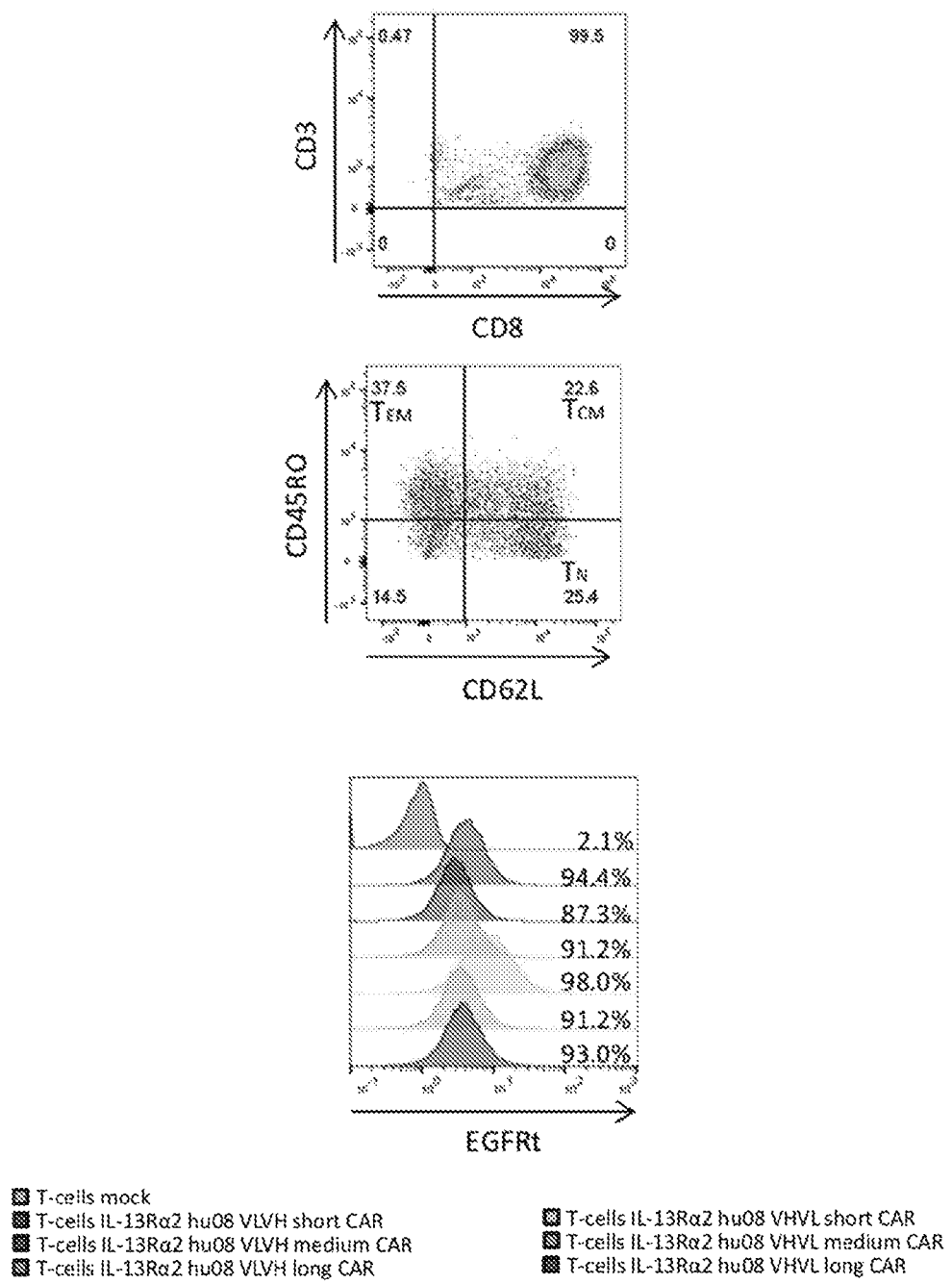
FIG. 3A depicts a multi-parameter flow cytometry analysis of T cells derived from healthy donor and transduced with IL-13Rα2 hu08 CARs with histograms quadrants were drawn based on control staining (upper and middle panels); and a flow cytometry analysis of EGFRt expression in CD8+ T cells transduced with a CAR (lower panel). Indicated CARs included: mock; IL-13Ra2 Ab01 VL-VH Spacer-S CAR; IL-13Ra2 Ab01 VL-VH Spacer-M CAR; IL-13Ra2 Ab01 VL-VH Spacer-L CAR; IL-13Ra2 Ab01 VH-VL Spacer-S CAR; IL-13Ra2 Ab01 VH-VL Spacer-M CAR; and IL-13Ra2 Ab01 VH-VL Spacer-L CAR.

A functional comparison of CARs including scFvs derived from the same antibody (in different orientations) and different spacers of different length was performed. The four CARS depicted in FIG. 1 were tested for cell surface expression in CD8+ by gating for the marker sequence, EGFRt (FIG. 3A). Furthermore, the CD8+ cells carrying the CARs were also tested for their ability to cause specific lysis, as well as their ability to release cytokines. In this study, each of the exemplary CARs included one of two different binding domains—an scFv having VL and VH domains from Ab01, either in the VL-VH or the VH-VL orientation—and one of the various spacers ("S" (having the amino acid sequence of SEQ ID NO:9), "M" (having the amino acid sequence of SEQ ID NO: 10) and "L" (having the amino acid sequence of SEQ ID NO:11)), as well as the transmembrane and costimulatory and primary signaling domains described and depicted in FIG. 1.

Representative results from multi-parameter flow cytometry analysis of T cells derived from healthy donor and transduced with the indicated CARs lentivirus are shown in FIG. 3A (top and middle panels) in which histograms quadrants were drawn based on control staining. Surface surrogate marker (EGFRt) expression on CD8+IL-13Rα2 CAR T-cells was analyzed by flow cytometry (FIG. 3A, lower panel).

Figure 3B:
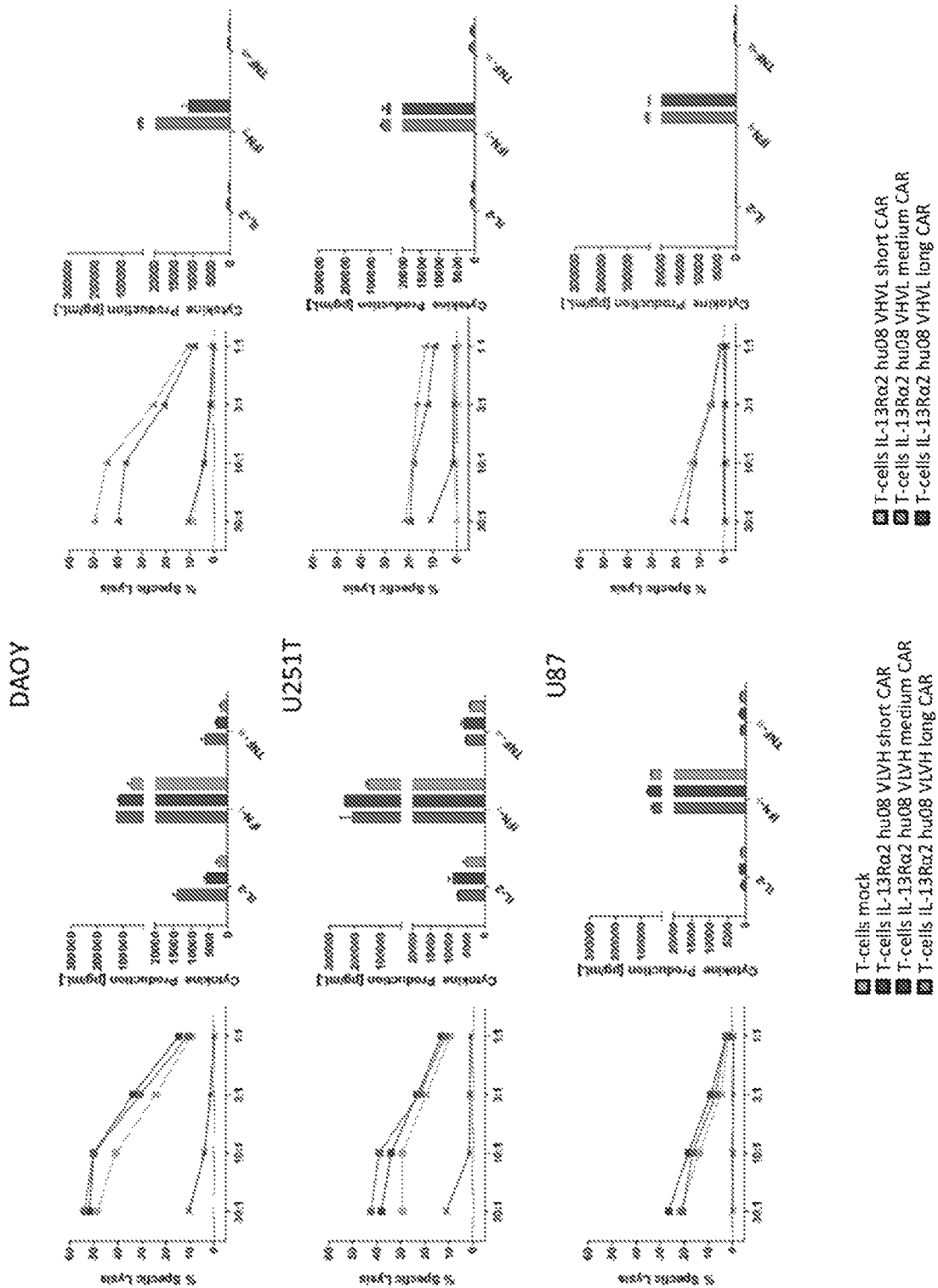
FIG. 3B depicts an analysis for cytokine production and cytolytic activity of CD8+ T cells containing a CAR, following co-culture with certain indicated target cells. Indicated CARs included: mock; IL-13Ra2 Ab01 VL-VH Spacer-S CAR; IL-13Ra2 Ab01 VL-VH Spacer-M CAR; IL-13Ra2 Ab01 VL-VH Spacer-L CAR; IL-13Ra2 Ab01 VH-VL Spacer-S CAR; IL-13Ra2 Ab01 VH-VL Spacer-M CAR; and IL-13Ra2 Ab01 VH-VL Spacer-L CAR.

IL-13Rα2-targeted CAR expressing CD8 T cells were co-cultured with different IL-13Ra2-expressing target cell lines at variable indicated effector to target ratios (FIG. 3B). A chromium release assay was used to assess cytolytic activity and cytokine production was assessed in supernatants. The chromium release assay was over a 4 hr co-culture period, while cytokine release was assessed following 24 hr co-culture (2:1 effector-target ratio). As shown in FIG. 3B, co-culture with the various CAR-expressing T cells led to specific lysis, increasingly with increased effector to target ratios, and levels of cytokine secretion. Compared to other CARs assessed, increased cytolytic activity was observed for cells expressing the CAR with the "S" spacer and including the scFv with the VL-VH orientation. In each of the CARs assessed having binding domains with the VL-VH orientation, target-specific cytolytic activity and cytokine production were observed. Additionally, in CARs with the VL-VH orientation, the presence of the "S" spacer was observed to result in superior effects compared to the other spacers tested. In contrast, cytolytic activity was not observed in this assay for CARs with the VH-VL orientation and the "S" spacer (whereas activity was observed for each of the VH-VL CARs having the "M" and "L" spacers).

With regard to cytokine production, as shown in FIG. 3B, T cell with IL-13Ra2 Ab01 VLVH Spacer S CAR, T cell with IL-13Ra2 Ab01 VLVH Spacer M CAR, T cell with IL-13Ra2 Ab01 VLVH Spacer L CAR led to higher expression of IFN-gamma. T cell with IL-13Ra2 Ab01 VHVL Spacer M CAR, and T cell with IL-13Ra2 Ab01 VHVL Spacer L CAR showed IFN-gamma expression. T cell with IL-13Ra2 Ab01 VLVH Spacer S CAR, T cell with IL-13Ra2

Ab01 VLVH Spacer M CAR, T cell with IL-13Ra2 Ab01 VLVH Spacer L CAR led to higher specific lysis.

With regard to specific lysis, as shown in FIG. 3B, at increased concentrations, the CD8+ cells carrying the IL-13Rα2 Ab01 VLVH spacer S CAR, IL-13Rα2 Ab01 VLVH medium CAR, and IL-13Rα2 Ab01 VLVH long CAR caused a significant amount of specific lysis at high concentrations of cell. Furthermore, these cells led to high production of the cytokine IFN-gamma.

In contrast, cells expressing the IL-13Rα2 Ab01 VHVL spacer S CAR, IL-13Rα2 Ab01 VHVL medium CAR and IL-13Rα2 Ab01 VHVL long CAR had decreased amounts of specific lysis when compared to the IL-13Rα2 Ab01 VLVH spacer S CAR, IL-13Rα2 Ab01 VLVH medium CAR and IL-13Rα2 Ab01 VLVH long CAR. Specific lysis was not seen with the IL-13Rα2 Ab01 VHVL spacer S CAR. Additionally, IL-13Rα2 Ab01 VHVL spacer S CAR expression did not lead to IFN-gamma expression, which was seen with the IL-13Rα2 Ab01 VHVL medium CAR and the IL-13Rα2 Ab01 VHVL long CAR.

Example 4—In Vivo Anti-Tumor Activity of an Anti-IL13Rα2 CAR

Therapeutic outcomes following administration of cells expressing an IL13Rα2-specific CAR containing a binding domain derived from antibody Ab01, VLVH orientation, spacer "S", were evaluated in a mouse glioblastoma model. The CARs used for the experiments were expressed in CD8+ cells. For the experiments, ffLuc+U87 glioblastoma cells ($0.2 \times 10^6$) were intracranially injected into the forebrain of NSG mice at day 0. On day 7, mice (n=3 per group) received no treatment (vehicle control or mock) or they received treatment with different doses ($2 \times 10^6$, $1 \times 10^6$ or $0.5 \times 10^6$ cells) of IL-13Rα2 Ab01 VLVH transduced CD8+ CAR T-cells.

Figure 4A:
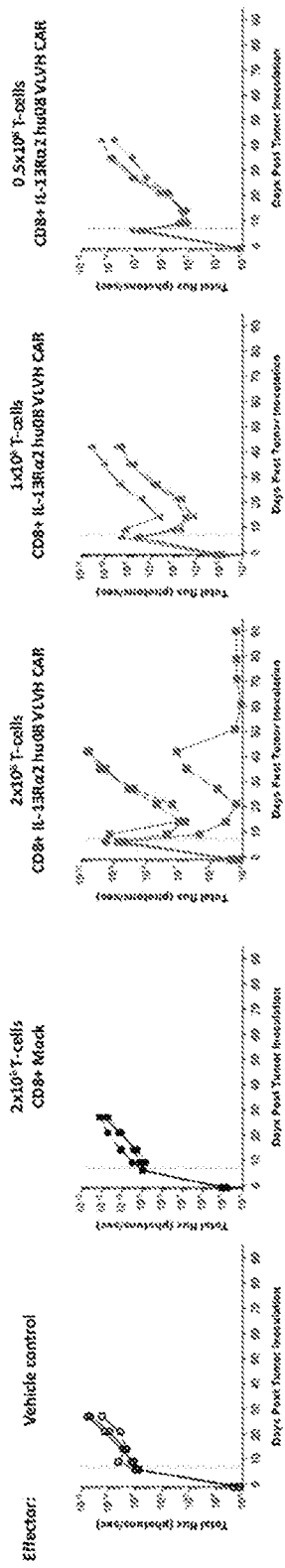
FIG. 4A depicts graphs of total flux (photons/sec) as a measure of tumor burden (y-axis) over time (days post-tumor inoculation, x-axis), for mice treated with: vehicle, mock cells, $2 \times 10^6$ T cells containing an anti-IL-13Rα2 CAR; $1 \times 10^6$ T cells containing an anti-IL-13Rα2 CAR; or $0.5 \times 10^6$ T cells containing an anti-IL-13Rα2 CAR. The anti-IL-13Rα2 CAR was IL-13Ra2 Ab01 VL-VH Spacer-S CAR.
Figure 4B:
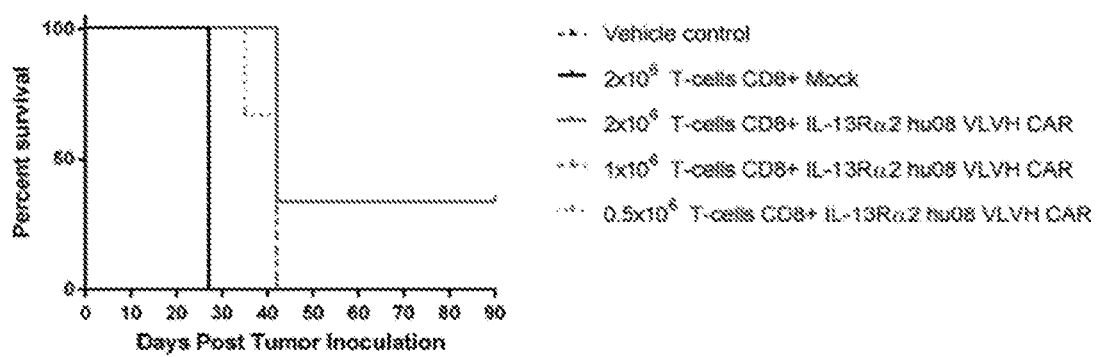
FIG. 4B depicts a Kaplan-Meier survival curve for mice treated with increasing doses of T cells expressing an anti-IL-13Rα2 CAR (IL-13Ra2 Ab01 VL-VH Spacer-S CAR).
Figure 5A:
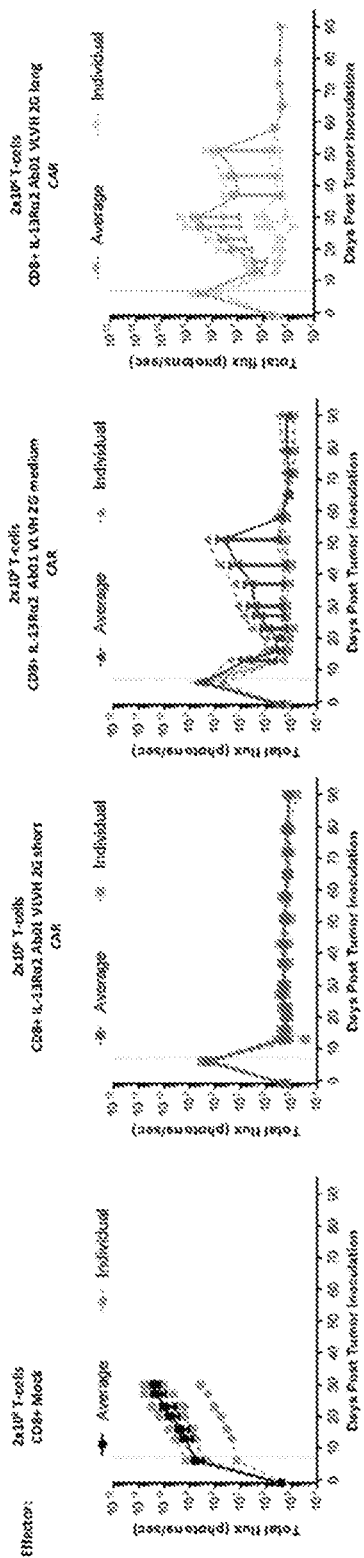
FIG. 5A depicts graphs of total flux (photons/sec) as a measure of tumor burden (y-axis) over time (days post-tumor inoculation, x-axis), for mice treated with: mock cells; $2 \times 10^6$ T cells containing an anti-IL-13Rα2 CAR containing a short spacer; $2 \times 10^6$ T cells containing an anti-IL-13Rα2 CAR containing a medium spacer; $2 \times 10^6$ T cells containing an anti-IL-13Rα2 CAR containing a long spacer.
Figure 5B:
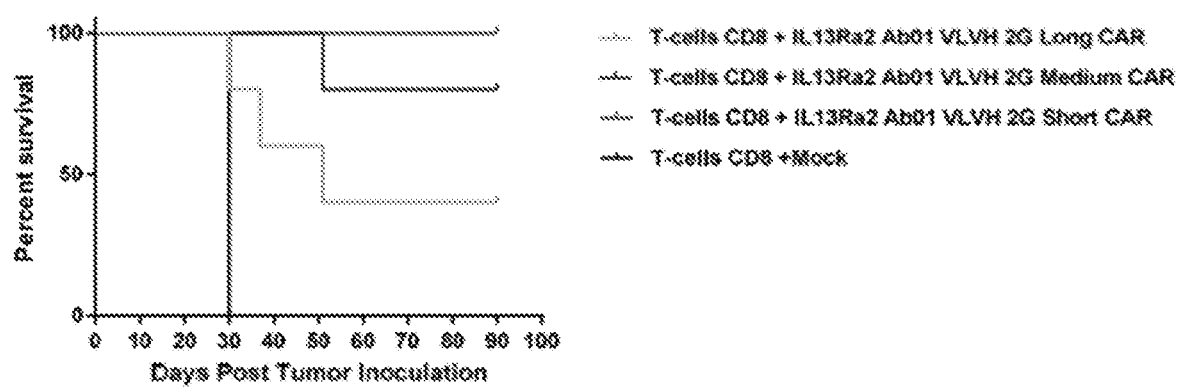
FIG. 5B depicts a Kaplan-Meier survival curve for mice treated with T cells expressing an anti-IL-13Rα2 CAR containing a long spacer, a medium spacer, or a short spacer.
Figure 5C:
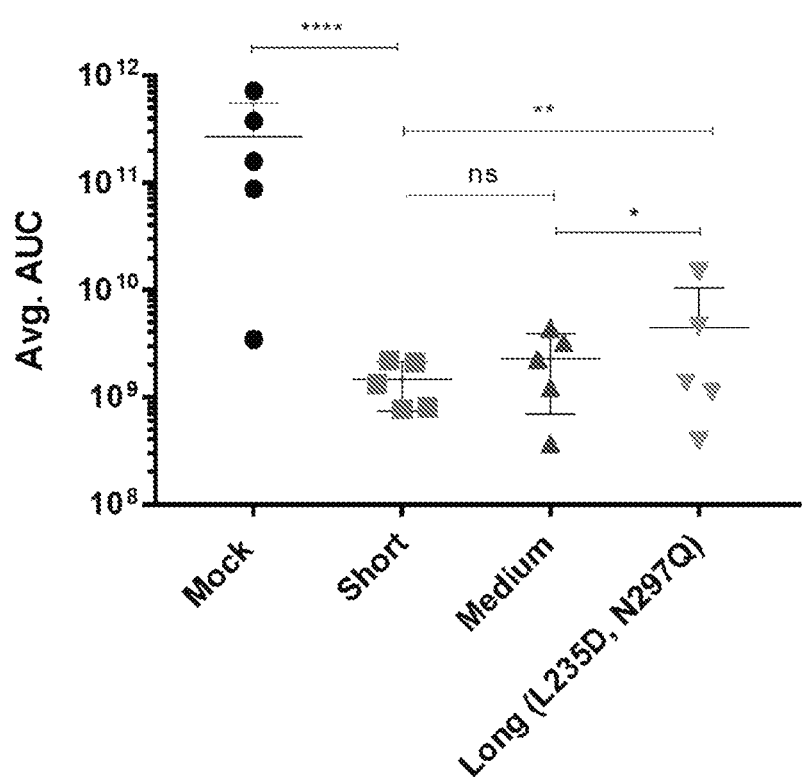
FIG. 5C depicts an area under curve (AUC) analysis of bioluminescent data for mice treated with T cells expressing an anti-IL-13Rα2 CAR containing a long spacer, a medium spacer, or a short spacer. The mean AUCs between IL13Ra2 Ab01 spacer variants CAR T-cells or Mock T-cells were compared. *, P<0.05. , P<0.01. **, P<0.0001.

FIG. 4A and FIG. 4B show results from a study demonstrating in vivo anti-tumor activity of an IL13Rα2-specific CAR containing the VH and VL domains derived from Ab01, in the VL-VH orientation, and the "S" spacer, along with the transmembrane and signaling domains as depicted in FIG. 1. Human glioblastoma cells expressing firefly luciferase (ffLuc$^+$ U87 glioblastoma cells) ($0.2 \times 10^6$) were intracranially injected into forebrains of NSG mice at day 0. On day 7, mice (n=3 per group) received Vehicle control or Mock administration or were administered treatment with different doses ($2 \times 10^6$, $1 \times 10^6$ or $0.5 \times 10^6$ cells) of CD8+ cells expressing the IL-13Rα2-specific CAR (Ab01 VL-VH). FIG. 4A shows plots of total flux (photons/sec) as a measure of tumor burden (y-axis) over time (days post-tumor inoculation, x-axis), for animals treated with vehicle or mock treatment (left) and indicated decreasing numbers of CAR+ cells (right-hand; right to left), demonstrating tumor regression following administration of cells expressing the CAR. A Kaplan-Meier survival curve demonstrated increasingly improved survival for mice treated with increasing doses of T cells expressing the anti-IL-13Rα2 CAR (FIG. 4B). The vehicle control had 0% survival rate at 25 days. However, mice that received $2 \times 10^6$ of the CD8+ T-cells expressing the IL13Rα2 Ab01 VLVH had ~50% survival after 90 days.

Example 5—In Vivo Anti-Tumor Activity of an Anti-IL13Rα2 CAR

To assess the impact of the IL13Ra2 Ab01 VLVH CAR spacer, a experiment substantially similar to Example 3 was performed using U251T tumor-bearing mice as glioblastoma model. On day 0, U251T GFP:ffluc tumor cells were injected intracranially followed by an intratumoral CD8+ CAR T-cell or Cd8+ Mock T-cells injection on day 7. Mice injected with Mock T-cells served as control.

All mice treated with IL13Rα2 Ab01 VLVH 2G short CAR T-cells showed complete tumor regression. Only one of the CAR-medium group of mice exhibited tumor relapse and necessitated animal euthanasia at day 58 after tumor injection. Three of the U251T tumor-bearing mice treated with intratumoral injection of long spacer IL13Ra2 CAR T-cells exhibited less therapeutic activity and tumor relapse.

Taken together, all these data suggest that the extracellular short spacer size is the optimal configuration for the IL3Rα2Ab01 VLVH conferring an optimal in vivo antitumor potency, supporting its clinical development.

TABLE 2 lists certain amino acid and nucleotide sequences for some embodiments of the methods and compositions provided herein.

TABLE 2

| SEQ ID NO: | Feature(s) | Sequence |
|---|---|---|
| SEQ ID NO: 01 | Human IgG1 | EPKSCDKTHTCPPCP |
| SEQ ID NO: 02 | Human IgG2 | ERKCCVECPPCP |
| SEQ ID NO: 03 | Human IgG3 | ELKTPLGDTHTCPRCPEPKSCDTPPPCPRCP EPKSCDTPPPCPRCPEPKSCDTPPPCPRCP |
| SEQ ID NO: 04 | Human IgG4 | ESKYGPPCPSCP |
| SEQ ID NO: 05 | Modified Human IgG4 | ESKYGPPCPPCP |
| SEQ ID NO: 06 | Modified Human IgG4 | YGPPCPPCP |
| SEQ ID NO: 07 | Modified Human IgG4 | KYGPPCPPCP |

TABLE 2-continued

| SEQ ID NO: | Feature(s) | Sequence |
|---|---|---|
| SEQ ID NO: 08 | Modified Human IgG4 | EVVKYGPPCPPCP |
| SEQ ID NO: 09 | S spacer | ESKYGPPCPPCP |
| SEQ ID NO: 10 | M spacer | ESKYGPPCPPCPGQPREPQVYTLPPSQEEMTKNQVSLT CLVKGFYPSDIAVEWESNGQPENNYKTTPPVLDSDGSF FLYSRLTVDKSRWQEGNVFSCSVMHEALHNHYTQKSLS LSLGK |
| SEQ ID NO: 11 | L spacer | ESKYGPPCPPCPAPEFLGGPSVFLFPPKPKDTLMISRTP EVTCVVVDVSQEDPEVQFNWYVDGVEVHNAKTKPREEQF NSTYRVVSVLTVLHQDWLNGKEYKCKVSNKGLPSSIEKT ISKAKGQPREPQVYTLPPSQEEMTKNQVSLTCLVKGFYP SDIAVEWESNGQPENNYKTTPPVLDSDGSFFLYSRLTVD KSRWQEGNVFSCSVMHEALHNHYTQKSLSLSLGK |
| SEQ ID NO: 12 | CD28tm | ATGTTCTGGGTGCTGGTGGTGGTCGGAGGC GTGCTGGCCTGCTACAGCCTGCTGGTCACCGTGGCCTT CATCATCTTTTGGGTG |
| SEQ ID NO: 13 | CD28tm | MFWVLVVVGGVLACYSLLVTVAFIIFWV |
| SEQ ID NO: 14 | Ab01-VH | EVQLVESGGGLVQPGGSLRLSCAASGFTFSRNGMSWVR QAPGKGLEWVATVSSGGSYIYYADSVKGRFTISRDNAK NSLYLQMNSLRAEDTAVYYCARQGTTALATRFFDVWGQ GTLVTVSS |
| SEQ ID NO: 15 | Ab02-VH | EVQLVESGGGLVQPGGSLRLSCAASGFTFTKYGVHWV RQAPGKGLEWVAVKWAGGSTDYNSALMSRFTISRDNA KNSLYLQMNSLRAEDTAVYYCARDHRDAMDYWGQGTL VTVSS |
| SEQ ID NO: 16 | Ab01-VL | DIQMTQSPSSLSASVGDRVTITCKASQDVGTAVAWYQQK PGKAPKLLIYSASYRSTGVPSRFSGSGSGTDFTLTISSL QPEDFATYYCQHHYSAPWTFGGGTKVEIK |
| SEQ ID NO: 17 | Ab02-VL | DIQMTQSPSSLSASVGDRVTITCTASLSVSSTYLHWYQ QKPGKAPKLLIYSTSNLASGVPSRFSGSGSGTDFTLTI SSLQPEDFATYYCHQYHRSPLTFGGGTKVEIK |
| SEQ ID NO: 18 | VH region | EVQLVESGGGLVQPGGSLRLSCAASGFTFSRNGMSWVR QAPGKGLEWVATVSSGGSYIYYADSVKGRFTISRDNAK NSLYLQMNSLRAEDTAVYYCARQGTTALATRFFDVWGQ GTLVTVSS |
| SEQ ID NO: 19 | VL region | DIQMTQSPSSLSASVGDRVTITCKASQDVGTAVAWYQQK PGKAPKLLIYSASYRSTGVPSRFSGSGSGTDFTLTISSL QPEDFATYYCQHHYSAPWTFGGGTKVEIK |
| SEQ ID NO: 20 | heavy chain CDR1 | SRNGMS |
| SEQ ID NO: 21 | heavy chain CDR2 | TVSSGGSYIYYADSVKG |
| SEQ ID NO: 22 | heavy chain CDR3 | QGTTALATRFFDV |
| SEQ ID NO: 23 | light chain CDR1 | KASQDVGTAVA |
| SEQ ID NO: 24 | light chain CDR2 | SASYRST |
| SEQ ID NO: 25 | light chain CDR3 | QHHYSAPWT |
| SEQ ID NO: 26 | Placeholder | |
| SEQ ID NO: 27 | Placeholder | |

TABLE 2-continued

| SEQ ID NO: | Feature(s) | Sequence |
|---|---|---|
| SEQ ID NO: 28 | heavy chain CDR2 | TVSSGGSYIYYADSVKG |
| SEQ ID NO: 29 | heavy chain CDR3 | QGTTALATRFFDV |
| SEQ ID NO: 30 | light chain CDR1 | KASQDVGTAVA |
| SEQ ID NO: 31 | light chain CDR2 | SASYRST |
| SEQ ID NO: 32 | light chain CDR3 | QHHYSAPWT |
| SEQ ID NO: 33 | heavy chain CDR1 | GFTFSRN |
| SEQ ID NO: 34 | heavy chain CDR1 | GFTFSRNGMS |
| SEQ ID NO: 35 | heavy chain CDR1 | RNGMS |
| SEQ ID NO: 36 | heavy chain CDR1 | SRNGMS |
| SEQ ID NO: 37 | heavy chain CDR2 | SSGGSY |
| SEQ ID NO: 38 | heavy chain CDR2 | TVSSGGSYIY |
| SEQ ID NO: 39 | heavy chain CDR2 | TVSSGGSYIY |
| SEQ ID NO: 40 | heavy chain CDR2 | TVSSGGSYIYYADSVKG |
| SEQ ID NO: 41 | heavy chain CDR3 | ARQGTTALATRFFDV |
| SEQ ID NO: 42 | Fc region | EVQLVESGGGLVQPGGSLRLSCAASGFTFSRNGMSWVR<br>QAPGKGLEWVATVSSGGSYIYYADSVKGRFTISRDNAKN<br>SLYLQMNSLRAEDTAVYYCARQGTTALATRFFDVWGQG<br>TLVTVSSASTKGPSVFPLAPSSKSTSGGTAALGCLVKDYF<br>PEPVTVSWNSGALTSGVHTFPAVLQSSGLYSLSSVVTVPS<br>SSLGTQTYICNVNHKPSNTKVDKKVEPKSCDKTHTCPPC<br>PAPELLGGPSVFLFPPKPKDTLMISRTPEVTCVWDVSHE<br>DPEVKFNWYVDGVEVHNAKTKPREEQYNSTYRVVSVLT<br>VLHQDWLNGKEYKCKVSNKALPAPIEKTISKAKGQPREP<br>QVYTLPPSREEMTKNQVSLTCLVKGFYPSDIAVEWESNG<br>QPENNYCTTPPVLDSDGSFFLYSKLTVDKSRWQQGNVFS<br>CSVMHEALHNHYTQKSLSCSPGK |
| SEQ ID NO: 43 | Fc region | EVQLVESGGGLVQPGGSLRLSCAASGFTFSRNGMSWVR<br>QAPGKGLEWVATVSSGGSYIYYADSVKGRFTISRDNAKN<br>SLYLQMNSLRAEDTAVYYCARQGTTALATRFFDVWGQG<br>TLVTVSSASTKGPSVFPLAPSSKSTSGGTAALGCLVKDYF<br>PEPVTVSWNSGALTSGVHTFPAVLQSSGLYSLSSVVTVPS<br>SSLGTQTYICNVNHKPSNTKVDKKVEPKSCDKTHTCPPC<br>PAPELLGGPSVFLFPPKPKDTLMISRTPEVTCVVVDVSHE<br>DPEVKFNWYVDGVEVHNAKTKPREEQYNSTYRVVSVLT<br>VLHQDWLNGKEYKCKVSNKALPAPIEKTISKAKGQPREP<br>QVYTLPPSREEMTKNQVSLTCLVKGFYPSDIAVEWESNG<br>QPENNYKTTPPVLDSDGSFFLYSKLTVDKSRWQQGNCFS<br>CSVMHEALHNHYTQKSLSCSPGK |
| SEQ ID NO: 44 | Fc region | EVQLVrESGGGLVQPGGSLRLSCAASGFTFSRNGMSW\R<br>QAPGKGLEWVATVSSGGSYIYYADSVKGRFTISRDNAKN<br>SLYLQMNSLRAEDTAVYYCARQGTTALATRFFDVWGQG<br>TLVTVSSASTKGPSVFPLAPSSKSTSGGTAALGCLVKDYF<br>PEPVTVSWNSGALTSGVHTFPAVLQSSGLYSLSSVVTVPS<br>SSLGTQTYICNVNHKPSNTKVDKKVEPKSCDKTHTCPPC<br>PAPELLGGPSVFLFPPKPKDTLMISRTPEVTCVVVDVSHE<br>DPEVKFNWYVDGVEVHNAKTKPREEQYNSTYRVVSVLT<br>VLHQDWLNGKEYKCKVSNKALPAPIEKTISKAKGQPREP |

TABLE 2-continued

| SEQ ID NO: | Feature(s) | Sequence |
|---|---|---|
| | | QVYTLPPSREEMTKNQVSLTCLVKGFYPSDIAVEWESNG QPENNYKTTPPVLDSDGSFFLYSKLTVDKSRWQQGNVFS CSVMHEALHNHYTQKSLSCSPGK |
| SEQ ID NO: 45 | Fc region | EVQLVESGGGLVQPGGSLRLSCAASGFTFSRNGMSWVR QAPGKGLEWVATVSSGGSYIYYADSVKGRFTISRDNAKN SLYLQMNSLRAEDTAVYYCARQGTTALATRFFDVWGQG TLVTVSSASTKGPSVFPLAPSSKSTSGGTAALGCLVKDYF PEPVTVSWNSGALTSGVHTFPAVLQSSGLYSLSSVVTVPS SSLGTQTYICNVNHKPSNTKVDKKVEPKSCDKTHTCPPC PAPELLGGPSVTLFPPKPKDTLMISRTPEVTCVVVDVSHE DPEVKFNWYVDGVEVHNAKTKPREEQYNSTYRWSVLT VLHQDWLNGKEYKCKVSNKALPAPIEKTISKAKGQPREP CVYTLPPSREEMTKNQVSLTCLVKGFYPSDIAVEWESNG QPENNYKTTPPVLDSDGSFFLYSKLTVDKSRWQQGNVFS CSVMHEALHNHYTQKSLSL |
| SEQ ID NO: 46 | Fc region | DIQMTQSPSSLSASVGDRVTITCKASQDVGTAVAWYQQK PGKAPKLLIYSASYRSTGVPSRFSGSGSGTDFTLTISSL QPEDFATYYCQHHYSAPWTFGGGTKVEIKRTVAAPSVFI FPPSDEQLKSGTASVVCLLNNFYPREAKVQWKVDNALQS GNSQESVTEQDSKDSTYSLSSTLTLSCADYEKHKVYACE VTHQGLSSPVTKSFNRGEC |
| SEQ ID NO: 47 | Fc region | DIQMTQSPSSLSASVGDRVTITCKASQDVGTAVAWYQQK PGKAPKLLIYSASYRSTGVTSRFSGSGSGTDFTLTISSL QPEDFATYYCQHHYSAPWTFGGGTKVEIKRTVACPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC |
| SEQ ID NO: 48 | Fc region | TVAAPSVFIFPPSDEQLKSGTASVVCLLNNFYPREAKVQ WKVDNALQSGNSQESVTEQDSKDSTYSLSSTLTLSKAAY EKHKVYACEVTHQGLSSPVTKSFNRGEC |
| SEQ ID NO: 49 | LCDR1 | TASLSVSSTYLH |
| SEQ ID NO: 50 | LCDR2 | STSNLAS |
| SEQ ID NO: 51 | LCDR3 | HQYHRSPLT |
| SEQ ID NO: 52 | LCDR1 | KASQDVGTAVA |
| SEQ ID NO: 53 | LCDR2 | SASYRST |
| SEQ ID NO: 54 | LCDR3 | QHHYSAPWT |
| SEQ ID NO: 55 | HCDR1 | TKYGVH |
| SEQ ID NO: 56 | HCDR2 | VKWAGGSTDYNSALMS |
| SEQ ID NO: 57 | HCDR3 | DHRDAMDY |
| SEQ ID NO: 58 | HCDR1 | SRNGMS |
| SEQ ID NO: 59 | HCDR2 | TVSSGGSYIYYADSVKG |
| SEQ ID NO: 60 | HCDR3 | QGTTALATRFFDV |
| SEQ ID NO: 61 | IL13Ra2 Ab01 VLVH scFv | GCTAGCCCGCCACCATGCTTCTCCTGGTGACAAGCCTT CTGCTCTGTGAGTTACCACACCCAGCATTCCTCCTGAT CCCAGACATCCAGATGACCCAGTCCCCCTCTTCTCTGT CTGCCTCTGTGGGCGACAGAGTGACCATCACCTGTAAG GCCAGTCAGGATGTAGGTACTGCTGTAGCCTGGTATCA GCAGAAGCCTGGCAAGGCTCCCAAGCTGCTGATCTAC |

TABLE 2-continued

| SEQ ID NO: | Feature(s) | Sequence |
|---|---|---|
| | | TCGGCATCCTACCGGTCCACTGGCGTGCCTTCCAGATT CTCCGGCTCTGGCTCTGGCACCGATTTCACCCTGACCA TCTCCTCCCTCCAGCCTGAGGATTTCGCCACCTACTAC TGCCAGCACCATTATAGTGCTCCGTGGACGTTTGGCGG CGGAACAAAGGTGGAGATCAAGGGTGGTGGTGGTTCT GGCGGCGGCGGCTCCGGTGGTGGTGGTTCTGAGGTGC AGCTGGTGGAGTCTGGCGGCGGACTGGTGCAGCCTGG CGGCTCTCTGAGACTGTCTTGTGCCGCCTCCGGCTTCA CCTTCAGTAGGAATGGCATGTCTTGGGTGAGGCAGGC CCCTGGCAAGGGCCTGGAGTGGGTGGCCACCGTTAGT AGTGGTGGTAGTTACATCTACTATGCAGACAGTGTGAA GGGGCGGTTCACCATCTCCAGGGACAACGCCAAGAAC TCCCTGTACCTCCAGATGAACTCCCTGAGGGCCGAGGA TACCGCCGTGTACTACTGTGCCAGACAAGGGACTACG GCACTAGCTACGAGGTTCTTCGATGTCTGGGGCCAGGG CACCCTGGTGACCGTGTCCTCTGAATCTAAGTACGGAC CG |
| SEQ ID NO: 62 | IL13Ra2 Ab01 VHVL scFv: Ab01-VL; Ab01-VH; ATG start codon; 5' NheI restriction site (GCTAGC); 3' RsrII restriction site (CGGACCG) | GCTAGCCCGCCACCATGCTTCTCCTGGTGACAAGCCTT CTGCTCTGTGAGTTACCACACCCAGCATTCCTCCTGAT CCCAGAGGTGCAGCTGGTGGAGTCTGGCGGCGGACTG GTGCAGCCTGGCGGCTCTCTGAGACTGTCTTGTGCCGC CTCCGGCTTCACCTTCAGTAGGAATGGCATGTCTTGGG TGAGGCAGGCCCCTGGCAAGGGCCTGGAGTGGGTGGC CACCGTTAGTAGTGGTGGTAGTTACATCTACTATGCAG ACAGTGTGAAGGGGCGGTTCACCATCTCCAGGGACAA CGCCAAGAACTCCCTGTACCTCCAGATGAACTCCCTGA GGGCCGAGGATACCGCCGTGTACTACTGTGCCAGACA AGGGACTACGGCACTAGCTACGAGGTTCTTCGATGTCT GGGGCCAGGGCACCCTGGTGACCGTGTCCTCTGGTGGT GGTGGTTCTGGCGGCGGCGGCTCCGGTGGTGGTGGTTC TGACATCCAGATGACCCAGTCCCCCTCTTCTCTGTCTG CCTCTGTGGGCGACAGAGTGACCATCACCTGTAAGGC CAGTCAGGATGTAGGTACTGCTGTAGCCTGGTATCAGC AGAAGCCTGGCAAGGCTCCCAAGCTGCTGATCTACTC GGCATCCTACCGGTCCACTGGCGTGCCTTCCAGATTCT CCGGCTCTGGCTCTGGCACCGATTTCACCCTGACCATC TCCTCCCTCCAGCCTGAGGATTTCGCCACCTACTACTG CCAGCACCATTATAGTGCTCCGTGGACGTTTGGCGGCG GAACAAAGGTGGAGATCAAGGAATCTAAGTACGGACC G |
| SEQ ID NO: 63 | IL13Ra2 Ab02 VLVH scFv | GCTAGCCCGCCACCATGCTTCTCCTGGTGACAAGCCTT CTGCTCTGTGAGTTACCACACCCAGCATTCCTCCTGAT CCCAGATATTCAGATGACCCAGAGCCCCGAGCAGCTG AGCGCGAGCGTGGGCGATCGCGTGACCATTACCTGCA CCGCGAGCCTGAGCGTGAGCAGCACCTATCTGCATTG GTATCAGCAGAAACCGGGCAAAGCGCCGAAACTGCTG ATTTATAGCACCAGCAACCTGGCGAGCGGCGTGCCGA GCCGCTTTAGCGGCAGCGGCAGCGGCACCGATTTTACC CTGACCATTAGCAGCCTGCAGCCGGAAGATTTTGCGAC CTATTATTGCCATCAGTATCATCGCAGCCCGCTGACCT TTGGCGGCGGCACCAAAGTGGAAATTAAAGGTGGTGG TGGTTCTGGCGGCGGCGGCTCCGGTGGTGGTGGTTCTG AAGTGCAGCTGGTGGAAAGCGGCGGCGGCCTGGTGCA GCCGGGCGGCAGCCTGCGCCTGAGCTGCGCGGCGAGC GGCTTTACCTTTACCAAATATGGCGTGCATTGGGTGCG CCAGGCGCCGGGCAAAGGCCTGGAATGGGTGGCGGTG AAATGGGCGGGCGGCAGCACCGATTATAACAGCGCGC TGATGAGCCGCTTTACCATTAGCCGCGATAACGCGAA AAACAGCCTGTATCTGCAGATGAACAGCCTGCGCGCG GAAGATACCGCCGTGTATTATTGCGCGCGCGATCATCG CGATGCGATGGATTATTGGGGCCAGGGCACCCTGGTG ACCGTGAGCAGCGAATCTAAGTACGGACCG |

TABLE 2-continued

| SEQ ID NO: | Feature(s) | Sequence |
|---|---|---|
| SEQ ID NO: 64 | IL13Ra2 Ab02 VHVL scFv: Ab02-VL; Ab02-VH; ATG start codon; 5' NheI restriction site (GCTAGC); 3' RsrII restriction site (CGGACCG) | GCTAGCCCGCCACCATGCTTCTCCTGGTGACAAGCCTT CTGCTCTGTGAGTTACCACACCCAGCATTCCTCCTGAT CCCAGAAGTGCAGCTGGTGGAAAGCGGCGGCGGCCTG GTGCAGCCGGGCGGCAGCCTGCGCCTGAGCTGCGCG CGAGCGGCTTTACCTTTACCAAATATGGCGTGCATTGG GTGCGCCAGGCGCCGGGCAAAGGCCTGGAATGGGTGG CGGTGAAATGGGCGGGCGGCAGCACCGATTATAACAG CGCGCTGATGAGCCGCTTTACCATTAGCCGCGATAACG CGAAAAACAGCCTGTATCTGCAGATGAACAGCCTGCG CGCGGAAGATACCGCGGTGTATTATTGCGCGCGCGAT CATCGCGATGCGATGGATTATTGGGGCCAGGGCACCC TGGTGACCGTGAGCAGCGGTGGTGGTGGTTCTGGCGG CGGCGGCTCCGGTGGTGGTGGTTCTGATATTCAGATGA CCCAGAGCCCGAGCAGCCTGAGCGCGAGCGTGGGCGA TCGCGTGACCATTACCTGCACCGCGAGCCTGAGCGTGA GCAGCACCTATCTGCATTGGTATCAGCAGAAACCGGG CAAAGCGCCGAAACTGCTGATTTATAGCACCAGCAAC CTGGCGAGCGGCGTGCCGAGCCGCTTTAGCGGCAGCG GCAGCGGCACCGATTTTACCCTGACCATTAGCAGCCTG CAGCCGGAAGATTTTGCGACCTATTATTGCCATCAGTA TCATCGCAGCCCGCTGACCTTTGGCGGCGGCACCAAA GTGGAAATTAAAGAATCTAAGTACGGACCG |
| SEQ ID NO: 65 | Ab01-VH | EVQLVESGGGLVQPGGSLRLSCAASGFTFSRNGMSWVR QAPGKGLEWVATVSSGGSYIYYADSVKGRFTISRDNAKN SLYLQMNSLRAEDTAVYYCARQGTTALATRFFDVWGQG TLVTVSS |
| SEQ ID NO: 66 | Ab01 HCDR1 | SRNGMS |
| SEQ ID NO: 67 | Ab01 HCDR2 | TVSSGGSYIYYADSVKG |
| SEQ ID NO: 68 | Ab01 HCDR3 | QGTTALATRFFDV |
| SEQ ID NO: 69 | Ab01-VL | DIQMTQSPSSLSASVGDRVTITCKASQDVGTAVAWYQQK PGKAPKLLIYSASYRSTGVPSRFSGSGSGTDFTLTISSL QPEDFATYYCQHHYSAPWTFGGGTKVEIK |
| SEQ ID NO: 70 | Ab01 LCDR1 | KASQDVGTAVA |
| SEQ ID NO: 71 | Ab01 LCDR2 | SASYRST |
| SEQ ID NO: 72 | Ab01 LCDR3 | QHHYSAPWT |
| SEQ ID NO: 73 | Ab02-VH | EVQLVESGGGLVQPGGSLRLSCAASGFTFTKYGVHWVR QAPGKGLEWVAVKWAGGSTDYNSALMSRFTISRDNAK NSLYLQMNSLRAEDTAVYYCARDHRDAMDYWGQGTLV TVSS |
| SEQ ID NO: 74 | Ab02 HCDR1 | TKYGVH |
| SEQ ID NO: 75 | Ab02 HCDR2 | VKWAGGSTDYNSALMS |
| SEQ ID NO: 76 | Ab02 HCDR3 | DHRDAMDY |
| SEQ ID NO: 77 | Ab02-VL | DIQMTQSPSSLSASVGDRVTITCTASLSVSSTYLHWYQQK PGKAPKLLIYSTSNLASGVPSRFSGSGSGTDFTLTISSL QPEDFATYYCHQYHRSPLTFGGGTKVEIK |
| SEQ ID NO: 78 | Ab02 LCDR1 | TASLSVSSTYLH |
| SEQ ID NO: 79 | Ab02 LCDR2 | STSNLAS |
| SEQ ID NO: 80 | Ab02 LCDR3 | HQYHRSPLT |

TABLE 2-continued

| SEQ ID NO: | Feature(s) | Sequence |
|---|---|---|
| SEQ ID NO: 81 | DHFRdm | MVGSLNCIVAVSQNMGIGKNGDFPWPPLRNESRYFQRM<br>TTTSSVEGKQNLVIMGKKTWFSIPEKNRPLKGRINLVLSR<br>ELKEPPQGAHFLSRSLDDALKLTEQPELANKVDMVWIVG<br>GSSVYKEAMNHPGHLKLFVTRIMQDFESDTFFPEIDLEKY<br>KLLPEYPGVLSDVQEEKGIKYKFEVYEKND |
| SEQ ID NO: 82 | DHFRdm | ATGGTTGGTTCGCTAAACTGCATCGTCGCTGTGTCCCA<br>GAACATGGGCATCGGCAAGAACGGGGACTTCCCCTGG<br>CCACCGCTCAGGAATGAATCCAGATATTTCCAGAGAA<br>TGACCACAACCTCTTCAGTAGAAGGTAAACAGAATCT<br>GGTGATTATGGGTAAGAAGACCTGGTTCTCCATTCCTG<br>AGAAGAATCGACCTTTAAAGGGTAGAATTAATTTAGTT<br>CTCAGCAGAGAACTCAAGGAACCTCCACAAGGAGCTC<br>ATTTTCTTTCCAGAAGTCTAGATGATGCCTTAAAACTT<br>ACTGAACAACCAGAATTAGCAAATAAAGTAGACATGG<br>TCTGGATAGTTGGTGGCAGTTCTGTTTATAAGGAAGCC<br>ATGAATCACCCAGGCCATCTTAAACTATTTGTGACAAG<br>GATCATGCAAGACTTTGAAAGTGACACGTTTTTTCCAG<br>AAATTGATTTGGAGAAATATAAACTTCTGCCAGAATAC<br>CCAGGTGTTCTCTCTGATGTCCAGGAGGAGAAAGGCA<br>TTAAGTACAAATTTGAAGTATATGAGAAGAATGATTA<br>A |
| SEQ ID NO: 83 | GMCSFss Leader | ATGCTTCTCCTGGTGACAAGCCTTCTGCTCTGTGAGTT<br>ACCACACCCAGCATTCCTCCTGATCCCA |
| SEQ ID NO: 84 | Ab01-VL | GACATCCAGATGACCCAGTCCCCCTCTTCTCTGTCTGC<br>CTCTGTGGGCGACAGAGTGACCATCACCTGTAAGGCC<br>AGTCAGGATGTAGGTACTGCTGTAGCCTGGTATCAGCA<br>GAAGCCTGGCAAGGCTCCCAAGCTGCTGATCTACTCG<br>GCATCCTACCGGTCCACTGGCGTGCCTTCCAGATTCTC<br>CGGCTCTGGCTCTGGCACCGATTTCACCCTGACCATCT<br>CCTCCCTCCAGCCTGAGGATTTCGCCACCTACTACTGC<br>CAGCACCATTATAGTGCTCCGTGGACGTTTGGCGGCGG<br>AACAAAGGTGGAGATCAAG |
| SEQ ID NO: 85 | Ab01-VH | GAGGTGCAGCTGGTGGAGTCTGGCGGCGGACTGGTGC<br>AGCCTGGCGGCTCTCTGAGACTGTCTTGTGCCGCCTCC<br>GGCTTCACCTTCAGTAGGAATGGCATGTCTTGGGTGAG<br>GCAGGCCCCTGGCAAGGGCCTGGAGTGGGTGGCCACC<br>GTTAGTAGTGGTGGTAGTTACATCTACTATGCAGACAG<br>TGTGAAGGGGCGGTTCACCATCTCCAGGGACAACGCC<br>AAGAACTCCCTGTACCTCCAGATGAACTCCCTGAGGGC<br>CGAGGATACCGCCGTGTACTACTGTGCCAGACAAGGG<br>ACTACGGCACTAGCTACGAGGTTCTTCGATGTCTGGGG<br>CCAGGGCACCCTGGTGACCGTGTCCTCT |
| SEQ ID NO: 86 | Ab02-VL | GATATTCAGATGACCCAGAGCCCGAGCAGCCTGAGCG<br>CGAGCGTGGGCGATCGCGTGACCATTACCTGCACCGC<br>GAGCCTGAGCGTGAGCAGCACCTATCTGCATTGGTATC<br>AGCAGAAACCCGGGCAAAGCGCCGAAACTGCTGATTTA<br>TAGCACCAGCAACCTGGCGAGCGGCGTGCCGAGCCGC<br>TTTAGCGGCAGCGGCAGCGGCACCGATTTTACCCTGAC<br>CATTAGCAGCCTGCAGCCGGAAGATTTTGCGACCTATT<br>ATTGCCATCAGTATCATCGCAGCCCGCTGACCTTTGGC<br>GGCGGCACCAAAGTGGAAATTAAA |
| SEQ ID NO: 87 | Ab02-VH | GAAGTGCAGCTGGTGGAAAGCGGCGGCGGCCTGGTGC<br>AGCCGGGCGGCAGCCTGCGCCTGAGCTGCGCGGCGAG<br>CGGCTTTACCTTTACCAAATATGGCGTGCATTGGGTGC<br>GCCAGGCGCCGGGCAAAGGCCTGGAATGGGTGGCGGT<br>GAAATGGCGGGCGGCAGCACCGATTATAACAGCGCG<br>CTGATGAGCCGCTTTACCATTAGGCGCGATAACGCGAA<br>AAACAGCCTGTATCTGCAGATGAACAGCCTGCGCGCG<br>GAAGATACCGCGGTGTATTATTGCGCGCGCGATCATCG<br>CGATGCGATGGATTATTGGGGCCAGGGCACCCTGGTG<br>ACCGTGAGCAGC |
| SEQ ID NO: 88 | (Gly-Gly-Gly-Ser)x3 linker | GGTGGTGGTGGTTCTGGCGGCGGCGGCTCCGGTGGTG<br>GTGGTTCT |
| SEQ ID NO: 89 | Ab01 scFv VLVH | GACATCCAGATGACCCAGTCCCCCTCTTCTCTGTCTGC<br>CTCTGTGGGCGACAGAGTGACCATCACCTGTAAGGCC<br>AGTCAGGATGTAGGTACTGCTGTAGCCTGGTATCAGCA<br>GAAGCCTGGCAAGGCTCCCAAGCTGCTGATCTACTCG<br>GCATCCTACCGGTCCACTGGCGTGCCTTCCAGATTCTC<br>CGGCTCTGGCTCTGGCACCGATTTCACCCTGACCATCT |

TABLE 2-continued

| SEQ ID NO: | Feature(s) | Sequence |
|---|---|---|
| | | CCTCCCTCCAGCCTGAGGATTTCGCCACCTACTACTGC CAGCACCATTATAGTGCTCCGTGGACGTTTGGCGGCGG AACAAAGGTGGAGATCAAGGGTGGTGGTGGTTCTGGC GGCGGCGGCTCCGGTGGTGGTGGTTCTGAGGTGCAGC TGGTGGAGTCTGGCGGCGGACTGGTGCAGCCTGGCGG CTCTCTGAGACTGTCTTGTGCCGCCTCCGGCTTCACCTT CAGTAGGAATGGCATGTCTTGGGTGAGGCAGGCCCCT GGCAAGGGCCTGGAGTGGGTGGCCACCGTTAGTAGTG GTGGTAGTTACATCTACTATGCAGACAGTGTGAAGGG GCGGTTCACCATCTCCAGGGACAACGCCAAGAACTCC CTGTACCTCCAGATGAACTCCCTGAGGGCCGAGGATA CCGCCGTGTACTACTGTGCCAGACAAGGGACTACGGC ACTAGCTACGAGGTTCTTCGATGTCTGGGGCCAGGGCA CCCTGGTGACCGTGTCCTCT |
| SEQ ID NO: 90 | Ab01 scFv VHVL | GAGGTGCAGCTGGTGGAGTCTGGCGGCGGACTGGTGC AGCCTGGCGGCTCTCTGAGACTGTCTTGTGCCGCCTCC GGCTTCACCTTCAGTAGGAATGGCATGTCTTGGGTGAG GCAGGCCCCTGGCAAGGGCCTGGAGTGGGTGGCCACC GTTAGTAGTGGTGGTAGTTACATCTACTATGCAGACAG TGTGAAGGGGCGGTTCACCATCTCCAGGGACAACGCC AAGAACTCCCTGTACCTCCAGATGAACTCCCTGAGGGC CGAGGATACCGCCGTGTACTACTGTGCCAGACAAGGG ACTACGGCACTAGCTACGAGGTTCTTCGATGTCTGGGG CCAGGGCACCCTGGTGACCGTGTCCTCTGGTGGTGGTG GTTCTGGCGGCGGCGGCTCCGGTGGTGGTGGTTCTGAC ATCCAGATGACCCAGTCCCCCTCTTCTCTGTCTGCCTCT GTGGGCGACAGAGTGACCATCACCTGTAAGGCCAGTC AGGATGTAGGTACTGCTGTAGCCTGGTATCAGCAGAA GCCTGGCAAGGCTCCCAAGCTGCTGATCTACTCGGCAT CCTACCGGTCCACTGGCGTGCCTTCCAGATTCTCCGGC TCTGGCTCTGGCACCGATTTCACCCTGACCATCTCCTC CCTCCAGCCTGAGGATTTCGCCACCTACTACTGCCAGC ACCATTATAGTGCTCCGTGGACGTTTGGCGGCGGAACA AAGGTGGAGATCAAG |
| SEQ ID NO: 91 | Ab02 scFv VLVH | GATATTCAGATGACCCAGAGCCCCGAGCAGCCTGAGCG CGAGCGTGGGCGATCGCGTGACCATTACCTGCACCGC GAGCCTGAGCGTGAGCAGCACCTATCTGCATTGGTATC AGCAGAAACCGGGCAAAGCGCCGAAACTGCTGATTTA TAGCACCAGCAACCTGGCGAGCGGCGTGCCGAGCCGC TTTAGCGGCAGCGGCAGCGGCACCGATTTTACCCTGAC CATTAGCAGCCTGCAGCCGGAAGATTTTGCGACCTATT ATTGCCATCAGTATCATCGCAGCCCGCTGACCTTTGGC GGCGGCACCAAAGTGGAAATTAAAGGTGGTGGTGGTT CTGGCGGCGGCGGCTCCGGTGGTGGTGGTTCTGAAGT GCAGCTGGTGGAAAGCGGCGGCGGCCTGGTGCAGCCG GGCGGCAGCCTGCGCCTGAGCTGCGCGGCGAGCGGCT TTACCTTTACCAAATATGGCGTGCATTGGGTGCGCCAG GCGCCGGGCAAAGGCCTGGAATGGGTGGCGGTGAAAT GGGCGGGCGGCAGCACCGATTATAACAGCGCGCTGAT GAGCCGCTTTACCATTAGCCGCGATAACGCGAAAAAC AGCCTGTATCTGCAGATGAACAGCCTGCGCGCGGAAG ATACCGCGGTGTATTATTGCGCGCGCGATCATCGCGAT GCGATGGATTATTGGGGCCAGGGCACCCTGGTGACCG TGAGCAGC |
| SEQ ID NO: 92 | Ab02 scFv VHVL | GAAGTGCAGCTGGTGGAAAGCGGCGGCGGCCTGGTGC AGCCGGGCGGCAGCCTGCGCCTGAGCTGCGCGGCGAG CGGCTTTACCTTTACCAAATATGGCGTGCATTGGGTGC GCCAGGCGCCGGGCAAAGGCCTGGAATGGGTGGCGGT GAAATGGGCGGCGGCAGCACCGATTATAACAGCGCG CTGATGAGCCGCTTTACCATTAGCCGCGATAACGCGAA AAACAGCCTGTATCTGCAGATGAACAGCCTGCGCGCG GAAGATACCGCGGTGTATTATTGCGCGCGCGATCATCG CGATGCGATGGATTATTGGGGCCAGGGCACCCTGGTG ACCGTGAGCAGCGGTGGTGGTGGTTCTGGCGGCGGCG GCTCCGGTGGTGGTGGTTCTGATATTCAGATGACCCAG AGCCCCGAGCAGCCTGAGCGCGAGCGTGGGCGATCGCG TGACCATTACCTGCACCGCGAGCCTGAGCGTGAGCAG CACCTATCTGCATTGGTATCAGCAGAAACCGGGCAAA GCGCCGAAACTGCTGATTTATAGCACCAGCAACCTGG CGAGCGGCGTGCCGAGCCGCTTTAGCGGCAGCGGCAG CGGCACCGATTTTACCCTGACCATTAGCAGCCTGCAGC CGGAAGATTTTGCGACCTATTATTGCCATCAGTATCAT CGCAGCCCGCTGACCTTTGGCGGCGGCACCAAAGTGG AAATTAAA |

TABLE 2-continued

| SEQ ID NO: | Feature(s) | Sequence |
|---|---|---|
| SEQ ID NO: 93 | S spacer | GAATCTAAGTACGGACCGCCCTGCCCCCCTTGCCCT |
| SEQ ID NO: 94 | CD28tm | ATGTTCTGGGTGCTGGTGGTGGTCGGAGGCGTGCTGGC<br>CTGCTACAGCCTGCTGGTCACCGTGGCCTTCATCATCT<br>TTTGGGTG |
| SEQ ID NO: 95 | 41-BB | AAACGGGGCAGAAAGAAACTCCTGTATATATTCAAAC<br>AACCATTTATGAGACCAGTACAAACTACTCAAGAGGA<br>AGATGGCTGTAGCTGCCGATTTCCAGAAGAAGAAGAA<br>GGAGGATGTGAACTG |
| SEQ ID NO: 96 | CD3ζ | CGGGTGAAGTTCAGCAGAAGCGCCGACGCCCCTGCCT<br>ACCAGCAGGGGCAGAATCAGCTGTACAACGAGCTGAA<br>CCTGGGCAGAAGGGAAGAGTACGACGTCCTGGATAAG<br>CGGAGAGGCCGGGACCCTGAGATGGGCGGCAAGCCTC<br>GGCGGAAGAACCCCCAGGAAGGCCTGTATAACGAACT<br>GCAGAAAGACAAGATGGCCGAGGCCTACAGCGAGATC<br>GGCATGAAGGGCGAGCGGAGGCGGGGCAAGGGCCAC<br>GACGGCCTGTATCAGGGCCTGTCCACCGCCACCAAGG<br>ATACCTACGACGCCCTGCACATGCAGGCCCTGCCCCCA<br>AGG |
| SEQ ID NO: 97 | T2A | CTCGAGGGCGGCGGAGAGGGCAGAGGAAGTCTTCTAA<br>CATGCGGTGACGTGGAGGAGAATCCCGGCCCTAGG |
| SEQ ID NO: 98 | EGFRt | CGCAAAGTGTGTAACGGAATAGGTATTGGTGAATTTA<br>AAGACTCACTCTCCATAAATGCTACGAATATTAAACAC<br>TTCAAAAACTGCACCTCCATCAGTGGCGATCTCCACAT<br>CCTGCCGGTGGCATTTAGGGGTGACTCCTTCACACATA<br>CTCCTCCTCTGGATCCACAGGAACTGGATATTCTGAAA<br>ACCGTAAAGGAAATCACAGGGTTTTTGCTGATTCAGGC<br>TTGGCCTGAAAACAGGACGGACCTCCATGCCTTTGAG<br>AACCTAGAAATCATACGCGGCAGGACCAAGCAACATG<br>GTCAGTTTTCTCTTGCAGTCGTCAGCCTGAACATAACA<br>TCCTTGGGATTACGCTCCCTCAAGGAGATAAGTGATGG<br>AGATGTGATAATTTCAGGAAACAAAAATTTGTGCTATG<br>CAAATACAATAAACTGGAAAAAACTGTTTGGGACCTC<br>CGGTCAGAAAACCAAAATTATAAGCAACAGAGGTGAA<br>AACAGCTGCAAGGCCACAGGCCAGGTCTGCCATGCCT<br>TGTGCTCCCCCGAGGGCTGCTGGGGCCCGGAGCCCAG<br>GGACTGCGTCTCTTGCCGGAATGTCAGCCGAGGCAGG<br>GAATGCGTGGACAAGTGCAACCTTCTGGAGGGTGAGC<br>CAAGGGAGTTTGTGGAGAACTCTGAGTGCATACAGTG<br>CCACCCAGAGTGCCTGCCTCAGGCCATGAACATCACCT<br>GCACAGGACGGGGACCAGACAACTGTATCCAGTGTGC<br>CCACTACATTGACGGCCCCCACTGCGTCAAGACCTGCC<br>CGGCAGGAGTCATGGGAGAAAACAACACCCTGGTCTG<br>GAAGTACGCAGACGCCGGCCATGTGTGCCACCTGTGC<br>CATCCAAACTGCACCTACGGATGCACTGGGCCAGGTCT<br>TGAAGGCTGTCCAACGAATGGGCCTAAGATCCCGTCC<br>ATCGCCACTGGGATGGTGGGGGCCCTCCTCTTGCTGCT<br>GGTGGTGGCCCTGGGGATCGGCCTCTTCATG |
| SEQ ID NO: 99 | DHFRdm | ATGGTTGGTTCGCTAAACTGCATCGTCGCTGTGTCCCA<br>GAACATGGGCATCGGCAAGAACGGGGACTTCCCCTGG<br>CCACCGCTCAGGAATGAATCCAGATATTTCCAGAGAA<br>TGACCACAACCTCTTCAGTAGAAGGTAAACAGAATCT<br>GGTGATTATGGGTAAGAAGACCTGGTTCTCCATTCCTG<br>AGAAGAATCGACCTTTAAAGGGTAGAATTAATTTAGTT<br>CTCAGCAGAGAACTCAAGGAACCTCCACAAGGAGCTC<br>ATTTTCTTTCCAGAAGTCTAGATGATGCCTTAAAACTT<br>ACTGAACAACCAGAATTAGCAAATAAAGTAGACATGG<br>TCTGGATAGTTGGTGGCAGTTCTGTTTATAAGGAAGCC<br>ATGAATCACCCAGGCCATCTTAAACTATTTGTGACAAG<br>GATCATGCAAGACTTTGAAAGTGACACGTTTTTTCCAG<br>AAATTGATTTGGAGAAATATAAACTTCTGCCAGAATAC<br>CCAGGTGTTCTCTCTGATGTCCAGGAGGAGAAAGGCA<br>TTAAGTACAAATTTGAAGTATATGAGAAGAATGATTA<br>A |
| SEQ ID NO: 100 | M spacer | GAATCTAAGTACGGACCGCCCTGCCCCCCTTGCCCTGG<br>CCAGCCTAGAGAACCCAGGTGTACACCCTGCCTCCCA<br>GCCAGGAAGAGATGACCAAGAACCAGGTGTCCCTGAC<br>CTGCCTGGTCAAAGGCTTCTACCCCAGCGATATCGCCG<br>TGGAATGGGAGAGCAACGGCCAGCCCGAGAACAACTA |

TABLE 2-continued

| SEQ ID NO: | Feature(s) | Sequence |
|---|---|---|
| | | CAAGACCACCCCCCCTGTGCTGGACAGCGACGGCAGC<br>TTCTTCCTGTACTCCCGGCTGACCGTGGACAAGAGCCG<br>GTGGCAGGAAGGCAACGTCTTCAGCTGCAGCGTGATG<br>CACGAGGCCCTGCACAACCACTACACCCAGAAGTCCC<br>TGAGCCTGAGCCTGGGCAAG |
| SEQ ID NO: 101 | L spacer | ATCTAAGTACGGACCGCCCTGCCCCCCTTGCCCTGCCC<br>CCGAGTTCGACGGCGGACCCAGCGTGTTCCTGTTCCCC<br>CCCAAGCCCAAGGACACCCTGATGATCAGCCGGACCC<br>CCGAGGTGACCTGCGTGGTGGTGGACGTGAGCCAGGA<br>AGATCCCGAGGTCCAGTTCAATTGGTACGTGGACGGC<br>GTGGAAGTGCACAACGCCAAGACCAAGCCCAGAGAGG<br>AACAGTTCCAGAGCACCTACCGGGTGGTGTCTGTGCTG<br>ACCGTGCTGCACCAGGACTGGCTGAACGGCAAAGAAT<br>ACAAGTGCAAGGTGTCCAACAAGGGCCTGCCCAGCAG<br>CATCGAAAAGACCATCAGCAAGGCCAAGGGCCAGCCT<br>CGCGAGCCCCAGGTGTACACCCTGCCTCCCTCCCAGGA<br>AGAGATGACCAAGAACCAGGTGTCCCTGACCTGCCTG<br>GTGAAGGGCTTCTACCCCAGCGACATCGCCGTGGAGT<br>GGGAGAGCAACGGCCAGCCTGAGAACAACTACAAGAC<br>CACCCCTCCCGTGCTGGACAGCGACGGCAGCTTCTTCC<br>TGTACAGCCGGCTGACCGTGGACAAGAGCCGGTGGCA<br>GGAAGGCAACGTCTTTAGCTGCAGCGTGATGCACGAG<br>GCCCTGCACAACCACTACACCCAGAAGAGCCTGAGCC<br>TGTCCCTGGGCAAG |

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those of skill within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

Any of the features of an embodiment of the first through eighth aspects is applicable to all aspects and embodiments identified herein. Moreover, any of the features of an embodiment of the first through eighth aspects is independently combinable, partly or wholly with other embodiments described herein in any way, e.g., one, two, or three or more embodiments may be combinable in whole or in part. Further, any of the features of an embodiment of the first through eighth aspects may be made optional to other aspects or embodiments.

What is claimed is:

1. A nucleic acid encoding a chimeric antigen receptor, the chimeric antigen receptor comprising:
   a ligand binding domain that binds to an IL-13 alpha 2 (IL13Rα2) receptor, wherein the ligand binding domain comprises:
   a heavy chain variable (VH) domain comprising
   a complementarity determining region (CDR) 1 having the amino acid sequence set forth in SEQ ID NO: 20;
   a CDR2 having the amino acid sequence set forth in SEQ ID NO: 21; and
   a CDR3 having the amino acid sequence set forth in SEQ ID NO: 22; and
   a light chain variable (VL) domain comprising
   a CDR1 having the amino acid sequence set forth in SEQ ID NO: 23;
   a CDR2 having the amino acid sequence set forth in SEQ ID NO: 24; and
   a CDR3 having the amino acid sequence set forth in SEQ ID NO: 25;
   a polypeptide spacer between the ligand binding domain and a transmembrane domain, the polypeptide spacer having at least 95% identity with the amino acid sequence of SEQ ID NO:09;
   the transmembrane domain; and
   an intracellular signaling region,
   wherein the transmembrane domain links the polypeptide spacer to the intracellular signaling region.

2. The nucleic acid of claim 1, wherein
   the amino acid sequence of the VH domain has at least 90% identity with the amino acid sequence set forth in SEQ ID NO: 18 and
   the amino acid sequence of the VL domain has at least 90% identity with the amino acid sequence of SEQ ID NO: 19.

3. The nucleic acid of claim 1, wherein
   the amino acid sequence of the VH domain has the amino acid sequence set forth in SEQ ID NO: 18 and
   the amino acid sequence of the VL domain has the amino acid sequence set forth in SEQ ID NO:19.

4. The nucleic acid of claim 1, wherein the ligand binding domain is an antigen-binding fragment of an antibody.

5. The nucleic acid of claim 1, wherein the ligand binding domain is a single chain variable fragment (scFv).

6. The nucleic acid of claim 5, wherein the scFv comprises a VL-VH orientation.

7. The nucleic acid of claim 5, wherein the scFv is encoded by a sequence having at least 95% identity with the nucleotide sequence set forth in SEQ ID NO: 61.

8. The nucleic acid of claim 5, wherein the scFv is encoded by the nucleotide sequence set forth in SEQ ID NO: 61.

9. The nucleic acid of claim 1, wherein the polypeptide spacer has a sequence set forth in SEQ ID NO: 09.

10. The nucleic acid of claim 1, wherein the intracellular signaling region comprises a primary signaling domain and a co-stimulatory signaling domain, wherein the primary signaling domain comprises all or a portion of a CD3 zeta signaling domain and the co-stimulatory signaling domain is selected from the group consisting of CD27, CD28, 4-1BB, OX-40, CD30, CD40, PD-1, ICOS, LFA-1, CD2, CD7, NKG2C, B7-H3, and combinations thereof.

11. The nucleic acid of claim 10, wherein the primary signaling domain is a portion of the CD3 zeta signaling domain and the co-stimulatory signaling domain is a portion of the 4-1BB signaling domain.

12. The nucleic acid of claim 1, wherein the transmembrane domain comprises a CD28 transmembrane domain.

13. The nucleic acid of claim 1, further comprising a sequence that encodes a marker protein.

14. The nucleic acid of claim 13, wherein the marker protein is a truncated epidermal growth factor receptor, a truncated human epidermal growth factor receptor 2, a truncated Cluster of Differentiation 19, or a dihydrofolate reductase (DHFR).

15. A pharmaceutical composition comprising a cell comprising the nucleic acid of claim 1, and a pharmaceutically acceptable carrier.

16. A method of treating cancer in a subject in need thereof, comprising: administering a therapeutically effective amount of the pharmaceutical composition of claim 15 to the subject.

* * * * *

SEQUENCE LISTING

<160> NUMBER OF SEQ ID NOS: 101

<210> SEQ ID NO 1
<211> LENGTH: 15
<212> TYPE: PRT
<213> ORGANISM: Artificial Sequence
<220> FEATURE:
<223> OTHER INFORMATION: Human IgG1

<400> SEQUENCE: 1

Glu Pro Lys Ser Cys Asp Lys Thr His Thr Cys Pro Pro Cys Pro
1               5                   10                  15

<210> SEQ ID NO 2
<211> LENGTH: 12
<212> TYPE: PRT
<213> ORGANISM: Artificial Sequence
<220> FEATURE:
<223> OTHER INFORMATION: Human IgG2

<400> SEQUENCE: 2

Glu Arg Lys Cys Cys Val Glu Cys Pro Pro Cys Pro
1               5                   10

<210> SEQ ID NO 3
<211> LENGTH: 61
<212> TYPE: PRT
<213> ORGANISM: Artificial Sequence
<220> FEATURE:
<223> OTHER INFORMATION: Human IgG3

<400> SEQUENCE: 3

Glu Leu Lys Thr Pro Leu Gly Asp Thr His Thr Cys Pro Arg Cys Pro
1               5                   10                  15

Glu Pro Lys Ser Cys Asp Thr Pro Pro Pro Cys Pro Arg Cys Pro Glu
            20                  25                  30

Pro Lys Ser Cys Asp Thr Pro Pro Pro Cys Pro Arg Cys Pro Glu Pro
        35                  40                  45

Lys Ser Cys Asp Thr Pro Pro Cys Pro Arg Cys Pro
    50                  55                  60

<210> SEQ ID NO 4
<211> LENGTH: 12
<212> TYPE: PRT
<213> ORGANISM: Artificial Sequence
<220> FEATURE:
<223> OTHER INFORMATION: Human IgG4

<400> SEQUENCE: 4

Glu Ser Lys Tyr Gly Pro Pro Cys Pro Ser Cys Pro
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Modified Human IgG4

<400> SEQUENCE: 5

Glu Ser Lys Tyr Gly Pro Pro Cys Pro Pro Cys Pro
1               5                   10

<210> SEQ ID NO 6
<211> LENGTH: 12

-continued

```
<212> TYPE: PRT
<213> ORGANISM: Artificial Sequence
<220> FEATURE:
<223> OTHER INFORMATION: Modified Human IgG4

<400> SEQUENCE: 6

Glu Ser Lys Tyr Gly Pro Pro Cys Pro Cys Pro
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Modified Human IgG4

<400> SEQUENCE: 7

Lys Tyr Gly Pro Pro Cys Pro Pro Cys Pro
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Modified Human IgG4

<400> SEQUENCE: 8

Glu Val Val Lys Tyr Gly Pro Pro Cys Pro Pro Cys Pro
1               5                   10

<210> SEQ ID NO 9
<211> LENGTH: 12
<212> TYPE: PRT
<213> ORGANISM: Artificial Sequence
<220> FEATURE:
<223> OTHER INFORMATION: S spacer

<400> SEQUENCE: 9

Glu Ser Lys Tyr Gly Pro Pro Cys Pro Pro Cys Pro
1               5                   10

<210> SEQ ID NO 10
<211> LENGTH: 119
<212> TYPE: PRT
<213> ORGANISM: Artificial Sequence
<220> FEATURE:
<223> OTHER INFORMATION: M spacer

<400> SEQUENCE: 10

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110
```

Leu Ser Leu Ser Leu Gly Lys
        115

<210> SEQ ID NO 11
<211> LENGTH: 229
<212> TYPE: PRT
<213> ORGANISM: Artificial Sequence
<220> FEATURE:
<223> OTHER INFORMATION: L spacer

<400> SEQUENCE: 11

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 12
<211> LENGTH: 84
<212> TYPE: DNA
<213> ORGANISM: Artificial Sequence
<220> FEATURE:
<223> OTHER INFORMATION: CD28tm

<400> SEQUENCE: 12
atgttctggg tgctggtggt ggtcggaggc gtgctggcct gctacagcct gctggtcacc      60
gtggccttca tcatcttttg ggtg                                            84

<210> SEQ ID NO 13
<211> LENGTH: 28
<212> TYPE: PRT
<213> ORGANISM: Artificial Sequence
<220> FEATURE:

<223> OTHER INFORMATION: CD28tm

<400> SEQUENCE: 13

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 14
<211> LENGTH: 122
<212> TYPE: PRT
<213> ORGANISM: Artificial Sequence
<220> FEATURE:
<223> OTHER INFORMATION: Ab01-VH

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Gly Met Ser Trp Val Arg Gln Ala Pro Gly Lys Gly Leu Glu Trp Val
        35                  40                  45

Ala Thr Val Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Thr Thr Ala Leu Ala Thr Arg Phe Phe Asp Val Trp
            100                 105                 110

Gly Gln Gly Thr Leu Val Thr Val Ser Ser
        115                 120

<210> SEQ ID NO 15
<211> LENGTH: 116
<212> TYPE: PRT
<213> ORGANISM: Artificial Sequence
<220> FEATURE:
<223> OTHER INFORMATION: Ab02-VH

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Lys Tyr
            20                  25                  30

Gly Val His Trp Val Arg Gln Ala Pro Gly Lys Gly Leu Glu Trp Val
        35                  40                  45

Ala Val Lys Trp Ala Gly Gly Ser Thr Asp Tyr Asn Ser Ala Leu Met
    50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp His Arg Asp Ala Met Asp Tyr Trp Gly Gln Gly Thr Leu Val
            100                 105                 110

Thr Val Ser Ser
        115

```
<210> SEQ ID NO 16
<211> LENGTH: 107
<212> TYPE: PRT
<213> ORGANISM: Artificial Sequence
<220> FEATURE:
<223> OTHER INFORMATION: Ab01-VL

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Ser Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Tyr Ser Ala Pro Trp
                85                  90                  95

Thr Phe Gly Gly Gly Thr Lys Val Glu Ile Lys
            100                 105

<210> SEQ ID NO 17
<211> LENGTH: 108
<212> TYPE: PRT
<213> ORGANISM: Artificial Sequence
<220> FEATURE:
<223> OTHER INFORMATION: Ab02-VL

<400> SEQUENCE: 17

Asp Ile Gln Met Thr Gln Ser Pro Ser Ser Leu Ser Ala Ser Val Gly
1               5                   10                  15

Asp Arg Val Thr Ile Thr Cys Thr Ala Ser Leu Ser Val Ser Ser Thr
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gly Gly Thr Lys Val Glu Ile Lys
            100                 105

<210> SEQ ID NO 18
<211> LENGTH: 122
<212> TYPE: PRT
<213> ORGANISM: Artificial Sequence
<220> FEATURE:
<223> OTHER INFORMATION: VH region

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Gly Met Ser Trp Val Arg Gln Ala Pro Gly Lys Gly Leu Glu Trp Val
        35                  40                  45
```

```
Ala Thr Val Ser Ser Gly Gly Ser Tyr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Gly Thr Thr Ala Leu Ala Thr Arg Phe Phe Asp Val Trp
            100                 105                 110

Gly Gln Gly Thr Leu Val Thr Val Ser Ser
            115                 120
```

<210> SEQ ID NO 19
<211> LENGTH: 107
<212> TYPE: PRT
<213> ORGANISM: Artificial Sequence
<220> FEATURE:
<223> OTHER INFORMATION: VL region

<400> SEQUENCE: 19

```
Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Gly Thr Ala
                 20                  25                  30

Val Ala Trp Tyr Gln Gln Lys Pro Gly Lys Ala Pro Lys Leu Leu Ile
             35                  40                  45

Tyr Ser Ala Ser Tyr Arg Ser Thr Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln His His Tyr Ser Ala Pro Trp
                 85                  90                  95

Thr Phe Gly Gly Gly Thr Lys Val Glu Ile Lys
            100                 105
```

<210> SEQ ID NO 20
<211> LENGTH: 6
<212> TYPE: PRT
<213> ORGANISM: Artificial Sequence
<220> FEATURE:
<223> OTHER INFORMATION: heavy chain CDR1

<400> SEQUENCE: 20

```
Ser Arg Asn Gly Met Ser
 1               5
```

<210> SEQ ID NO 21
<211> LENGTH: 17
<212> TYPE: PRT
<213> ORGANISM: Artificial Sequence
<220> FEATURE:
<223> OTHER INFORMATION: heavy chain CDR2

<400> SEQUENCE: 21

```
Thr Val Ser Ser Gly Gly Ser Tyr Ile Tyr Tyr Ala Asp Ser Val Lys
 1               5                  10                  15

Gly
```

<210> SEQ ID NO 22
<211> LENGTH: 13
<212> TYPE: PRT

```
<213> ORGANISM: Artificial Sequence
<220> FEATURE:
<223> OTHER INFORMATION: heavy chain CDR3

<400> SEQUENCE: 22

Gln Gly Thr Thr Ala Leu Ala Thr Arg Phe Phe Asp Val
1               5                   10

<210> SEQ ID NO 23
<211> LENGTH: 11
<212> TYPE: PRT
<213> ORGANISM: Artificial Sequence
<220> FEATURE:
<223> OTHER INFORMATION: light chain CDR1

<400> SEQUENCE: 23

Lys Ala Ser Gln Asp Val Gly Thr Ala Val Ala
1               5                   10

<210> SEQ ID NO 24
<211> LENGTH: 7
<212> TYPE: PRT
<213> ORGANISM: Artificial Sequence
<220> FEATURE:
<223> OTHER INFORMATION: light chain CDR2

<400> SEQUENCE: 24

Ser Ala Ser Tyr Arg Ser Thr
1               5

<210> SEQ ID NO 25
<211> LENGTH: 9
<212> TYPE: PRT
<213> ORGANISM: Artificial Sequence
<220> FEATURE:
<223> OTHER INFORMATION: light chain CDR3

<400> SEQUENCE: 25

Gln His His Tyr Ser Ala Pro Trp Thr
1               5

<210> SEQ ID NO 26

<400> SEQUENCE: 26

000

<210> SEQ ID NO 27

<400> SEQUENCE: 27

000

<210> SEQ ID NO 28
<211> LENGTH: 17
<212> TYPE: PRT
<213> ORGANISM: Artificial Sequence
<220> FEATURE:
<223> OTHER INFORMATION: heavy chain CDR2

<400> SEQUENCE: 28

Thr Val Ser Ser Gly Gly Ser Tyr Ile Tyr Tyr Ala Asp Ser Val Lys
1               5                   10                  15

Gly

<210> SEQ ID NO 29
```

```
<211> LENGTH: 13
<212> TYPE: PRT
<213> ORGANISM: Artificial Sequence
<220> FEATURE:
<223> OTHER INFORMATION: heavy chain CDR3

<400> SEQUENCE: 29

Gln Gly Thr Thr Ala Leu Ala Thr Arg Phe Phe Asp Val
1               5                   10

<210> SEQ ID NO 30
<211> LENGTH: 11
<212> TYPE: PRT
<213> ORGANISM: Artificial Sequence
<220> FEATURE:
<223> OTHER INFORMATION: light chain CDR1

<400> SEQUENCE: 30

Lys Ala Ser Gln Asp Val Gly Thr Ala Val Ala
1               5                   10

<210> SEQ ID NO 31
<211> LENGTH: 7
<212> TYPE: PRT
<213> ORGANISM: Artificial Sequence
<220> FEATURE:
<223> OTHER INFORMATION: light chain CDR2

<400> SEQUENCE: 31

Ser Ala Ser Tyr Arg Ser Thr
1               5

<210> SEQ ID NO 32
<211> LENGTH: 9
<212> TYPE: PRT
<213> ORGANISM: Artificial Sequence
<220> FEATURE:
<223> OTHER INFORMATION: light chain CDR3

<400> SEQUENCE: 32

Gln His His Tyr Ser Ala Pro Trp Thr
1               5

<210> SEQ ID NO 33
<211> LENGTH: 7
<212> TYPE: PRT
<213> ORGANISM: Artificial Sequence
<220> FEATURE:
<223> OTHER INFORMATION: heavy chain CDR1

<400> SEQUENCE: 33

Gly Phe Thr Phe Ser Arg Asn
1               5

<210> SEQ ID NO 34
<211> LENGTH: 10
<212> TYPE: PRT
<213> ORGANISM: Artificial Sequence
<220> FEATURE:
<223> OTHER INFORMATION: heavy chain CDR1

<400> SEQUENCE: 34

Gly Phe Thr Phe Ser Arg Asn Gly Met Ser
1               5                   10

<210> SEQ ID NO 35
<211> LENGTH: 5
```

```
<212> TYPE: PRT
<213> ORGANISM: Artificial Sequence
<220> FEATURE:
<223> OTHER INFORMATION: heavy chain CDR1

<400> SEQUENCE: 35

Arg Asn Gly Met Ser
1               5

<210> SEQ ID NO 36
<211> LENGTH: 6
<212> TYPE: PRT
<213> ORGANISM: Artificial Sequence
<220> FEATURE:
<223> OTHER INFORMATION: heavy chain CDR1

<400> SEQUENCE: 36

Ser Arg Asn Gly Met Ser
1               5

<210> SEQ ID NO 37
<211> LENGTH: 6
<212> TYPE: PRT
<213> ORGANISM: Artificial Sequence
<220> FEATURE:
<223> OTHER INFORMATION: heavy chain CDR2

<400> SEQUENCE: 37

Ser Ser Gly Gly Ser Tyr
1               5

<210> SEQ ID NO 38
<211> LENGTH: 10
<212> TYPE: PRT
<213> ORGANISM: Artificial Sequence
<220> FEATURE:
<223> OTHER INFORMATION: heavy chain CDR2

<400> SEQUENCE: 38

Thr Val Ser Ser Gly Gly Ser Tyr Ile Tyr
1               5                   10

<210> SEQ ID NO 39
<211> LENGTH: 10
<212> TYPE: PRT
<213> ORGANISM: Artificial Sequence
<220> FEATURE:
<223> OTHER INFORMATION: heavy chain CDR2

<400> SEQUENCE: 39

Thr Val Ser Ser Gly Gly Ser Tyr Ile Tyr
1               5                   10

<210> SEQ ID NO 40
<211> LENGTH: 17
<212> TYPE: PRT
<213> ORGANISM: Artificial Sequence
<220> FEATURE:
<223> OTHER INFORMATION: heavy chain CDR2

<400> SEQUENCE: 40

Thr Val Ser Ser Gly Gly Ser Tyr Ile Tyr Tyr Ala Asp Ser Val Lys
1               5                   10                  15

Gly

<210> SEQ ID NO 41
```

```
<211> LENGTH: 15
<212> TYPE: PRT
<213> ORGANISM: Artificial Sequence
<220> FEATURE:
<223> OTHER INFORMATION: heavy chain CDR3

<400> SEQUENCE: 41

Ala Arg Gln Gly Thr Thr Ala Leu Ala Thr Arg Phe Phe Asp Val
1               5                   10                  15

<210> SEQ ID NO 42
<211> LENGTH: 452
<212> TYPE: PRT
<213> ORGANISM: Artificial Sequence
<220> FEATURE:
<223> OTHER INFORMATION: Fc region

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Gly Met Ser Trp Val Arg Gln Ala Pro Gly Lys Gly Leu Glu Trp Val
        35                  40                  45

Ala Thr Val Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Thr Thr Ala Leu Ala Thr Arg Phe Phe Asp Val Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
```

```
                305                 310                 315                 320
        Gly Lys Glu Tyr Lys Cys Lys Val Ser Asn Lys Ala Leu Pro Ala Pro
                        325                 330                 335

Ile Glu Lys Thr Ile Ser Lys Ala Lys Gly Gln Pro Arg Glu Pro Gln
                        340                 345                 350

Val Tyr Thr Leu Pro Pro Ser Arg Glu Glu Met Thr Lys Asn Gln Val
                        355                 360                 365

Ser Leu Thr Cys Leu Val Lys Gly Phe Tyr Pro Ser Asp Ile Ala Val
                370                 375                 380

Glu Trp Glu Ser Asn Gly Gln Pro Glu Asn Asn Tyr Cys Thr Thr Pro
        385                 390                 395                 400

Pro Val Leu Asp Ser Asp Gly Ser Phe Phe Leu Tyr Ser Lys Leu Thr
                        405                 410                 415

Val Asp Lys Ser Arg Trp Gln Gln Gly Asn Val Phe Ser Cys Ser Val
                        420                 425                 430

Met His Glu Ala Leu His Asn His Tyr Thr Gln Lys Ser Leu Ser Cys
                        435                 440                 445

Ser Pro Gly Lys
                    450

<210> SEQ ID NO 43
<211> LENGTH: 452
<212> TYPE: PRT
<213> ORGANISM: Artificial Sequence
<220> FEATURE:
<223> OTHER INFORMATION: Fc region

<400> SEQUENCE: 43

Glu Val Gln Leu Val Glu Ser Gly Gly Gly Leu Val Gln Pro Gly Gly
        1               5                   10                  15

Ser Leu Arg Leu Ser Cys Ala Ala Ser Gly Phe Thr Phe Ser Arg Asn
                        20                  25                  30

Gly Met Ser Trp Val Arg Gln Ala Pro Gly Lys Gly Leu Glu Trp Val
                        35                  40                  45

Ala Thr Val Ser Ser Gly Gly Ser Tyr Ile Tyr Tyr Ala Asp Ser Val
                50                  55                  60

Lys Gly Arg Phe Thr Ile Ser Arg Asp Asn Ala Lys Asn Ser Leu Tyr
        65                  70                  75                  80

Leu Gln Met Asn Ser Leu Arg Ala Glu Asp Thr Ala Val Tyr Tyr Cys
                        85                  90                  95

Ala Arg Gln Gly Thr Thr Ala Leu Ala Thr Arg Phe Phe Asp Val Trp
                        100                 105                 110

Gly Gln Gly Thr Leu Val Thr Val Ser Ser Ala Ser Thr Lys Gly Pro
                        115                 120                 125

Ser Val Phe Pro Leu Ala Pro Ser Ser Lys Ser Thr Ser Gly Gly Thr
                130                 135                 140

Ala Ala Leu Gly Cys Leu Val Lys Asp Tyr Phe Pro Glu Pro Val Thr
        145                 150                 155                 160

Val Ser Trp Asn Ser Gly Ala Leu Thr Ser Gly Val His Thr Phe Pro
                        165                 170                 175

Ala Val Leu Gln Ser Ser Gly Leu Tyr Ser Leu Ser Ser Val Val Thr
                        180                 185                 190

Val Pro Ser Ser Ser Leu Gly Thr Gln Thr Tyr Ile Cys Asn Val Asn
                        195                 200                 205

His Lys Pro Ser Asn Thr Lys Val Asp Lys Lys Val Glu Pro Lys Ser
```

```
            210                 215                 220
Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Cys Phe Ser Cys Ser Val
            420                 425                 430

Met His Glu Ala Leu His Asn His Tyr Thr Gln Lys Ser Leu Ser Cys
        435                 440                 445

Ser Pro Gly Lys
    450

<210> SEQ ID NO 44
<211> LENGTH: 452
<212> TYPE: PRT
<213> ORGANISM: Artificial Sequence
<220> FEATURE:
<223> OTHER INFORMATION: Fc region

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Gly Met Ser Trp Val Arg Gln Ala Pro Gly Lys Gly Leu Glu Trp Val
        35                  40                  45

Ala Thr Val Ser Ser Gly Gly Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Thr Thr Ala Leu Ala Thr Arg Phe Phe Asp Val Trp
            100                 105                 110

Gly Gln Gly Thr Leu Val Thr Val Ser Ser Ala Ser Thr Lys Gly Pro
```

```
            115                 120                 125
Ser Val Phe Pro Leu Ala Pro Ser Ser Lys Ser Thr Ser Gly Gly Thr
    130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                165                 170                 175
Ala Val Leu Gln Ser Ser Gly Leu Tyr Ser Leu Ser Ser Val Val Thr
                180                 185                 190
Val Pro Ser Ser Ser Leu Gly Thr Gln Thr Tyr Ile Cys Asn Val Asn
                195                 200                 205
His Lys Pro Ser Asn Thr Lys Val Asp Lys Lys Val Glu Pro Lys Ser
    210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                245                 250                 255
Met Ile Ser Arg Thr Pro Glu Val Thr Cys Val Val Val Asp Val Ser
            260                 265                 270
His Glu Asp Pro Glu Val Lys Phe Asn Trp Tyr Val Asp Gly Val Glu
            275                 280                 285
Val His Asn Ala Lys Thr Lys Pro Arg Glu Glu Gln Tyr Asn Ser Thr
    290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                325                 330                 335
Ile Glu Lys Thr Ile Ser Lys Ala Lys Gly Gln Pro Arg Glu Pro Gln
            340                 345                 350
Val Tyr Thr Leu Pro Pro Ser Arg Glu Glu Met Thr Lys Asn Gln Val
            355                 360                 365
Ser Leu Thr Cys Leu Val Lys Gly Phe Tyr Pro Ser Asp Ile Ala Val
    370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                405                 410                 415
Val Asp Lys Ser Arg Trp Gln Gln Gly Asn Val Phe Ser Cys Ser Val
                420                 425                 430
Met His Glu Ala Leu His Asn His Tyr Thr Gln Lys Ser Leu Ser Cys
            435                 440                 445
Ser Pro Gly Lys
    450

<210> SEQ ID NO 45
<211> LENGTH: 448
<212> TYPE: PRT
<213> ORGANISM: Artificial Sequence
<220> FEATURE:
<223> OTHER INFORMATION: Fc region

<400> SEQUENCE: 45

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
```

-continued

```
                20                  25                  30
Gly Met Ser Trp Val Arg Gln Ala Pro Gly Lys Gly Leu Glu Trp Val
             35                  40                  45
Ala Thr Val Ser Ser Gly Gly Ser Tyr Ile Tyr Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Gln Gly Thr Thr Ala Leu Ala Thr Arg Phe Phe Asp Val Trp
             100                 105                 110
Gly Gln Gly Thr Leu Val Thr Val Ser Ser Ala Ser Thr Lys Gly Pro
             115                 120                 125
Ser Val Phe Pro Leu Ala Pro Ser Ser Lys Ser Thr Ser Gly Gly Thr
             130                 135                 140
Ala Ala Leu Gly Cys Leu Val Lys Asp Tyr Phe Pro Glu Pro Val Thr
145                 150                 155                 160
Val Ser Trp Asn Ser Gly Ala Leu Thr Ser Gly Val His Thr Phe Pro
                 165                 170                 175
Ala Val Leu Gln Ser Ser Gly Leu Tyr Ser Leu Ser Ser Val Val Thr
             180                 185                 190
Val Pro Ser Ser Ser Leu Gly Thr Gln Thr Tyr Ile Cys Asn Val Asn
             195                 200                 205
His Lys Pro Ser Asn Thr Lys Val Asp Lys Lys Val Glu Pro Lys Ser
         210                 215                 220
Cys Asp Lys Thr His Thr Cys Pro Pro Cys Pro Ala Pro Glu Leu Leu
225                 230                 235                 240
Gly Gly Pro Ser Val Phe Leu Phe Pro Pro Lys Pro Lys Asp Thr Leu
                 245                 250                 255
Met Ile Ser Arg Thr Pro Glu Val Thr Cys Val Val Val Asp Val Ser
             260                 265                 270
His Glu Asp Pro Glu Val Lys Phe Asn Trp Tyr Val Asp Gly Val Glu
             275                 280                 285
Val His Asn Ala Lys Thr Lys Pro Arg Glu Glu Gln Tyr Asn Ser Thr
 290                 295                 300
Tyr Arg Val Val Ser Val Leu Thr Val Leu His Gln Asp Trp Leu Asn
305                 310                 315                 320
Gly Lys Glu Tyr Lys Cys Lys Val Ser Asn Lys Ala Leu Pro Ala Pro
                 325                 330                 335
Ile Glu Lys Thr Ile Ser Lys Ala Lys Gly Gln Pro Arg Glu Pro Cys
             340                 345                 350
Val Tyr Thr Leu Pro Pro Ser Arg Glu Glu Met Thr Lys Asn Gln Val
             355                 360                 365
Ser Leu Thr Cys Leu Val Lys Gly Phe Tyr Pro Ser Asp Ile Ala Val
         370                 375                 380
Glu Trp Glu Ser Asn Gly Gln Pro Glu Asn Asn Tyr Lys Thr Thr Pro
385                 390                 395                 400
Pro Val Leu Asp Ser Asp Gly Ser Phe Phe Leu Tyr Ser Lys Leu Thr
                 405                 410                 415
Val Asp Lys Ser Arg Trp Gln Gln Gly Asn Val Phe Ser Cys Ser Val
             420                 425                 430
Met His Glu Ala Leu His Asn His Tyr Thr Gln Lys Ser Leu Ser Leu
         435                 440                 445
```

<210> SEQ ID NO 46
<211> LENGTH: 214
<212> TYPE: PRT
<213> ORGANISM: Artificial Sequence
<220> FEATURE:
<223> OTHER INFORMATION: Fc region

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Ser Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ser Ala Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Cys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 47
<211> LENGTH: 214
<212> TYPE: PRT
<213> ORGANISM: Artificial Sequence
<220> FEATURE:
<223> OTHER INFORMATION: Fc region

<400> SEQUENCE: 47

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Ser Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ser Ala Pro Trp
```

```
              85                  90                  95
Thr Phe Gly Gly Gly Thr Lys Val Glu Ile Lys Arg Thr Val Ala Cys
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

<210> SEQ ID NO 48
<211> LENGTH: 106
<212> TYPE: PRT
<213> ORGANISM: Artificial Sequence
<220> FEATURE:
<223> OTHER INFORMATION: Fc region

<400> SEQUENCE: 48

```
Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Ala Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```

<210> SEQ ID NO 49
<211> LENGTH: 12
<212> TYPE: PRT
<213> ORGANISM: Artificial Sequence
<220> FEATURE:
<223> OTHER INFORMATION: LCDR1

<400> SEQUENCE: 49

```
Thr Ala Ser Leu Ser Val Ser Ser Thr Tyr Leu His
1               5                   10
```

<210> SEQ ID NO 50
<211> LENGTH: 7
<212> TYPE: PRT
<213> ORGANISM: Artificial Sequence
<220> FEATURE:
<223> OTHER INFORMATION: LCDR2

<400> SEQUENCE: 50

Ser Thr Ser Asn Leu Ala Ser
1               5

<210> SEQ ID NO 51
<211> LENGTH: 9
<212> TYPE: PRT
<213> ORGANISM: Artificial Sequence
<220> FEATURE:
<223> OTHER INFORMATION: LCDR3

<400> SEQUENCE: 51

His Gln Tyr His Arg Ser Pro Leu Thr
1               5

<210> SEQ ID NO 52
<211> LENGTH: 11
<212> TYPE: PRT
<213> ORGANISM: Artificial Sequence
<220> FEATURE:
<223> OTHER INFORMATION: LCDR1

<400> SEQUENCE: 52

Lys Ala Ser Gln Asp Val Gly Thr Ala Val Ala
1               5                   10

<210> SEQ ID NO 53
<211> LENGTH: 7
<212> TYPE: PRT
<213> ORGANISM: Artificial Sequence
<220> FEATURE:
<223> OTHER INFORMATION: LCDR2

<400> SEQUENCE: 53

Ser Ala Ser Tyr Arg Ser Thr
1               5

<210> SEQ ID NO 54
<211> LENGTH: 9
<212> TYPE: PRT
<213> ORGANISM: Artificial Sequence
<220> FEATURE:
<223> OTHER INFORMATION: LCDR3

<400> SEQUENCE: 54

Gln His His Tyr Ser Ala Pro Trp Thr
1               5

<210> SEQ ID NO 55
<211> LENGTH: 6
<212> TYPE: PRT
<213> ORGANISM: Artificial Sequence
<220> FEATURE:
<223> OTHER INFORMATION: HCDR1

<400> SEQUENCE: 55

Thr Lys Tyr Gly Val His
1               5

<210> SEQ ID NO 56
<211> LENGTH: 16
<212> TYPE: PRT
<213> ORGANISM: Artificial Sequence
<220> FEATURE:
<223> OTHER INFORMATION: HCDR2

<400> SEQUENCE: 56

```
Val Lys Trp Ala Gly Gly Ser Thr Asp Tyr Asn Ser Ala Leu Met Ser
 1               5                  10                  15

<210> SEQ ID NO 57
<211> LENGTH: 8
<212> TYPE: PRT
<213> ORGANISM: Artificial Sequence
<220> FEATURE:
<223> OTHER INFORMATION: HCDR3

<400> SEQUENCE: 57

Asp His Arg Asp Ala Met Asp Tyr
 1               5

<210> SEQ ID NO 58
<211> LENGTH: 6
<212> TYPE: PRT
<213> ORGANISM: Artificial Sequence
<220> FEATURE:
<223> OTHER INFORMATION: HCDR1

<400> SEQUENCE: 58

Ser Arg Asn Gly Met Ser
 1               5

<210> SEQ ID NO 59
<211> LENGTH: 17
<212> TYPE: PRT
<213> ORGANISM: Artificial Sequence
<220> FEATURE:
<223> OTHER INFORMATION: HCDR2

<400> SEQUENCE: 59

Thr Val Ser Ser Gly Gly Ser Tyr Ile Tyr Tyr Ala Asp Ser Val Lys
 1               5                  10                  15

Gly

<210> SEQ ID NO 60
<211> LENGTH: 13
<212> TYPE: PRT
<213> ORGANISM: Artificial Sequence
<220> FEATURE:
<223> OTHER INFORMATION: HCDR3

<400> SEQUENCE: 60

Gln Gly Thr Thr Ala Leu Ala Thr Arg Phe Phe Asp Val
 1               5                  10

<210> SEQ ID NO 61
<211> LENGTH: 830
<212> TYPE: DNA
<213> ORGANISM: Artificial Sequence
<220> FEATURE:
<223> OTHER INFORMATION: IL13Ra2 Ab01 VLVH scFv

<400> SEQUENCE: 61
gctagcccgc caccatgctt ctcctggtga caagccttct gctctgtgag ttaccacacc     60
cagcattcct cctgatccca gacatccaga tgacccagtc cccctcttct ctgtctgcct    120
ctgtgggcga cagagtgacc atcacctgta aggccagtca ggatgtaggt actgctgtag    180
cctggtatca gcagaagcct ggcaaggctc ccaagctgct gatctactcg catcctacc    240 ggtccactgg cgtgccttcc agattctccg gctctggctc tggcaccgat ttcaccctga    300
ccatctcctc cctccagcct gaggatttcg ccacctacta ctgccagcac cattatagtg    360
```

| | |
|---|---|
| ctccgtggac gtttggcggc ggaacaaagg tggagatcaa gggtggtggt ggttctggcg | 420 |
| gcggcggctc cggtggtggt ggttctgagg tgcagctggt ggagtctggc ggcggactgg | 480 |
| tgcagcctgg cggctctctg agactgtctt gtgccgcctc cggcttcacc ttcagtagga | 540 |
| atggcatgtc ttgggtgagg caggcccctg gcagggcct ggagtgggtg gccaccgtta | 600 |
| gtagtggtgg tagttacatc tactatgcag acagtgtgaa ggggcggttc accatctcca | 660 |
| gggacaacgc caagaactcc ctgtacctcc agatgaactc cctgagggcc gaggataccg | 720 |
| ccgtgtacta ctgtgccaga caagggacta cggcactagc tacgaggttc ttcgatgtct | 780 |
| ggggccaggg caccctggtg accgtgtcct ctgaatctaa gtacggaccg | 830 |

```
<210> SEQ ID NO 62
<211> LENGTH: 830
<212> TYPE: DNA
<213> ORGANISM: Artificial Sequence
<220> FEATURE:
<223> OTHER INFORMATION: IL13Ra2 Ab01 VHVL scFv
      Ab01-VL sequence
      Ab01-VH sequence
      ATG Start codon
      Gctagc = 5'-NheI restriction site
      Cggaccg = 3'-RsrII restriction site

<400> SEQUENCE: 62
```

| | |
|---|---|
| gctagcccgc caccatgctt ctcctggtga caagccttct gctctgtgag ttaccacacc | 60 |
| cagcattcct cctgatccca gaggtgcagc tggtggagtc tggcggcgga ctggtgcagc | 120 |
| ctggcggctc tctgagactg tcttgtgccg cctccggctt caccttcagt aggaatggca | 180 |
| tgtcttgggt gaggcaggcc cctggcaagg gcctggagtg ggtggccacc gttagtagtg | 240 |
| gtggtagtta catctactat gcagacagtg tgaaggggcg gttcaccatc tccagggaca | 300 |
| acgccaagaa ctccctgtac ctccagatga actccctgag ggccgaggat accgccgtgt | 360 |
| actactgtgc cagacaaggg actacggcac tagctacgag gttcttcgat gtctggggcc | 420 |
| agggcaccct ggtgaccgtg tcctctggtg gtggtggttc tggcggcggc ggctccggtg | 480 |
| gtggtggttc tgacatccag atgacccagt cccctctctt ctgtctgcc tctgtgggcg | 540 |
| acagagtgac catcacctgt aaggccagtc aggatgtagg tactgctgta gcctggtatc | 600 |
| agcagaagcc tggcaaggct cccaagctgc tgatctactc ggcatcctac cggtccactg | 660 |
| gcgtgccttc cagattctcc ggctctggct ctggcaccga tttcacccctg accatctcct | 720 |
| ccctccagcc tgaggatttc gccacctact actgccagca ccattatagt gctccgtgga | 780 |
| cgtttggcgg cggaacaaag gtggagatca aggaatctaa gtacggaccg | 830 |

```
<210> SEQ ID NO 63
<211> LENGTH: 815
<212> TYPE: DNA
<213> ORGANISM: Artificial Sequence
<220> FEATURE:
<223> OTHER INFORMATION: IL13Ra2 Ab02 VLVH scFv

<400> SEQUENCE: 63
```

| | |
|---|---|
| gctagcccgc caccatgctt ctcctggtga caagccttct gctctgtgag ttaccacacc | 60 |
| cagcattcct cctgatccca gatattcaga tgacccagag cccgagcagc ctgagcgcga | 120 |
| gcgtgggcga tcgcgtgacc attacctgca ccgcgagcct gagcgtgagc agcacctatc | 180 |
| tgcattggta tcagcagaaa ccgggcaaag cgccgaaact gctgatttat agcaccagca | 240 |
| acctggcgag cggcgtgccg agccgcttta gcggcagcgg cagcggcacc gattttaccc | 300 |

-continued

| | |
|---|---|
| tgaccattag cagcctgcag ccggaagatt ttgcgaccta ttattgccat cagtatcatc | 360 |
| gcagcccgct gacctttggc ggcggcacca aagtggaaat taaagtggt ggtggttctg | 420 |
| gcggcggcgg ctccggtggt ggtggttctg aagtgcagct ggtggaaagc ggcggcggcc | 480 |
| tggtgcagcc gggcggcagc ctgcgcctga gctgcgcggc gagcggcttt acctttacca | 540 |
| aatatggcgt gcattgggtg cgccaggcgc cgggcaaagg cctggaatgg gtggcggtga | 600 |
| aatgggcggg cggcagcacc gattataaca gcgcgctgat gagccgcttt accattagcc | 660 |
| gcgataacgc gaaaaacagc ctgtatctgc agatgaacag cctgcgcgcg aagataccg | 720 |
| cggtgtatta ttgcgcgcgc gatcatcgcg atgcgatgga ttattgggc agggcaccc | 780 |
| tggtgaccgt gagcagcgaa tctaagtacg accg | 815 |

<210> SEQ ID NO 64
<211> LENGTH: 815
<212> TYPE: DNA
<213> ORGANISM: Artificial Sequence
<220> FEATURE:
<223> OTHER INFORMATION: IL13Ra2 Ab02 VHVL scFv
    Ab02-VL sequence
    Ab02-VH sequence
    ATG Start codon
    Gctagc = 5'-NheI restriction site
    Cggaccg = 3'-RsrII restriction site

<400> SEQUENCE: 64

| | |
|---|---|
| gctagcccgc caccatgctt ctcctggtga caagccttct gctctgtgag ttaccacacc | 60 |
| cagcattcct cctgatccca gaagtgcagc tggtggaaag cggcggcggc ctggtgcagc | 120 |
| cgggcggcag cctgcgcctg agctgcgcgg cgagcggctt tacctttacc aaatatggcg | 180 |
| tgcattgggt gcgccaggcg ccgggcaaag gcctggaatg ggtggcggtg aaatgggcgg | 240 |
| gcggcagcac cgattataac agcgcgctga tgagccgctt taccattagc cgcgataacg | 300 |
| cgaaaaacag cctgtatctg cagatgaaca gcctgcgcgc ggaagatacc gcggtgtatt | 360 |
| attgcgcgcg cgatcatcgc gatgcgatgg attattgggg ccagggcacc ctggtgaccg | 420 |
| tgagcagcgg tggtggtggt tctggcggcg gcggctccgg tggtggtggt tctgatattc | 480 |
| agatgaccca gagcccgagc agcctgagcg cgagcgtggg cgatcgcgtg accattacct | 540 |
| gcaccgcgag cctgagcgtg agcagcacct atctgcattg gtatcagcag aaaccgggca | 600 |
| aagcgccgaa actgctgatt tatagcacca gcaacctggc gagcggcgtg ccgagccgct | 660 |
| ttagcggcag cggcagcggc accgatttta ccctgaccat tagcagcctg cagccggaag | 720 |
| attttgcgac ctattattgc catcagtatc atcagccc gctgaccttt ggcggcggca | 780 |
| ccaaagtgga aattaaagaa tctaagtacg accg | 815 |

<210> SEQ ID NO 65
<211> LENGTH: 122
<212> TYPE: PRT
<213> ORGANISM: Artificial Sequence
<220> FEATURE:
<223> OTHER INFORMATION: Ab01-VH

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Asn
            20                  25                  30

Gly Met Ser Trp Val Arg Gln Ala Pro Gly Lys Gly Leu Glu Trp Val
        35                  40                  45

```
Ala Thr Val Ser Ser Gly Gly Ser Tyr Ile Tyr Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Gly Thr Thr Ala Leu Ala Thr Arg Phe Phe Asp Val Trp
            100                 105                 110

Gly Gln Gly Thr Leu Val Thr Val Ser Ser
            115                 120

<210> SEQ ID NO 66
<211> LENGTH: 6
<212> TYPE: PRT
<213> ORGANISM: Artificial Sequence
<220> FEATURE:
<223> OTHER INFORMATION: Ab01 HCDR1

<400> SEQUENCE: 66

Ser Arg Asn Gly Met Ser
1               5

<210> SEQ ID NO 67
<211> LENGTH: 17
<212> TYPE: PRT
<213> ORGANISM: artificial sequence
<220> FEATURE:
<223> OTHER INFORMATION: Ab01 HCDR2

<400> SEQUENCE: 67

Thr Val Ser Ser Gly Gly Ser Tyr Ile Tyr Tyr Ala Asp Ser Val Lys
1               5                   10                  15

Gly

<210> SEQ ID NO 68
<211> LENGTH: 13
<212> TYPE: PRT
<213> ORGANISM: Artificial Sequence
<220> FEATURE:
<223> OTHER INFORMATION: Ab01 HCDR3

<400> SEQUENCE: 68

Gln Gly Thr Thr Ala Leu Ala Thr Arg Phe Phe Asp Val
1               5                   10

<210> SEQ ID NO 69
<211> LENGTH: 107
<212> TYPE: PRT
<213> ORGANISM: Artificial Sequence
<220> FEATURE:
<223> OTHER INFORMATION: Ab01-VL

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Gly Thr Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Ser Thr Gly Val Pro Ser Arg Phe Ser Gly
 50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ser Ala Pro Trp
                85                  90                  95

Thr Phe Gly Gly Gly Thr Lys Val Glu Ile Lys
            100                 105

<210> SEQ ID NO 70
<211> LENGTH: 11
<212> TYPE: PRT
<213> ORGANISM: Artificial Sequence
<220> FEATURE:
<223> OTHER INFORMATION: Ab01 LCDR1

<400> SEQUENCE: 70

Lys Ala Ser Gln Asp Val Gly Thr Ala Val Ala
1               5                   10

<210> SEQ ID NO 71
<211> LENGTH: 7
<212> TYPE: PRT
<213> ORGANISM: Artificial Sequence
<220> FEATURE:
<223> OTHER INFORMATION: Ab01 LCDR2

<400> SEQUENCE: 71

Ser Ala Ser Tyr Arg Ser Thr
1               5

<210> SEQ ID NO 72
<211> LENGTH: 9
<212> TYPE: PRT
<213> ORGANISM: Artificial Sequence
<220> FEATURE:
<223> OTHER INFORMATION: Ab01 LCDR3

<400> SEQUENCE: 72

Gln His His Tyr Ser Ala Pro Trp Thr
1               5

<210> SEQ ID NO 73
<211> LENGTH: 116
<212> TYPE: PRT
<213> ORGANISM: Artificial Sequence
<220> FEATURE:
<223> OTHER INFORMATION: Ab02-VH

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Lys Tyr
            20                  25                  30

Gly Val His Trp Val Arg Gln Ala Pro Gly Lys Gly Leu Glu Trp Val
        35                  40                  45

Ala Val Lys Trp Ala Gly Gly Ser Thr Asp Tyr Asn Ser Ala Leu Met
    50                  55                  60

Ser Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asp His Arg Asp Ala Met Asp Tyr Trp Gly Gln Gly Thr Leu Val
            100                 105                 110
```

```
Thr Val Ser Ser
        115

<210> SEQ ID NO 74
<211> LENGTH: 6
<212> TYPE: PRT
<213> ORGANISM: Artificial Sequence
<220> FEATURE:
<223> OTHER INFORMATION: Ab02 HCDR1

<400> SEQUENCE: 74

Thr Lys Tyr Gly Val His
1               5

<210> SEQ ID NO 75
<211> LENGTH: 16
<212> TYPE: PRT
<213> ORGANISM: Artificial Sequence
<220> FEATURE:
<223> OTHER INFORMATION: Ab02 HCDR2

<400> SEQUENCE: 75

Val Lys Trp Ala Gly Gly Ser Thr Asp Tyr Asn Ser Ala Leu Met Ser
1               5                   10                  15

<210> SEQ ID NO 76
<211> LENGTH: 8
<212> TYPE: PRT
<213> ORGANISM: Artificial Sequence
<220> FEATURE:
<223> OTHER INFORMATION: Ab02 HCDR3

<400> SEQUENCE: 76

Asp His Arg Asp Ala Met Asp Tyr
1               5

<210> SEQ ID NO 77
<211> LENGTH: 108
<212> TYPE: PRT
<213> ORGANISM: Artificial Sequence
<220> FEATURE:
<223> OTHER INFORMATION: Ab02-VL

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Thr Ala Ser Leu Ser Val Ser Ser Thr
            20                  25                  30

Tyr Leu His Trp Tyr Gln Gln Lys Pro Gly Lys Ala Pro Lys Leu Leu
        35                  40                  45

Ile Tyr Ser Thr Ser Asn Leu Ala Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys His Gln Tyr His Arg Ser Pro
                85                  90                  95

Leu Thr Phe Gly Gly Gly Thr Lys Val Glu Ile Lys
            100                 105

<210> SEQ ID NO 78
<211> LENGTH: 12
<212> TYPE: PRT
<213> ORGANISM: Artificial Sequence
<220> FEATURE:
```

<223> OTHER INFORMATION: Ab02 LCDR1

<400> SEQUENCE: 78

Thr Ala Ser Leu Ser Val Ser Thr Tyr Leu His
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Ab02 LCDR2

<400> SEQUENCE: 79

Ser Thr Ser Asn Leu Ala Ser
1               5

<210> SEQ ID NO 80
<211> LENGTH: 9
<212> TYPE: PRT
<213> ORGANISM: Artificial Sequence
<220> FEATURE:
<223> OTHER INFORMATION: Ab02 LCDR3

<400> SEQUENCE: 80

His Gln Tyr His Arg Ser Pro Leu Thr
1               5

<210> SEQ ID NO 81
<211> LENGTH: 187
<212> TYPE: PRT
<213> ORGANISM: Artificial Sequence
<220> FEATURE:
<223> OTHER INFORMATION: DHFRdm

<400> SEQUENCE: 81

Met Val Gly Ser Leu Asn Cys Ile Val Ala Val Ser Gln Asn Met Gly
1               5                   10                  15

Ile Gly Lys Asn Gly Asp Phe Pro Trp Pro Leu Arg Asn Glu Ser
            20                  25                  30

Arg Tyr Phe Gln Arg Met Thr Thr Thr Ser Ser Val Glu Gly Lys Gln
        35                  40                  45

Asn Leu Val Ile Met Gly Lys Lys Thr Trp Phe Ser Ile Pro Glu Lys
    50                  55                  60

Asn Arg Pro Leu Lys Gly Arg Ile Asn Leu Val Leu Ser Arg Glu Leu
65                  70                  75                  80

Lys Glu Pro Pro Gln Gly Ala His Phe Leu Ser Arg Ser Leu Asp Asp
                85                  90                  95

Ala Leu Lys Leu Thr Glu Gln Pro Glu Leu Ala Asn Lys Val Asp Met
            100                 105                 110

Val Trp Ile Val Gly Gly Ser Ser Val Tyr Lys Glu Ala Met Asn His
        115                 120                 125

Pro Gly His Leu Lys Leu Phe Val Thr Arg Ile Met Gln Asp Phe Glu
    130                 135                 140

Ser Asp Thr Phe Phe Pro Glu Ile Asp Leu Glu Lys Tyr Lys Leu Leu
145                 150                 155                 160

Pro Glu Tyr Pro Gly Val Leu Ser Asp Val Gln Glu Lys Gly Ile
                165                 170                 175

Lys Tyr Lys Phe Glu Val Tyr Glu Lys Asn Asp
            180                 185

<210> SEQ ID NO 82
<211> LENGTH: 564
<212> TYPE: DNA
<213> ORGANISM: Artificial Sequence
<220> FEATURE:
<223> OTHER INFORMATION: DHFRdm

<400> SEQUENCE: 82

```
atggttggtt cgctaaactg catcgtcgct gtgtcccaga acatgggcat cggcaagaac    60
ggggacttcc cctggccacc gctcaggaat gaatccagat atttccagag aatgaccaca   120
acctcttcag tagaaggtaa acagaatctg gtgattatgg gtaagaagac ctggttctcc   180
attcctgaga agaatcgacc tttaaagggt agaattaatt tagttctcag cagagaactc   240
aaggaacctc cacaaggagc tcattttctt tccagaagtc tagatgatgc cttaaaactt   300
actgaacaac cagaattagc aaataaagta gacatggtct ggatagttgg tggcagttct   360
gtttataagg aagccatgaa tcacccaggc catcttaaac tatttgtgac aaggatcatg   420
caagactttg aaagtgacac gttttttcca gaaattgatt tggagaaata taaacttctg   480
ccagaatacc caggtgttct ctctgatgtc caggaggaga aaggcattaa gtacaaattt   540
gaagtatatg agaagaatga ttaa                                          564
```

<210> SEQ ID NO 83
<211> LENGTH: 66
<212> TYPE: DNA
<213> ORGANISM: Artificial Sequence
<220> FEATURE:
<223> OTHER INFORMATION: GMCSFss
      Leader

<400> SEQUENCE: 83

```
atgcttctcc tggtgacaag ccttctgctc tgtgagttac cacacccagc attcctcctg    60
atccca                                                               66
```

<210> SEQ ID NO 84
<211> LENGTH: 321
<212> TYPE: DNA
<213> ORGANISM: Artificial Sequence
<220> FEATURE:
<223> OTHER INFORMATION: Ab01-VL

<400> SEQUENCE: 84

```
gacatccaga tgacccagtc cccctcttct ctgtctgcct ctgtgggcga cagagtgacc    60
atcacctgta aggccagtca ggatgtaggt actgctgtag cctggtatca gcagaagcct   120
ggcaaggctc ccaagctgct gatctactcg gcatcctacc ggtccactgg cgtgccttcc   180
agattctccg gctctggctc tggcaccgat ttcaccctga ccatctcctc cctcagcct   240
gaggatttcg ccacctacta ctgccagcac cattatagtg ctccgtggac gtttggcggc   300
ggaacaaagg tggagatcaa g                                             321
```

<210> SEQ ID NO 85
<211> LENGTH: 366
<212> TYPE: DNA
<213> ORGANISM: Artificial Sequence
<220> FEATURE:
<223> OTHER INFORMATION: Ab01-VH

<400> SEQUENCE: 85

```
gaggtgcagc tggtggagtc tggcggcgga ctggtgcagc ctggcggctc tctgagactg    60
```

| | |
|---|---|
| tcttgtgccg cctccggctt caccttcagt aggaatggca tgtcttgggt gaggcaggcc | 120 |
| cctggcaagg gcctggagtg ggtggccacc gttagtagtg gtggtagtta catctactat | 180 |
| gcagacagtg tgaaggggcg gttcaccatc tccagggaca acgccaagaa ctccctgtac | 240 |
| ctccagatga actccctgag ggccgaggat accgccgtgt actactgtgc cagacaaggg | 300 |
| actacggcac tagctacgag gttcttcgat gtctggggcc agggcaccct ggtgaccgtg | 360 |
| tcctct | 366 |

<210> SEQ ID NO 86
<211> LENGTH: 324
<212> TYPE: DNA
<213> ORGANISM: Artificial Sequence
<220> FEATURE:
<223> OTHER INFORMATION: Ab02-VL

<400> SEQUENCE: 86

| | |
|---|---|
| gatattcaga tgacccagag cccgagcagc ctgagcgcga gcgtgggcga tcgcgtgacc | 60 |
| attacctgca ccgcgagcct gagcgtgagc agcacctatc tgcattggta tcagcagaaa | 120 |
| ccgggcaaag cgccgaaact gctgatttat agcaccagca acctggcgag cggcgtgccg | 180 |
| agccgcttta gcggcagcgg cagcggcacc gattttaccc tgaccattag cagcctgcag | 240 |
| ccggaagatt ttgcgaccta ttattgccat cagtatcatc gcagcccgct gacctttggc | 300 |
| ggcggcacca aagtggaaat taaa | 324 |

<210> SEQ ID NO 87
<211> LENGTH: 348
<212> TYPE: DNA
<213> ORGANISM: Artificial Sequence
<220> FEATURE:
<223> OTHER INFORMATION: Ab02-VH

<400> SEQUENCE: 87

| | |
|---|---|
| gaagtgcagc tggtggaaag cggcggcggc ctggtgcagc cgggcggcag cctgcgcctg | 60 |
| agctgcgcgg cgagcggctt tacctttacc aaatatggcg tgcattgggt gcgccaggcg | 120 |
| ccgggcaaag gcctggaatg ggtggcggtg aaatgggcgg cggcagcac cgattataac | 180 |
| agcgcgctga tgagccgctt taccattagc cgcgataacg cgaaaaacag cctgtatctg | 240 |
| cagatgaaca gcctgcgcgc ggaagatacc gcggtgtatt attgcgcgcg cgatcatcgc | 300 |
| gatgcgatgg attattgggg ccagggcacc ctggtgaccg tgagcagc | 348 |

<210> SEQ ID NO 88
<211> LENGTH: 45
<212> TYPE: DNA
<213> ORGANISM: Artificial Sequence
<220> FEATURE:
<223> OTHER INFORMATION: (Gly-Gly-Gly-Ser)x3 linker

<400> SEQUENCE: 88

| | |
|---|---|
| ggtggtggtg gttctggcgg cggcggctcc ggtggtggtg gttct | 45 |

<210> SEQ ID NO 89
<211> LENGTH: 732
<212> TYPE: DNA
<213> ORGANISM: Artificial Sequence
<220> FEATURE:
<223> OTHER INFORMATION: Ab01 scFv VLVH

<400> SEQUENCE: 89

| | |
|---|---|
| gacatccaga tgacccagtc cccctcttct ctgtctgcct ctgtgggcga cagagtgacc | 60 |

| | |
|---|---|
| atcacctgta aggccagtca ggatgtaggt actgctgtag cctggtatca gcagaagcct | 120 |
| ggcaaggctc ccaagctgct gatctactcg gcatcctacc ggtccactgg cgtgccttcc | 180 |
| agattctccg gctctggctc tggcaccgat ttcaccctga ccatctcctc cctccagcct | 240 |
| gaggatttcg ccacctacta ctgccagcac cattatagtg ctccgtggac gtttggcggc | 300 |
| ggaacaaagg tggagatcaa gggtggtggt ggttctggcg gcggcggctc cggtggtggt | 360 |
| ggttctgagg tgcagctggt ggagtctggc ggcggactgg tgcagcctgg cggctctctg | 420 |
| agactgtctt gtgccgcctc cggcttcacc ttcagtagga atggcatgtc ttgggtgagg | 480 |
| caggcccctg gcaagggcct ggagtgggtg gccaccgtta gtagtggtgg tagttacatc | 540 |
| tactatgcag acagtgtgaa ggggcggttc accatctcca gggacaacgc caagaactcc | 600 |
| ctgtacctcc agatgaactc cctgagggcc gaggataccg ccgtgtacta ctgtgccaga | 660 |
| caagggacta cggcactagc tacgaggttc ttcgatgtct ggggccaggg caccctggtg | 720 |
| accgtgtcct ct | 732 |

<210> SEQ ID NO 90
<211> LENGTH: 732
<212> TYPE: DNA
<213> ORGANISM: Artificial Sequence
<220> FEATURE:
<223> OTHER INFORMATION: Ab01 scFv VHVL

<400> SEQUENCE: 90

| | |
|---|---|
| gaggtgcagc tggtggagtc tggcggcgga ctggtgcagc ctggcggctc tctgagactg | 60 |
| tcttgtgccg cctccggctt caccttcagt aggaatggca tgtcttgggt gaggcaggcc | 120 |
| cctggcaagg gcctggagtg ggtggccacc gttagtagtg gtggtagtta catctactat | 180 |
| gcagacagtg tgaaggggcg gttcaccatc tccagggaca cgccaagaa ctccctgtac | 240 |
| ctccagatga actccctgag ggccgaggat accgccgtgt actactgtgc cagacaaggg | 300 |
| actacggcac tagctacgag gttcttcgat gtctggggcc agggcaccct ggtgaccgtg | 360 |
| tcctctggtg gtggtggttc tggcggcggc ggctccggtg gtggtggttc tgacatccag | 420 |
| atgacccagt ccccctcttc tctgtctgcc tctgtgggcg acagagtgac catcacctgt | 480 |
| aaggccagtc aggatgtagg tactgctgta gcctggtatc agcagaagcc tggcaaggct | 540 |
| cccaagctgc tgatctactc ggcatcctac cggtccactg gcgtgccttc agattctccg | 600 |
| gctctggct ctggcaccga tttcaccctg accatctcct cctccagcc tgaggatttc | 660 |
| gccacctact actgccagca ccattatagt gctccgtgga cgtttggcgg cggaacaaag | 720 |
| gtggagatca ag | 732 |

<210> SEQ ID NO 91
<211> LENGTH: 717
<212> TYPE: DNA
<213> ORGANISM: Artificial Sequence
<220> FEATURE:
<223> OTHER INFORMATION: Ab02 scFv VLVH

<400> SEQUENCE: 91

| | |
|---|---|
| gatattcaga tgacccagag cccgagcagc ctgagcgcga gcgtgggcga tcgcgtgacc | 60 |
| attacctgca ccgcgagcct gagcgtgagc agcacctatc tgcattggta tcagcagaaa | 120 |
| ccgggcaaag cgccgaaact gctgatttat agcaccagca acctggcgag cggcgtgccg | 180 |
| agccgcttta gcggcagcgg cagcggcacc gattttaccc tgaccattag cagcctgcag | 240 |

```
ccggaagatt ttgcgaccta ttattgccat cagtatcatc gcagcccgct gacctttggc    300
ggcggcacca aagtggaaat taaaggtggt ggtggttctg cggcggcggc ctccggtggt    360
ggtggttctg aagtgcagct ggtggaaagc ggcggcggcc tggtgcagcc gggcggcagc    420
ctgcgcctga gctgcgcggc gagcggcttt acctttacca aatatggcgt gcattgggtg    480
cgccaggcgc cgggcaaagg cctggaatgg gtggcggtga atgggcggg cggcagcacc    540 gattataaca gcgcgctgat gagccgcttt accattagcc gcgataacgc gaaaaacagc    600
ctgtatctgc agatgaacag cctgcgcgcg gaagataccg cggtgtatta ttgcgcgcgc    660
gatcatcgcg atgcgatgga ttattggggc cagggcaccc tggtgaccgt gagcagc      717

<210> SEQ ID NO 92
<211> LENGTH: 717
<212> TYPE: DNA
<213> ORGANISM: Artificial Sequence
<220> FEATURE:
<223> OTHER INFORMATION: Ab02 scFv VHVL

<400> SEQUENCE: 92
gaagtgcagc tggtggaaag cggcggcggc ctggtgcagc cgggcggcag cctgcgcctg    60
agctgcgcgg cgagcggctt tacctttacc aaatatggcg tgcattgggt gcgccaggcg    120
ccgggcaaag gcctggaatg gtggcggtg aaatgggcgg cggcagcac cgattataac    180 agcgcgctga tgagccgctt taccattagc cgcgataacg cgaaaaacag cctgtatctg    240
cagatgaaca gcctgcgcgc ggaagatacc gcggtgtatt attgcgcgcg cgatcatcgc    300
gatgcgatgg attattgggg ccagggcacc ctggtgaccg tgagcagcgg tggtggtggt    360
tctggcggcg gcggctccgg tggtggtggt tctgatattc agatgaccca gagcccgagc    420
agcctgagcg cgagcgtggg cgatcgcgtg accattacct gcaccgcgag cctgagcgtg    480
agcagcacct atctgcattg gtatcagcag aaaccgggca agcgccgaa actgctgatt    540 tatagccacc gcaacctggc gagcggcgtg ccgagccgct ttagcggcag cggcagcggc    600 accgattttac ccctgaccat tagcagcctg cagccggaag attttgcgac ctattattgc    660
catcagtatc atcgcagccc gctgaccttt ggcggcggca ccaaagtgga aattaaa      717

<210> SEQ ID NO 93
<211> LENGTH: 36
<212> TYPE: DNA
<213> ORGANISM: Artificial Sequence
<220> FEATURE:
<223> OTHER INFORMATION: S spacer

<400> SEQUENCE: 93
gaatctaagt acggaccgcc ctgcccccct tgccct                               36

<210> SEQ ID NO 94
<211> LENGTH: 84
<212> TYPE: DNA
<213> ORGANISM: Artificial Sequence
<220> FEATURE:
<223> OTHER INFORMATION: CD28tm

<400> SEQUENCE: 94
atgttctggg tgctggtggt ggtcggaggc gtgctggcct gctacagcct gctggtcacc    60
gtggccttca tcatcttttg ggtg                                            84

<210> SEQ ID NO 95
<211> LENGTH: 126
```

<212> TYPE: DNA
<213> ORGANISM: Artificial Sequence
<220> FEATURE:
<223> OTHER INFORMATION: 41-BB

<400> SEQUENCE: 95

```
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126
```

<210> SEQ ID NO 96
<211> LENGTH: 336
<212> TYPE: DNA
<213> ORGANISM: Artificial Sequence
<220> FEATURE:
<223> OTHER INFORMATION: CD3?

<400> SEQUENCE: 96

```
cgggtgaagt tcagcagaag cgccgacgcc cctgcctacc agcagggcca gaatcagctg    60
tacaacgagc tgaacctggg cagaagggaa gagtacgacg tcctggataa gcggagaggc   120
cgggaccctg agatgggcgg caagcctcgg cggaagaacc cccaggaagg cctgtataac   180
gaactgcaga agacaagat ggccgaggcc tacagcgaga tcggcatgaa gggcgagcgg   240
aggcggggca agggccacga cggcctgtat cagggcctgt ccaccgccac caaggatacc   300
tacgacgccc tgcacatgca ggccctgccc ccaagg                             336
```

<210> SEQ ID NO 97
<211> LENGTH: 72
<212> TYPE: DNA
<213> ORGANISM: Artificial Sequence
<220> FEATURE:
<223> OTHER INFORMATION: T2A

<400> SEQUENCE: 97

```
ctcgagggcg gcggagaggg cagaggaagt cttctaacat gcggtgacgt ggaggagaat    60
cccggcccta gg                                                        72
```

<210> SEQ ID NO 98
<211> LENGTH: 1005
<212> TYPE: DNA
<213> ORGANISM: Artificial Sequence
<220> FEATURE:
<223> OTHER INFORMATION: EGFRt

<400> SEQUENCE: 98

```
cgcaaagtgt gtaacggaat aggtattggt gaatttaaag actcactctc cataaatgct    60
acgaatatta aacacttcaa aaactgcacc tccatcagtg cgatctcca catcctgccg    120
gtggcattta ggggtgactc cttcacacat actcctcctc tggatccaca ggaactggat   180
attctgaaaa ccgtaaagga atcacaggg ttttgctga ttcaggcttg gcctgaaaac    240
aggacggacc tccatgcctt tgagaaccta gaaatcatac gcggcaggac caagcaacat   300
ggtcagtttt ctcttgcagt cgtcagcctg aacataacat ccttgggatt acgctccctc   360
aaggagataa gtgatggaga tgtgataatt tcaggaaaca aaaatttgtg ctatgcaaat   420
acaataaaact ggaaaaaact gtttgggacc tccggtcaga aaccaaaat tataagcaac   480
agaggtgaaa acagctgcaa ggccacaggc caggtctgcc atgccttgtg ctcccccgag   540
ggctgctggg gcccggagcc cagggactgc gtctcttgcc ggaatgtcag ccgaggcagg   600
```

```
gaatgcgtgg acaagtgcaa ccttctggag ggtgagccaa gggagtttgt ggagaactct        660
gagtgcatac agtgccaccc agagtgcctg cctcaggcca tgaacatcac ctgcacagga        720
cggggaccag acaactgtat ccagtgtgcc cactacattg acggccccca ctgcgtcaag        780
acctgcccgg caggagtcat gggagaaaac aacaccctgg tctggaagta cgcagacgcc        840
ggccatgtgt gccacctgtg ccatccaaac tgcacctacg gatgcactgg gccaggtctt        900
gaaggctgtc caacgaatgg gcctaagatc cgtccatcg ccactgggat ggtgggggcc         960
ctcctcttgc tgctggtggt ggccctgggg atcggcctct tcatg                      1005
```

<210> SEQ ID NO 99
<211> LENGTH: 564
<212> TYPE: DNA
<213> ORGANISM: Artificial Sequence
<220> FEATURE:
<223> OTHER INFORMATION: DHFRdm

<400> SEQUENCE: 99

```
atggttggtt cgctaaactg catcgtcgct gtgtcccaga acatgggcat cggcaagaac         60
ggggacttcc cctggccacc gctcaggaat gaatccagat atttccagag aatgaccaca        120
acctcttcag tagaaggtaa acagaatctg gtgattatgg gtaagaagac ctggttctcc        180
attcctgaga gaatcgacc tttaaagggt agaattaatt tagttctcag cagagaactc        240
aaggaacctc cacaaggagc tcattttctt tccagaagtc tagatgatgc cttaaaactt        300
actgaacaac cagaattagc aaataaagta gacatggtct ggatagttgg tggcagttct        360
gtttataagg aagccatgaa tcacccaggc catcttaaac tatttgtgac aaggatcatg        420
caagactttg aaagtgacac gttttttcca gaaattgatt tggagaaata taaacttctg        480
ccagaatacc caggtgttct ctctgatgtc caggaggaga aaggcattaa gtacaaattt        540
gaagtatatg agaagaatga ttaa                                             564
```

<210> SEQ ID NO 100
<211> LENGTH: 357
<212> TYPE: DNA
<213> ORGANISM: Artificial Sequence
<220> FEATURE:
<223> OTHER INFORMATION: M spacer

<400> SEQUENCE: 100

```
gaatctaagt acggaccgcc ctgccccct tgccctggcc agcctagaga accccaggtg          60
tacaccctgc ctcccagcca ggaagagatg accaagaacc aggtgtccct gacctgcctg        120
gtcaaaggct tctaccccag cgatatcgcc gtggaatggg agagcaacgg ccagcccgag        180
aacaactaca agaccacccc ccctgtgctg gacagcgacg gcagcttctt cctgtactcc        240
cggctgaccg tggacaagag ccggtggcag gaaggcaacg tcttcagctg cagcgtgatg        300
cacgaggccc tgcacaacca ctacacccag aagtccctga cctgagcct gggcaag            357
```

<210> SEQ ID NO 101
<211> LENGTH: 685
<212> TYPE: DNA
<213> ORGANISM: Artificial Sequence
<220> FEATURE:
<223> OTHER INFORMATION: L spacer

<400> SEQUENCE: 101

```
atctaagtac ggaccgccct gccccccttg ccctgccccc gagttcgacg gcggacccag         60
cgtgttcctg ttccccccca gcccaaggga caccctgatg atcagccgga ccccgaggt        120
```

-continued

```
gacctgcgtg gtggtggacg tgagccagga agatcccgag gtccagttca attggtacgt    180
ggacggcgtg gaagtgcaca acgccaagac caagcccaga gaggaacagt tccagagcac    240
ctaccgggtg gtgtctgtgc tgaccgtgct gcaccaggac tggctgaacg gcaaagaata    300
caagtgcaag gtgtccaaca agggcctgcc cagcagcatc gaaaagacca tcagcaaggc    360
caagggccag cctcgcgagc cccaggtgta caccctgcct ccctcccagg aagagatgac    420
caagaaccag gtgtccctga cctgcctggt gaagggcttc tacccagcg acatcgccgt    480 ggagtgggag agcaacggcc agcctgagaa caactacaag accacccctc ccgtgctgga    540
cagcgacggc agcttcttcc tgtacagccg gctgaccgtg gacaagagcc ggtggcagga    600
aggcaacgtc tttagctgca gcgtgatgca cgaggccctg cacaaccact acacccagaa    660
gagcctgagc ctgtccctgg gcaag                                          685
```